(12) United States Patent
Filipi et al.

(10) Patent No.: US 8,906,040 B2
(45) Date of Patent: Dec. 9, 2014

(54) SYSTEMS AND TECHNIQUES FOR MINIMALLY INVASIVE GASTROINTESTINAL PROCEDURES

(75) Inventors: Charles J. Filipi, Omaha, NE (US); Jason L. Addink, Gilbert, AZ (US); Scott D. Klopfenstein, Phoenix, AZ (US); Aaron B. Moncur, Mesa, AZ (US); Timothy B. Hunt, Chandler, AZ (US)

(73) Assignee: Creighton University, Omaha, NE (US)

( * ) Notice: Subject to any disclaimer, the term of this patent is extended or adjusted under 35 U.S.C. 154(b) by 1462 days.

(21) Appl. No.: 12/134,685

(22) Filed: Jun. 6, 2008

(65) Prior Publication Data

US 2008/0275473 A1 Nov. 6, 2008

Related U.S. Application Data

(63) Continuation of application No. PCT/US2006/061665, filed on Dec. 6, 2006, which is a continuation-in-part of application No. 11/457,442, filed on Jul. 13, 2006, now Pat. No. 8,641,729.

(60) Provisional application No. 60/698,748, filed on Jul. 13, 2005, provisional application No. 60/742,826, filed on Dec. 6, 2005, provisional application No. 60/757,694, filed on Jan. 10, 2006.

(51) Int. Cl.
*A61B 17/128* (2006.01)
*A61B 17/04* (2006.01)
(Continued)

(52) U.S. Cl.
CPC ......... *A61B 17/0469* (2013.01); *A61B 17/0487* (2013.01); *A61B 17/1204* (2013.01); *A61B 2017/22054* (2013.01); *A61B 17/12136* (2013.01); *A61B 17/12099* (2013.01); *A61B 17/12022* (2013.01); *A61B 17/12131* (2013.01);
(Continued)

(58) Field of Classification Search
USPC ............ 606/139, 144–148, 1, 142, 151, 153; 128/898; 112/169
See application file for complete search history.

(56) References Cited

U.S. PATENT DOCUMENTS 4,553,544 A * 11/1985 Nomoto et al. ............... 606/145
4,803,985 A 2/1989 Hill
(Continued)

FOREIGN PATENT DOCUMENTS

JP 2003-533319 A 11/2003
WO WO 02/062200 8/2002
(Continued)

OTHER PUBLICATIONS

EP search report for EP 06840122.3 dated Apr. 15, 2009.
(Continued)

*Primary Examiner* — Mark Mashack
(74) *Attorney, Agent, or Firm* — Woodard, Emhardt, Moriarty McNett & Henry LLP

(57) ABSTRACT

A surgical system for performing gastrointestinal procedures is disclosed. The system includes an elongated body defining an endoscope lumen. The body is adapted to be inserted into the esophagus with a proximal end extending from a body orifice. A working member includes at least one side disposed suction cavity and a cutting device configured to excise a surface layer from the tissue that is captured in the suction cavity. One or more needles are also provided in the working portion, which can be used to apply suture to the captured tissue and/or to inject fluid into the captured tissue prior to excision. Particular applications may be to treat Barrett's esophagus, to treat GERD, or for performing gastroplasty in the stomach.

24 Claims, 45 Drawing Sheets

(51) Int. Cl.
*A61B 17/12* (2006.01)
*A61B 17/062* (2006.01)
A61B 17/22 (2006.01)
A61B 17/00 (2006.01)
A61B 17/06 (2006.01)
A61B 17/30 (2006.01)

(52) U.S. Cl.
CPC ............... *A61B 2017/22071* (2013.01); *A61B 2017/00827* (2013.01); *A61B 17/0625* (2013.01); *A61B 2017/06076* (2013.01); *A61B 2017/306* (2013.01); *A61B 17/0482* (2013.01)
USPC .......................... 606/144; 606/139; 606/148

(56) References Cited

U.S. PATENT DOCUMENTS

| | | | |
|---|---|---|---|
| 4,841,888 | A | 6/1989 | Mills et al. |
| 4,927,428 | A | 5/1990 | Richards |
| 5,037,021 | A | 8/1991 | Mills et al. |
| 5,080,663 | A | 1/1992 | Mills et al. |
| 5,152,769 | A * | 10/1992 | Baber ........................... 606/145 |
| 5,437,681 | A | 8/1995 | Meade et al. |
| 5,540,705 | A * | 7/1996 | Meade et al. ................. 606/145 |
| 5,545,148 | A * | 8/1996 | Wurster ........................ 604/223 |
| 5,643,293 | A | 7/1997 | Kogasaka et al. |
| 5,755,730 | A | 5/1998 | Swain et al. |
| 5,792,153 | A | 8/1998 | Swain et al. |
| 5,908,429 | A * | 6/1999 | Yoon .............................. 606/144 |
| 5,947,983 | A * | 9/1999 | Solar et al. .................... 606/144 |
| 5,972,153 | A | 10/1999 | Focke et al. |
| 6,071,289 | A * | 6/2000 | Stefanchik et al. ........... 606/147 |
| 6,443,962 | B1 * | 9/2002 | Gaber ........................... 606/144 |
| 6,494,888 | B1 | 12/2002 | Laufer et al. |
| 6,506,196 | B1 | 1/2003 | Laufer |
| 6,543,456 | B1 | 4/2003 | Freeman |
| 6,558,400 | B2 | 5/2003 | Deem et al. |
| 6,572,629 | B2 | 6/2003 | Kalloo et al. |
| 6,592,593 | B1 | 7/2003 | Parodi et al. |
| 6,656,194 | B1 | 12/2003 | Gannoe et al. |
| 6,663,639 | B1 | 12/2003 | Laufer et al. |
| 6,719,763 | B2 | 4/2004 | Chung et al. |
| 6,746,460 | B2 | 6/2004 | Gannoe et al. |
| 6,755,843 | B2 | 6/2004 | Chung et al. |
| 6,773,440 | B2 | 8/2004 | Gannoe et al. |
| 6,773,441 | B1 | 8/2004 | Laufer et al. |
| 6,800,081 | B2 | 10/2004 | Parodi |
| 6,821,285 | B2 | 11/2004 | Laufer et al. |
| 6,835,200 | B2 | 12/2004 | Luafer et al. |
| 6,923,819 | B2 | 8/2005 | Meade et al. |
| 7,083,629 | B2 * | 8/2006 | Weller et al. ................. 606/151 |
| 7,261,722 | B2 * | 8/2007 | McGuckin et al. ........... 606/139 |
| 8,105,351 | B2 | 1/2012 | Lehman et al. |
| 8,257,324 | B2 * | 9/2012 | Prausnitz et al. ............. 604/272 |
| 8,469,973 | B2 * | 6/2013 | Meade et al. ................. 606/144 |
| 2002/0055757 | A1 | 5/2002 | Torre et al. |
| 2002/0193809 | A1 * | 12/2002 | Meade et al. ................. 606/144 |
| 2002/0193816 | A1 | 12/2002 | Laufer et al. |
| 2003/0065359 | A1 | 4/2003 | Weller et al. |
| 2003/0083674 | A1 * | 5/2003 | Gibbens, III .................. 606/144 |
| 2003/0120289 | A1 * | 6/2003 | McGuckin et al. ........... 606/151 |
| 2003/0139752 | A1 | 7/2003 | Parsricha et al. |
| 2003/0181924 | A1 | 9/2003 | Yamamoto et al. |
| 2003/0208209 | A1 * | 11/2003 | Gambale et al. ............. 606/144 |
| 2003/0216613 | A1 | 11/2003 | Suzuki et al. |
| 2003/0216749 | A1 | 11/2003 | Ishikawa et al. |
| 2003/0236535 | A1 | 12/2003 | Onuki et al. |
| 2004/0034371 | A1 * | 2/2004 | Lehman et al. ............... 606/144 |
| 2004/0044353 | A1 | 3/2004 | Gannoe |
| 2004/0044354 | A1 | 3/2004 | Gannoe et al. |
| 2004/0044357 | A1 | 3/2004 | Gannoe et al. |
| 2004/0054347 | A1 | 3/2004 | Zadno-Azizi |
| 2004/0082963 | A1 | 4/2004 | Gannoe et al. |
| 2004/0087996 | A1 | 5/2004 | Gambale et al. |
| 2004/0092892 | A1 | 5/2004 | Kagan |
| 2004/0092965 | A1 | 5/2004 | Parihar |
| 2004/0092974 | A1 | 5/2004 | Gannoe et al. |
| 2004/0138682 | A1 | 7/2004 | Onuki et al. |
| 2004/0147941 | A1 | 7/2004 | Takemoto et al. |
| 2004/0158125 | A1 * | 8/2004 | Aznoian et al. .............. 600/106 |
| 2004/0167546 | A1 | 8/2004 | Saadat et al. |
| 2004/0193117 | A1 | 9/2004 | Laufer et al. |
| 2004/0193184 | A1 | 9/2004 | Laufer et al. |
| 2004/0193193 | A1 | 9/2004 | Laufer et al. |
| 2004/0193194 | A1 | 9/2004 | Laufer et al. |
| 2004/0194790 | A1 | 10/2004 | Laufer et al. |
| 2004/0210243 | A1 | 10/2004 | Gannoe et al. |
| 2004/0225191 | A1 | 11/2004 | Sekine et al. |
| 2004/0249395 | A1 | 12/2004 | Mikkaichi et al. |
| 2005/0004431 | A1 | 1/2005 | Kogasaka et al. |
| 2005/0015101 | A1 * | 1/2005 | Gibbens et al. .............. 606/144 |
| 2005/0033325 | A1 | 2/2005 | May et al. |
| 2005/0033328 | A1 | 2/2005 | Laufer et al. |
| 2005/0049455 | A1 | 3/2005 | Ootawara et al. |
| 2005/0049614 | A1 | 3/2005 | Cendan |
| 2005/0049617 | A1 | 3/2005 | Chatlynne et al. |
| 2005/0055038 | A1 * | 3/2005 | Kelleher et al. .............. 606/151 |
| 2005/0065483 | A1 | 3/2005 | Nakao |
| 2005/0080438 | A1 | 4/2005 | Weller et al. |
| 2005/0090862 | A1 | 4/2005 | McDevitt et al. |
| 2005/0096673 | A1 * | 5/2005 | Stack et al. ................... 606/151 |
| 2005/0096750 | A1 | 5/2005 | Kagan et al. |
| 2005/0113869 | A1 | 5/2005 | Price |
| 2005/0149067 | A1 | 7/2005 | Takemoto et al. |
| 2005/0165419 | A1 | 7/2005 | Sauer |
| 2005/0177176 | A1 | 8/2005 | Gerbi et al. |
| 2005/0192599 | A1 | 9/2005 | Demarais |
| 2005/0192601 | A1 | 9/2005 | Demarais |
| 2005/0192615 | A1 | 9/2005 | Torre et al. |
| 2005/0203488 | A1 | 9/2005 | Michlitsch et al. |
| 2005/0203500 | A1 | 9/2005 | Saadat et al. |
| 2005/0203547 | A1 | 9/2005 | Weller et al. |
| 2005/0203548 | A1 | 9/2005 | Weller et al. |
| 2005/0209612 | A1 | 9/2005 | Nakao |
| 2005/0216040 | A1 | 9/2005 | Gertner |
| 2005/0251153 | A1 | 11/2005 | Sakamoto et al. |
| 2005/0251175 | A1 | 11/2005 | Weisenburgh et al. |
| 2006/0069396 | A1 * | 3/2006 | Meade et al. ................. 606/144 |
| 2006/0282089 | A1 * | 12/2006 | Stokes et al. ................. 606/144 |
| 2007/0055292 | A1 * | 3/2007 | Ortiz et al. ................... 606/139 |

FOREIGN PATENT DOCUMENTS

| | | |
|---|---|---|
| WO | WO 2004/103157 | 12/2004 |
| WO | WO 2005/011463 | 2/2005 |
| WO | WO 2005/020802 | 3/2005 |
| WO | WO 2005/086945 A | 9/2005 |

OTHER PUBLICATIONS

International Search Report for PCT/US06/61665.
Japan Application No. P2013-058687 Notice of Reasons for Rejection mailed Mar. 18, 2014.

* cited by examiner

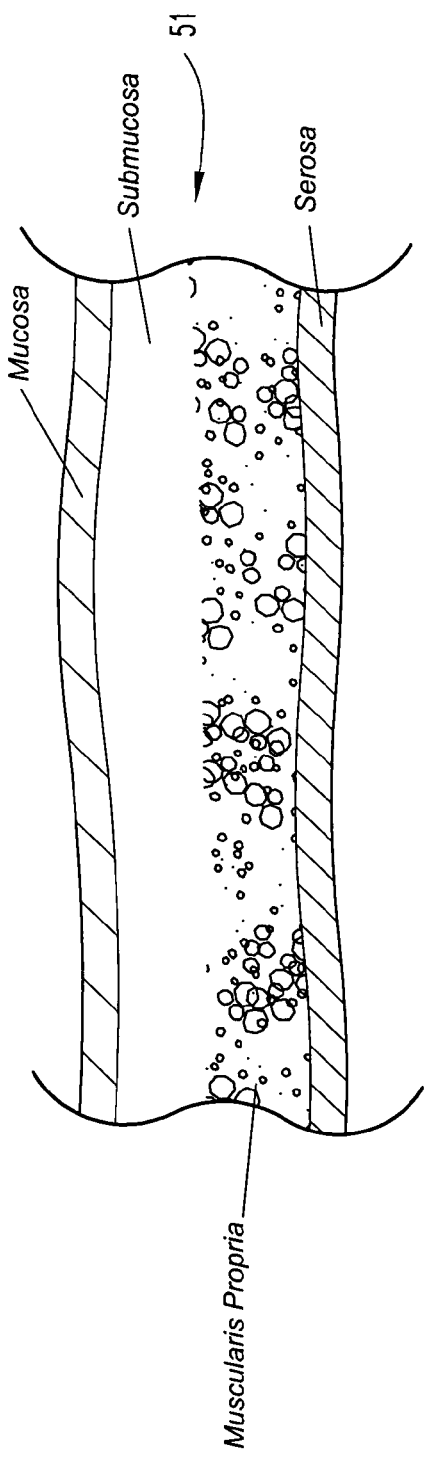
Fig. 9
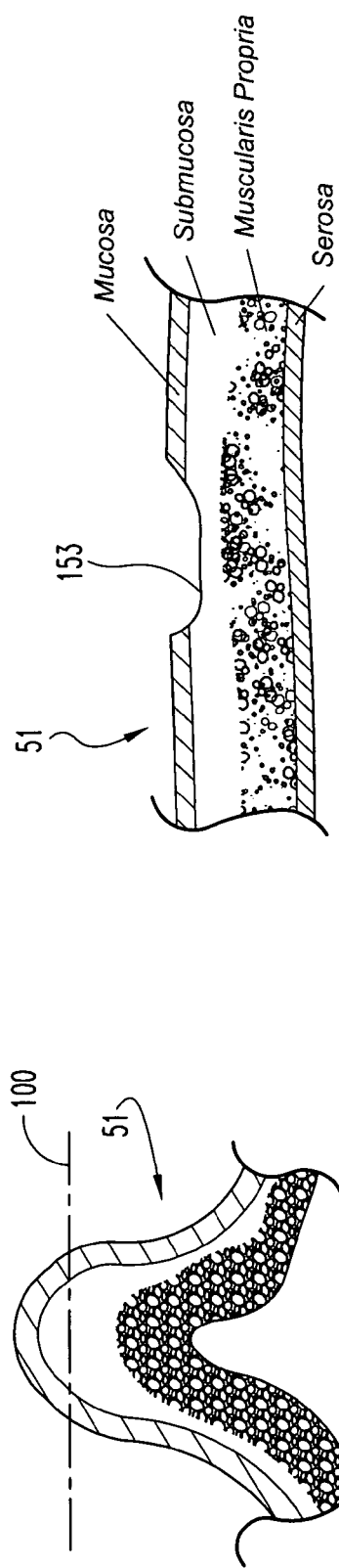
Fig. 11
Fig. 10

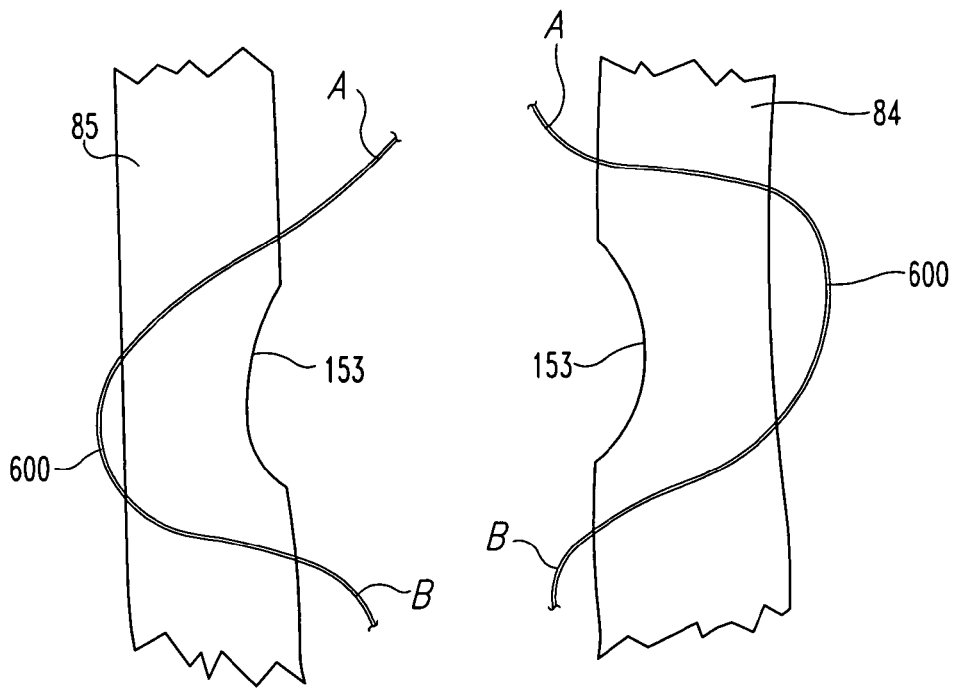
Fig. 32
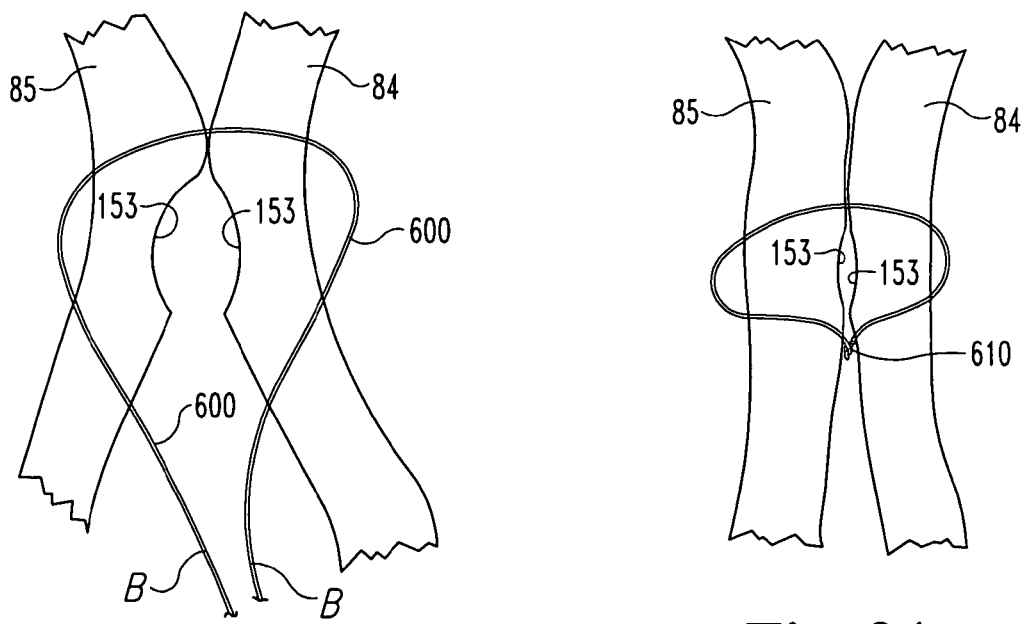
Fig. 33
Fig. 34

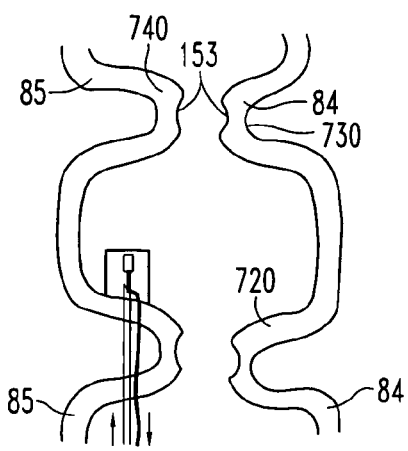
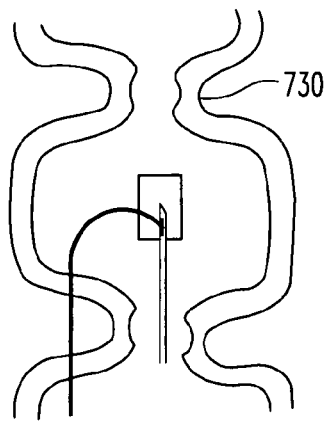
Fig. 35A	Fig. 35B
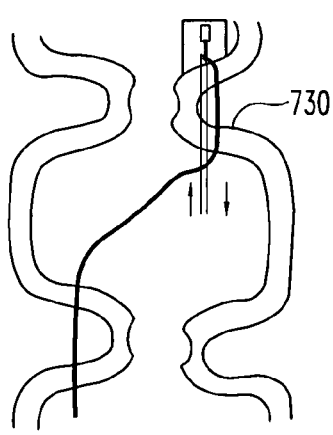
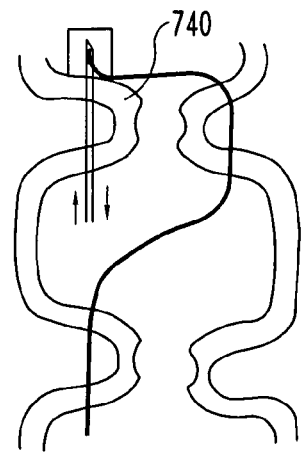
Fig. 35C	Fig. 35D
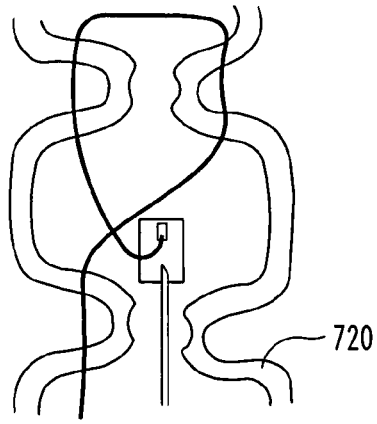
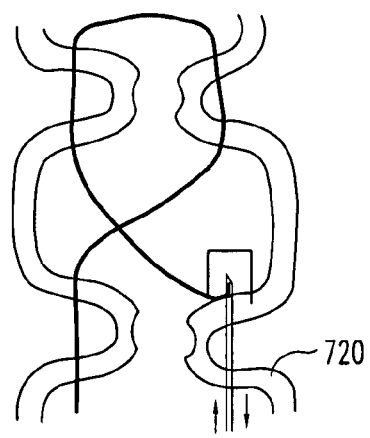
Fig. 35E	Fig. 35F

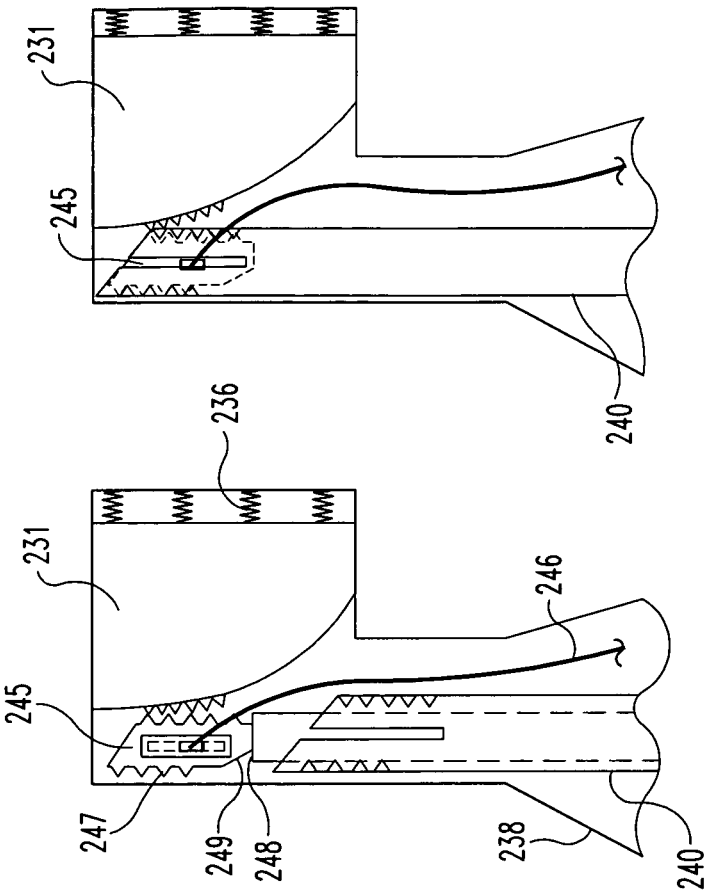
Fig. 54
Fig. 53
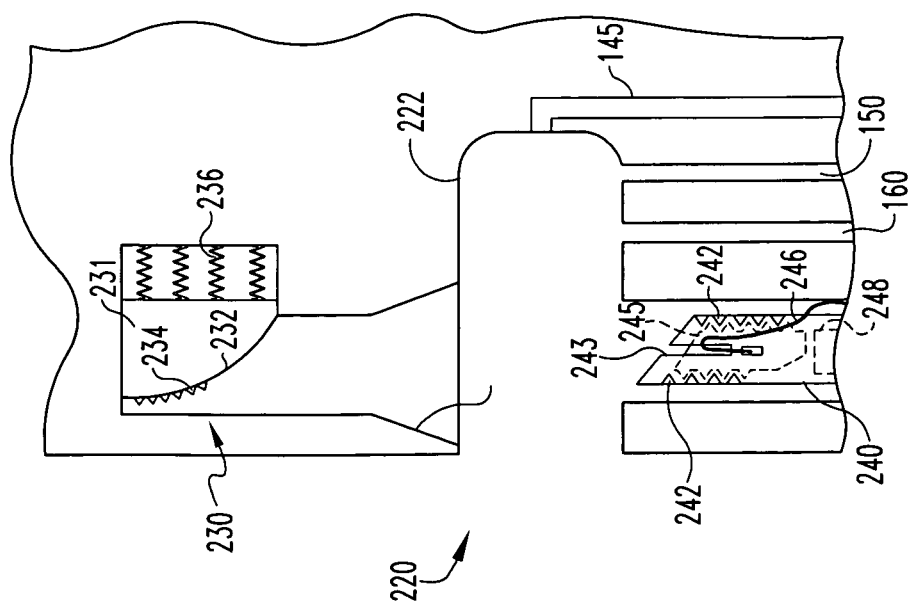
Fig. 52

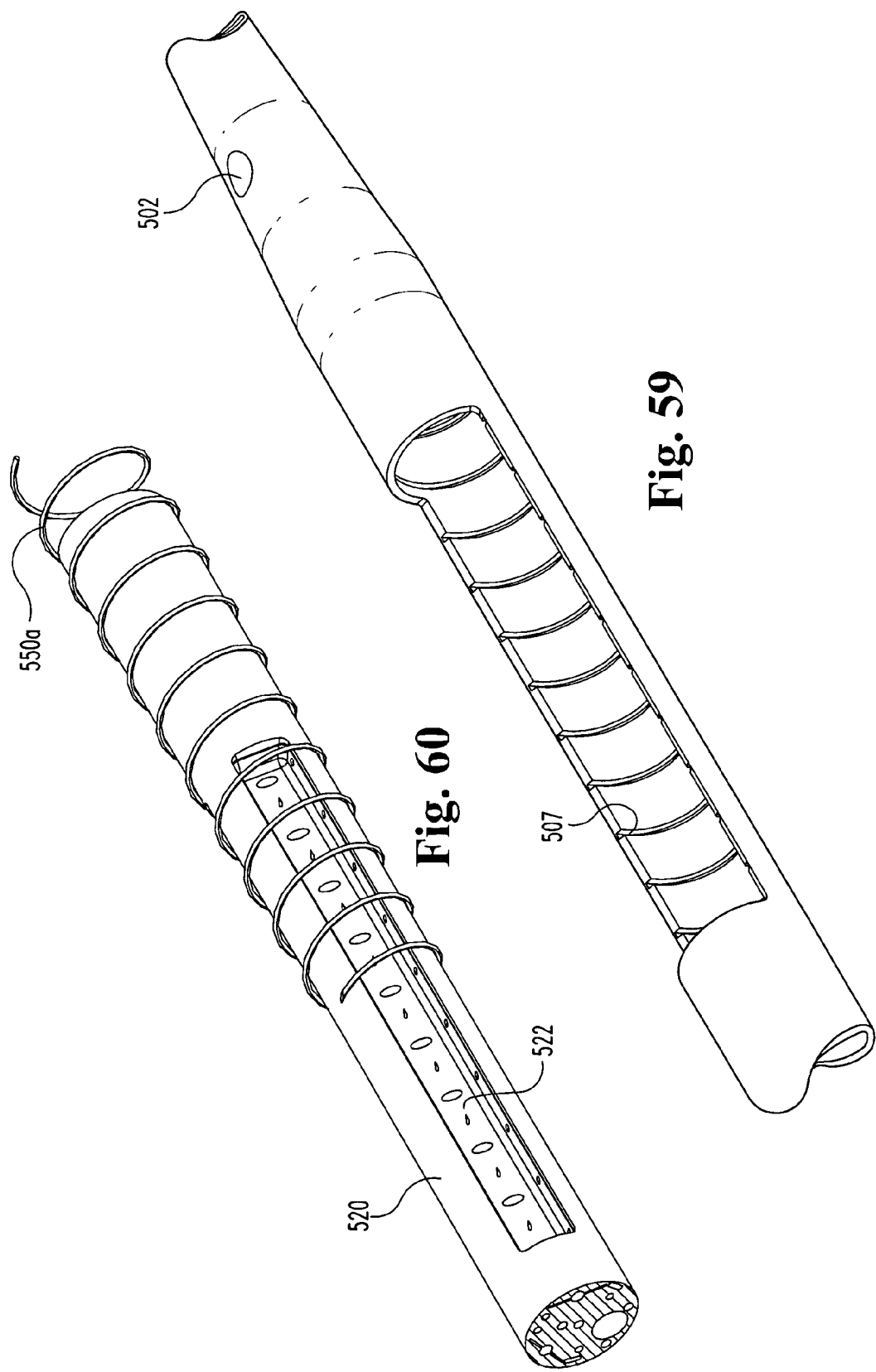

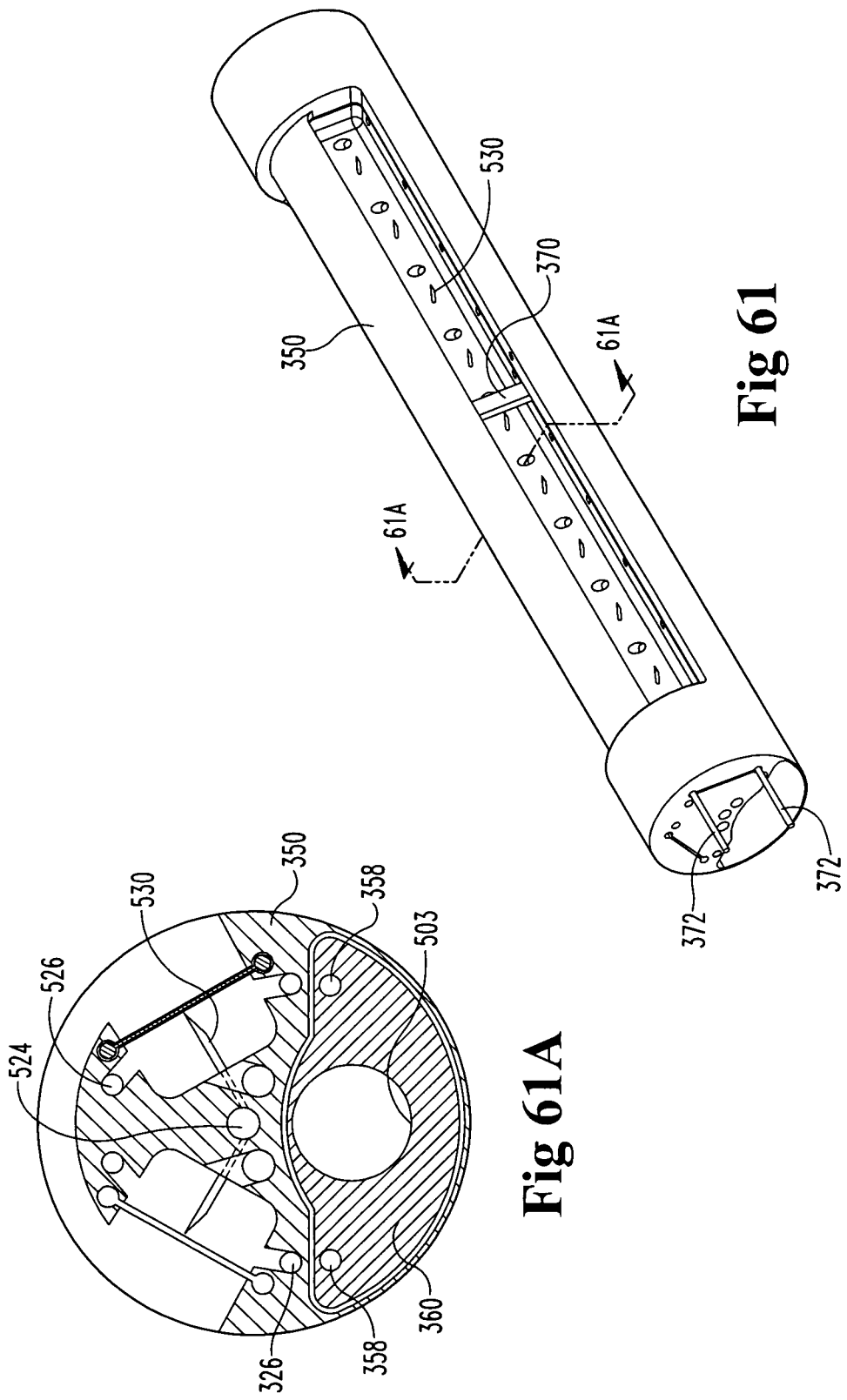

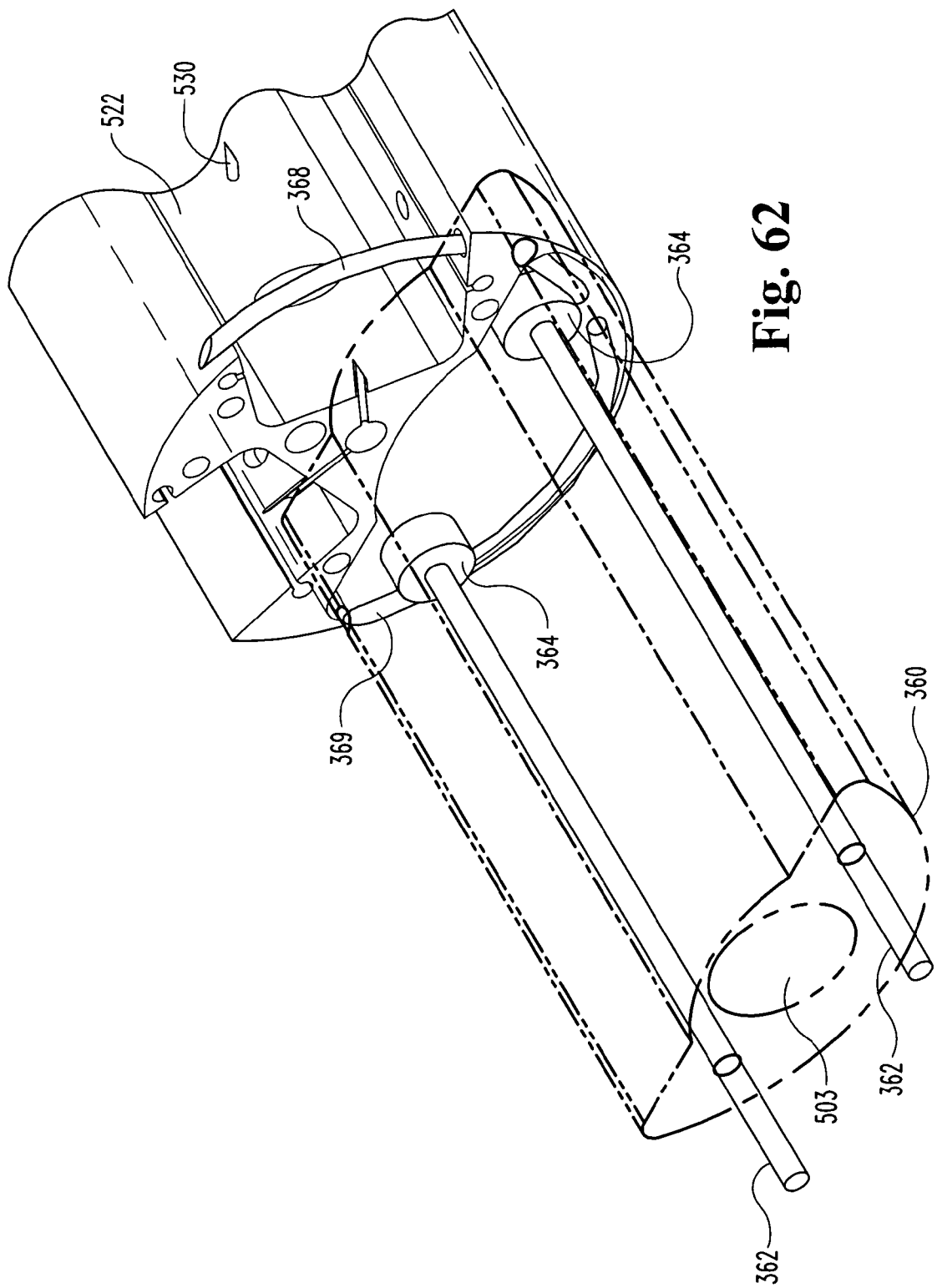

SYSTEMS AND TECHNIQUES FOR MINIMALLY INVASIVE GASTROINTESTINAL PROCEDURES

RELATED APPLICATION DATA

This application is a continuation of PCT/US2006/61665, filed Dec. 6, 2006, which is a continuation in part of application Ser. No. 11/457,442, filed Jul. 13, 2006 and issued as U.S. Pat. No. 8,641,729, which claims the benefit of Provisional Application Nos. 60/698,748 filed Jul. 13, 2005, 60/742,826 filed Dec. 6, 2005, and 60/757,694 filed Jan. 10, 2006.

BACKGROUND

The present invention relates generally to gastrointestinal procedures such as bariatric surgery. More particularly, but not exclusively, it relates to surgical devices and techniques for excising mucosa in the stomach or esophagus and/or for securing portions of the stomach and esophagus together, e.g. to reduce the size of the stomach in connection with the treatment obesity in humans.

Gastric reduction surgery is conventionally performed to restrict food intake of a patient by decreasing the size of the stomach. The objective is to limit the receptive capacity of the stomach and promote weight loss in patients with severe obesity. Various surgical techniques have been developed, such as laparoscopic banding, where a device is used to constrict a portion of the stomach, vertical banded gastroplasty (VBG), or the more invasive Roux-en-Y Gastric Bypass which effects a permanent reduction in the volume of the stomach. It is desirable to develop surgical instruments and techniques that can be used to achieve gastric reduction in a minimally invasive manner. The present invention is generally directed to addressing this need, but aspects of the invention can be usefully applied in other endoscopic procedures, for example in the diagnosis or treatment of Barrett's esophagus and in the treatment of gastoresophegael reflex disease (GERD).

SUMMARY

A novel approach to gastroplasty and other medical procedures has been developed. In a preferred form, this approach can be used to achieve a reduction in the size of the stomach without the need for any external surgical incisions. A useful surgical system for implementing this approach can be a single device or a combination of devices working together which includes a main elongated body adapted to be transorally inserted into a patient's stomach. The body has a smooth outer surface and is preferably shaped similar to a conventional dilator or bougie for ease of insertion into the patient's stomach. When used to create a lumen in the patient's stomach, the outer diameter of the device may be chosen based on the size of the gastric lumen to be created, with a larger diameter device being used to create larger diameter gastric lumens. Alternatively the device may be provided with a spacing balloon along its length so as to be able to enlarge the effective outer diameter of a desired section after the device has been inserted into the stomach.

The device may have a distal anchoring section, and at least one suturing section may be provided along the length of the body proximal to the anchoring section. In use, the elongated body may be positioned along the lesser curvature of the stomach with the distal section used to anchor the device. One purpose of anchoring the device is to provide secure positioning for the suturing section as it is used to attach sutures to the anterior and posterior stomach walls. Anchoring of the distal section also facilitates modifying the shape of the device while it is in the stomach, for example to cause the device to assume a predetermined shape or orientation. With the device securely in position, opposed sutures are attached to the stomach walls and then drawn together to attach the anterior and posterior walls to form a partition or lumen in the stomach. Certain gastroplasty approaches may forgo anchoring of the device, and operations on the esophagus or esophageal junction (e.g. treating Barrett's esophagus or forming tissue plications to treat GERD) may anchor in a different location, if at all.

In one form, anchoring is accomplished at least in part by lodging the distal section through the pyloric sphincter and into the first portion of the duodenum. In another form, the distal portion of the device is not itself lodged or otherwise anchored in the patient's digestive tract, but rather it is engaged with a separate device that is lodged or otherwise anchored therein. A separate anchoring balloon at the distal end of a balloon catheter may be used for this purpose. The separate anchoring balloon may be preinserted into position (e.g. via the working channel of an endoscope) with its catheter extending proximally into the stomach and out the esophagus. After the anchoring balloon is inserted into position, inflated, and then the insertion endoscope removed, the distal end of the device may be inserted over the distal end of the catheter and guided into position in the stomach. With the catheter in a lumen of the device, application of tension to the catheter may be used to bias the device into a desired orientation or position (e.g. press it against the lesser curvature). Alternatively or in addition, the device may be clamped or otherwise releasably affixed to the catheter.

Alternatively or in addition to its uses of guiding the device during insertion and/or anchoring the device during application of the sutures, the anchoring balloon may be used to test for leaks during or after creation of the gastric lumen. When used for leak checking, the balloon is positioned (or repositioned) to plug the distal end of the lumen to be tested. With the balloon plugging the distal end, a testing fluid (such as methlyene blue) may be injected into the lumen with the presence of leaks being checked, for example, via endoscopic visualization.

The balloon catheter may be sized to fit through the working channel of the endoscope (e.g. 5 mm), and the distal end of the balloon catheter is preferably constructed to facilitate the insertion and removal of instruments from it (e.g. the endoscope used for insertion and the keeper). To accomplish this, valves and any actuating mechanism(s) may be removably coupled at the distal end so that they can be removed to reduce the effective diameter of the distal end to less than, e.g. 5 mm, so as to accommodate the insertion and removal of devices. In one form, the distal end is provided with a self closing valve. The self closing valve may be constructed such that when a fluid injection device is coupled to the valve, fluid communication with the balloon is established; and when the injection device is uncoupled from the valve, fluid communication with the balloon is interrupted (e.g. to keep the balloon inflated without external fluid pressure application). A suitable self closing valve includes a deformable material that allows a hollow needle to pass and closes when the needle is removed.

In a typical configuration, the suturing section(s) will include a side disposed suction cavity constructed to capture a fold of tissue suitable for receiving at least one suture, preferably a series of sutures. The suturing section will also include a puncturing member, such as a needle, that is operative to place a suture through at least one fold of tissue that has been captured in the suction cavity, though preferably the suturing section is capable of placing multiple sutures at a series of locations.

In gastroplasty, a general purpose of the surgical system is to provide endoscopic access for the placement of sutures along the anterior and posterior stomach walls in a desired pattern. For a typical procedure, the suture pattern will be such that sutures are positioned in opposing locations along the anterior and posterior stomach walls in such a way that, when the tissue of the suture sites is drawn together with the tissue of an opposing suture site, a seam is formed in the stomach generally extending from near the pylorus to the esophagus. In a typical application, sutures will be placed along complimentary paths on the anterior and posterior walls with the longitudinal axis of the device providing the general orientation of the paths.

To locate sutures along paths generally corresponding to the longitudinal axis of the device, the distal anchoring section may be withdrawn and repositioned, so as to locate the suturing section either closer or further from the esophagus. In order to reduce the number of times such repositioning would be needed, and thus to further speed the procedure, the suturing section(s) can be constructed so as to be operable to apply sutures at several positions along the longitudinal axis of the device (without proximal or distal repositioning or the entire device). In this way, a series of sutures can be placed along the longitudinal axis of the device while the distal section remains anchored in a single position. This can be accomplished by providing several suturing sections at different positions along the length of the device and/or by constructing at least a portion of the suturing section to be translatable relative to the anchoring section, for example by being slidably disposed in a lumen of the elongated body. In one implementation, at least a portion of the suturing section is constructed such that it can be wholly or partially withdrawn from the patient while the elongated body remains in place, facilitating the rapid adjustment, tying, or reloading of sutures during the procedure.

In a preferred form, surgical instrumentation includes an outer elongated body, or keeper, that is guided into location (i.e. into the stomach via the catheter on an anchoring balloon). The keeper includes one or more working lumens leading to a window section that is positioned in the patient's stomach. The window section provides access to the stomach walls for the elements needed during the particular procedure. If the objective of the procedure is to perform tissue resection under endoscopic visualization, such as may be employed in the diagnosis or treatment of Barrett's esophagus, only a tissue capture and excision device (described below) need be provided through the working lumen to the window to capture, for example, esophageal tissue for later biopsy. For gastroplasty and formation of tissue plications to treat GERD, both a tissue capture and excision device and a suture activating mechanism would typically be employed. These elements may be integrally or separately provided.

In one design for gastroplasty, the keeper has a main elongated body and the working components are configured to have a pair of elongated suction cavities in side by side arrangement for capturing a line of tissue in each cavity, the lines being from the anterior and posterior stomach walls respectively. Sutures are then applied between the captured tissue lines such that, once the tissue is released from the suction cavities, the sutures may be drawn tight to draw the anterior and posterior stomach walls together. A curved needle follows a helical or corkscrew shaped path through the device, with the axis of the helix generally corresponding to the elongated axis of the device, may be used to apply sutures between the captured tissue lines. One or more rollers may be used to drive the needle along its helical/corkscrew path, and the needle and/or the rollers may have teeth for enhancing the engagement therebetween.

In another design for gastroplasty, the keeper has a main elongated body and the working components are configured to have an elongated suction cavity for capturing a line of tissue from one stomach wall (e.g. from the anterior or the posterior wall). A series of curved needles are employed to apply sutures to the captured tissue, the tissue is released, and then the process is repeated at the other stomach wall. Free ends of the sutures applied at each stage may be organized outside the body (e.g. with a numbered plastic plate) and appropriate ones secured together to bring the anterior and posterior walls into apposition (e.g. via knots or knotting elements slid down the free ends). The needles may operate generally perpendicular to the longitudinal axis of the device, and they may be operated in a variety of different ways such as via rollers (e.g. with teeth on the roller and on the needles) or via a shuttle driven by pull wires. The novel techniques for driving needles described herein may be employed to advantage in other types of minimally invasive surgical situations (e.g. endoscopic or laparoscopic procedures) where precise manipulation of a needle at a location remote from the operator's hands is desired.

As an aid for positioning and orientation, the elongated body or keeper may be configured to receive one or more orientation wires or shape memory rods in one or more orientation wire lumens. These orientation wires may be used to establish a desired curvature or positioning of the elongated body (for example positioning it against the lesser curvature of the stomach). Alternatively or in addition, the orientation wire may be used to provide flexion orientation for the suturing section, for example to selectively dispose the suturing section near the lesser curvature. A mechanism for accomplishing rotational orientation via an orientation wire may be by providing two orientation wire lumens, each offset from the centerline of the body. Positioning of the orientation wire in the first orientation wire lumen may be used to flex/bend the device along the lesser curvature for anterior suture placement, with the second used to flex/bend the device for posterior suture placement.

Prior to drawing the anterior and posterior stomach walls together (to form the seam), it is desirable to prepare the tissue sections to be joined so as to promote their adhesion. One method of tissue preparation is to cauterize or abrade one or both of the tissue surfaces to be joined. The surgical system can be configured with a separate cautery or abrading device used for this purpose, or a cautery or abrading surface may be provided adjacent and/or inside the suction cavity of the suturing section, to cauterize or abrade the tissue in connection with the suturing. Such cautery or abrading techniques are described in U.S. 2004/0034371 in the context of the treatment of GERD and these techniques may be beneficially used in the present procedure.

An alternative technique for preparing the tissue to be joined so as to promote adhesion has also been developed. This technique is based on tissue removal, for example sectioning or slicing a thin layer of tissue to expose the submucosa of the stomach wall, and it is believed that this approach is superior to the mere modification of existing tissue in the cauterizing or abrading of the mucosa described in U.S. 2004/0034371. More specifically, it is expected that by exposing the submucosa of the stomach, and by placing areas of exposed submucosa in contact, stomach tissue will heal together and form a secure bond without some of the drawbacks of prior approaches.

A desirable way of exposing submucosa is via a cutting means, such as a blade, a knife, a wire, a loop, or a high frequency snare, that is operable to slice tissue that has been acquired in a suction cavity, such as the suction cavity of the suturing section. Prior to sectioning, the captured tissue may be injected with a preparatory material, such as adrenaline saline solution, via an injection needle. To assist in reliably sectioning the appropriate tissue thickness, the injection needle and/or the suturing needle (when present) may be used to fixate the captured tissue.

While a wide variety of suturing mechanisms and suturing patterns can be employed to join the anterior and posterior stomach walls, the suturing pattern is preferably selected to press together the prepared tissue portions to be joined, rather than tending to close up the individual sections of prepared tissue. For example, four folds of tissue (two opposed pairs) with prepared sections near the fold may be joined with a stitching pattern resembling a FIG. 8.

BRIEF DESCRIPTION OF THE DRAWINGS

FIG. 9 is an illustrative cross section of stomach tissue showing the various layers.

FIG. 10 is a cross section showing a desirable resecting line 100 for preparing a fold of tissue to promote adhesion.

FIG. 11 is the FIG. 10 tissue after resection along line 100.

FIG. 32-34 are side views of two tissue sections being joined.

FIGS. 35A-35F are a series of side views of the joining of 4 tissue folds in a FIG. 8 suture pattern utilizing the needle shuttle concept for bi-directional application of a suture.

FIGS. 52-54 are side views showing the operation of a suturing mechanism using a thread shuttle that is passed back and forth across a suction chamber by a hollow needle.

FIG. 59 corresponds to the keeper as depicted in FIG. 58 with the internal helical needle and the internal tissue capture, excision, and needle activation components removed and shown in FIG. 60.

FIG. 61. is a perspective view of an alternative configuration for the internal tissue capture, excision and needle activation components for use with a FIG. 59 keeper.

FIG. 61A is a sectional view as indicated in FIG. 61 and illustrating needle activation shuttle slideably disposed within the tissue capture and excision component.

FIG. 62 is a schematic illustrating the working arrangement for needle activation via rollers for the slideably disposed shuttle of FIG. 61.

DESCRIPTION OF ILLUSTRATIVE EMBODIMENTS

Figure 1:
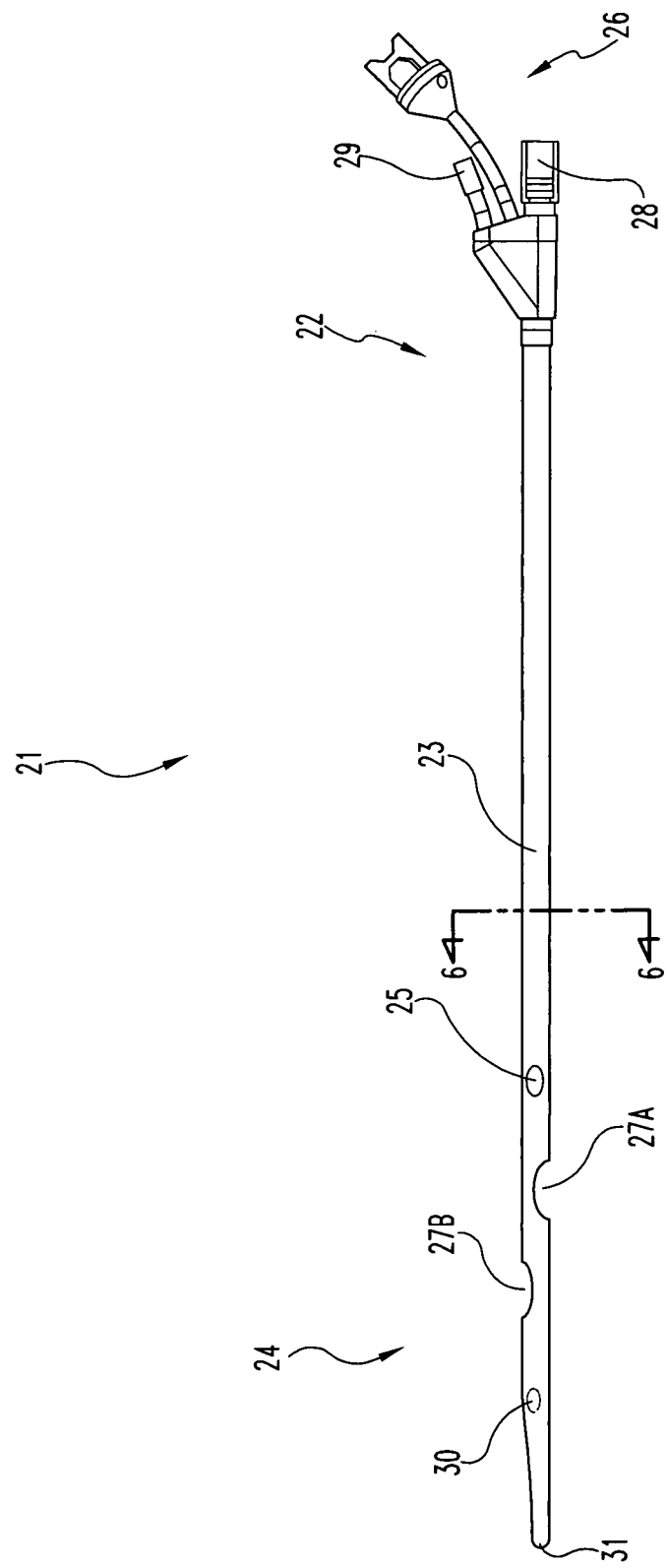
FIG. 1 is a side view of a device according to a first embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

A novel approach to gastroplasty and other medical procedures has been developed. This general approach is described herein with reference to various instruments and devices, some of which have been developed specifically for the implementation of this approach in performing gastric reduction from within the stomach wall via the esophagus. While some of the devices described are particularly adapted to this procedure, it is to be understood that commercially available devices and others known in the art may be adapted and used to advantage in implementing the inventive processes described herein. The provision and use of devices specially adapted to this procedure may, however, facilitate its successful implementation. As will also be appreciated and understood from the disclosure to follow, the instruments and devices developed for the implementation of this approach may also be used to advantage for the conduct of other medical procedures. Thus, those novel instruments and devices are not to be construed as limited to the uses therefore described herein with reference to gastric reduction. For example, the suturing devices described herein may be used in forming tissue plications for the treatment of GERD. Likewise, the needle activation mechanisms described herein may be used in other applications where remote operation of a needle is required.

Devices and techniques for tissue acquisition and fixation, and methods of using them are described. In general, the gastroplasty techniques and devices described herein may be utilized for creating a partition within a hollow body organ, such as the stomach or other portions of the gastrointestinal tract. The gastroplasty devices may be advanced through a variety of methods, i.e. transesophageally (transorally or transnasally) and/or endoscopically to create a gastric lumen within the stomach. Further, the gastroplasty devices may be assisted through the use of laparoscopic or endoscopic visualization to ensure proper operation of the devices.

The gastroplasty techniques and devices described herein allow for the creation of a smaller gastric lumen through a minimally invasive procedure taking place entirely within the stomach cavity. This effectively reduces the time that a patient must be hospitalized and allows the patient to return to work or normal activity sooner. Further, by eliminating the needs for abdominal incisions, the complications that result from the large quantity of fat layers that must be cut through and eventually replaced are prevented.

Turning now to the Figures, FIG. 1 shows a side view of one illustrative embodiment of a device useful in transoral gastroplasty. Device 21 is generally comprised of an elongate flexible tubular member 24 having a control assembly 26 connected at its proximal end 22. Control assembly 26 is illustrated with several structures for controlling the operation of the devices on the distal working portion 24 of member 23. Control assembly 26 may include endoscopic inlet port 28 for the insertion of an endoscope (not shown) to provide visualization. Control assembly 26 may further include vacuum connection 29 for connection of a vacuum source (not shown). Elongate member 24 preferably has a circular or elliptical cross sectional area to create an atraumatic surface during insertion into the body.

Distal portion 24 of member 23 includes a guide wire outlet 30 and guide wire inlet 31 to allow the surgeon to place device 21 over a guidewire which has been preinserted into the patient's gastrointestinal tract. Suturing sections 27A and 27B are provided along member 23 for acquiring and securing apposed tissue once device 21 has been properly positioned. Device 21 further includes endoscopic outlet port 25 to allow the surgeon to position an endoscope outside of device 21 once device 21 has been positioned within a hollow organ to provide visualization of the surgical procedure.

Figure 2:
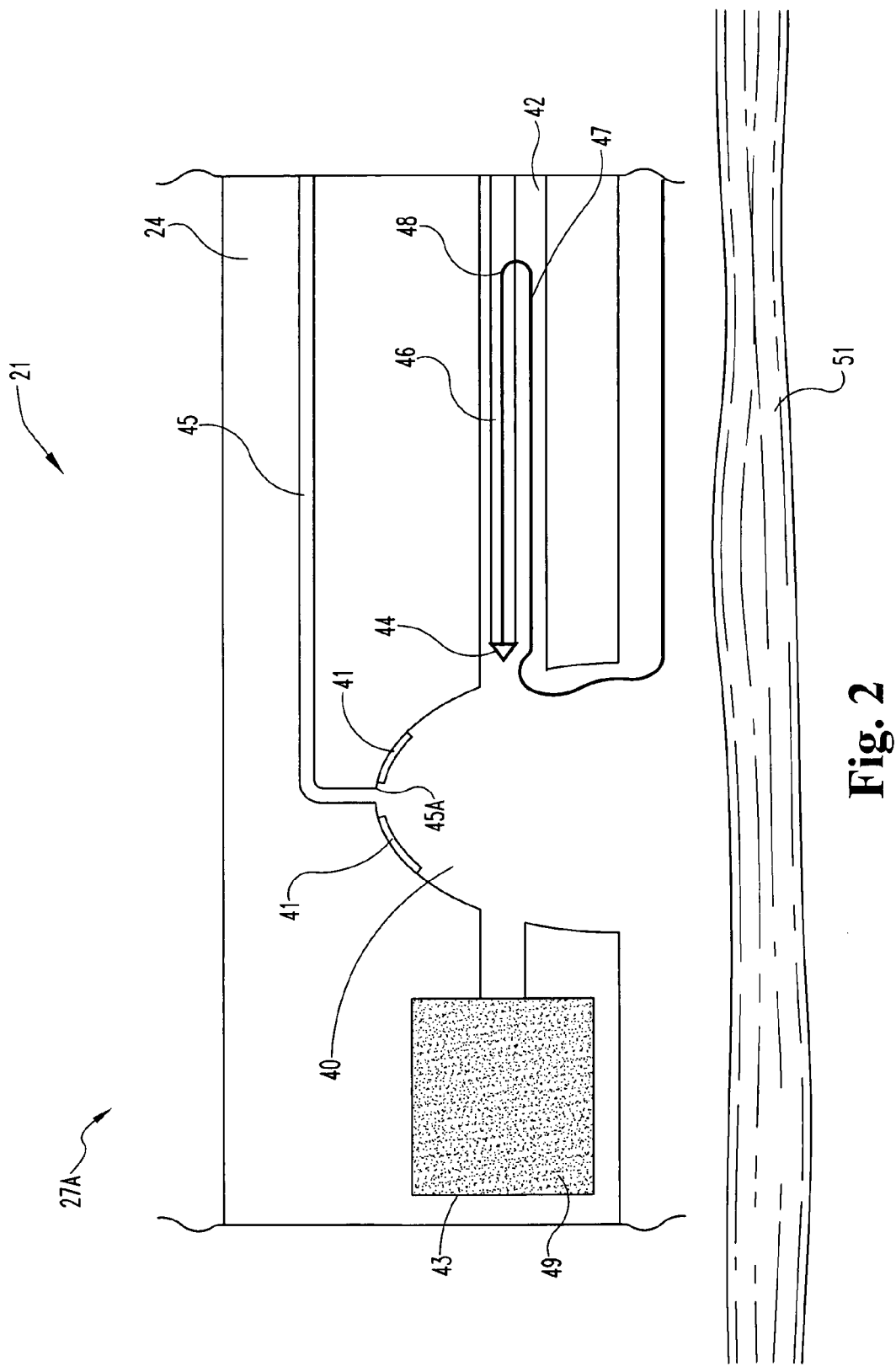
FIGS. 2-5 are partial sectional views of the suturing section of the first embodiment during operation.

FIG. 2 is a schematic showing details of the suturing section 27A. It will be understood that suturing section 27B is similar to section 27A, the difference being their relative positions on the device. A suction chamber 40 is recessed into elongate member 23 of device 21. Cautery surfaces 41 are disposed within suction chamber 40 on either side of a vacuum port 45A. The cautery surfaces 41 are heating elements coupled to electrical lines (not shown), and they are used to cause slight trauma to the external layer of the tissue which is suctioned into chamber 40 by a vacuum supplied by vacuum line 45.

Also included adjacent to chamber 40, in longitudinal alignment on opposing sides of chamber 40, are needle lumen 42 and entrapment chamber 43. Needle lumen 42 contains a needle head 44 mounted to needle pusher rod 46 which is oriented longitudinally such that the tip of needle head 44 is aligned with the proximal wall of suction chamber 40. Optionally, an adhesion surface may exist between needle head 44 and pusher rod 46 to ensure that needle head 44 remains in place during insertion of device 21 and articulation of elongate member 23. Attached to needle head 44 there is a suture 47. Suture 47 could be a 2-0 or 0 monofilament suture, or other suitable suture material, such as silk thread or polypropylene (e.g. PROLENE suture, marketed by Ethicon, Cincinnati Ohio). Suture 47 can reside in a longitudinal guide groove 48 of pusher rod 46.

Figure 3:
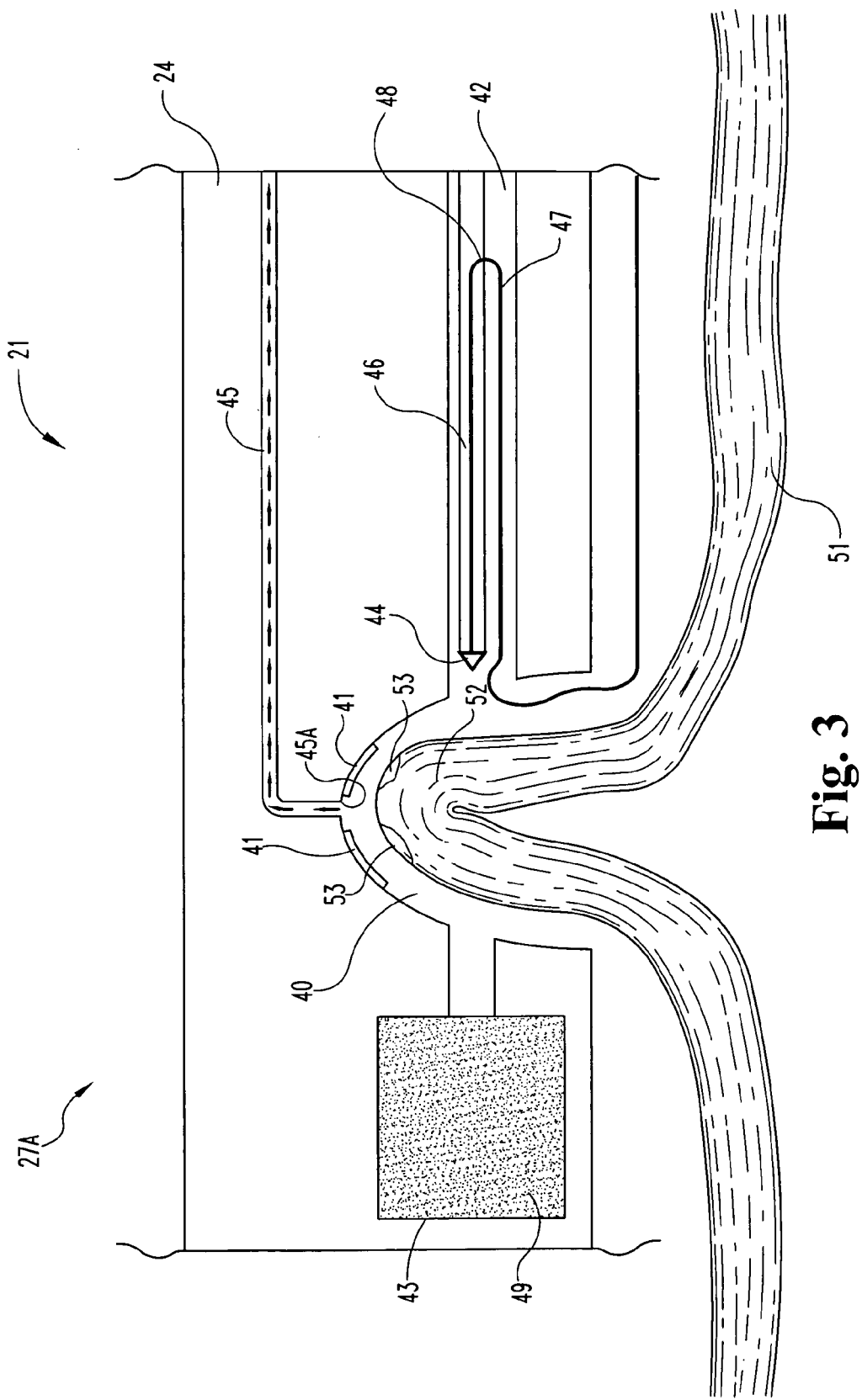
Figure 4:
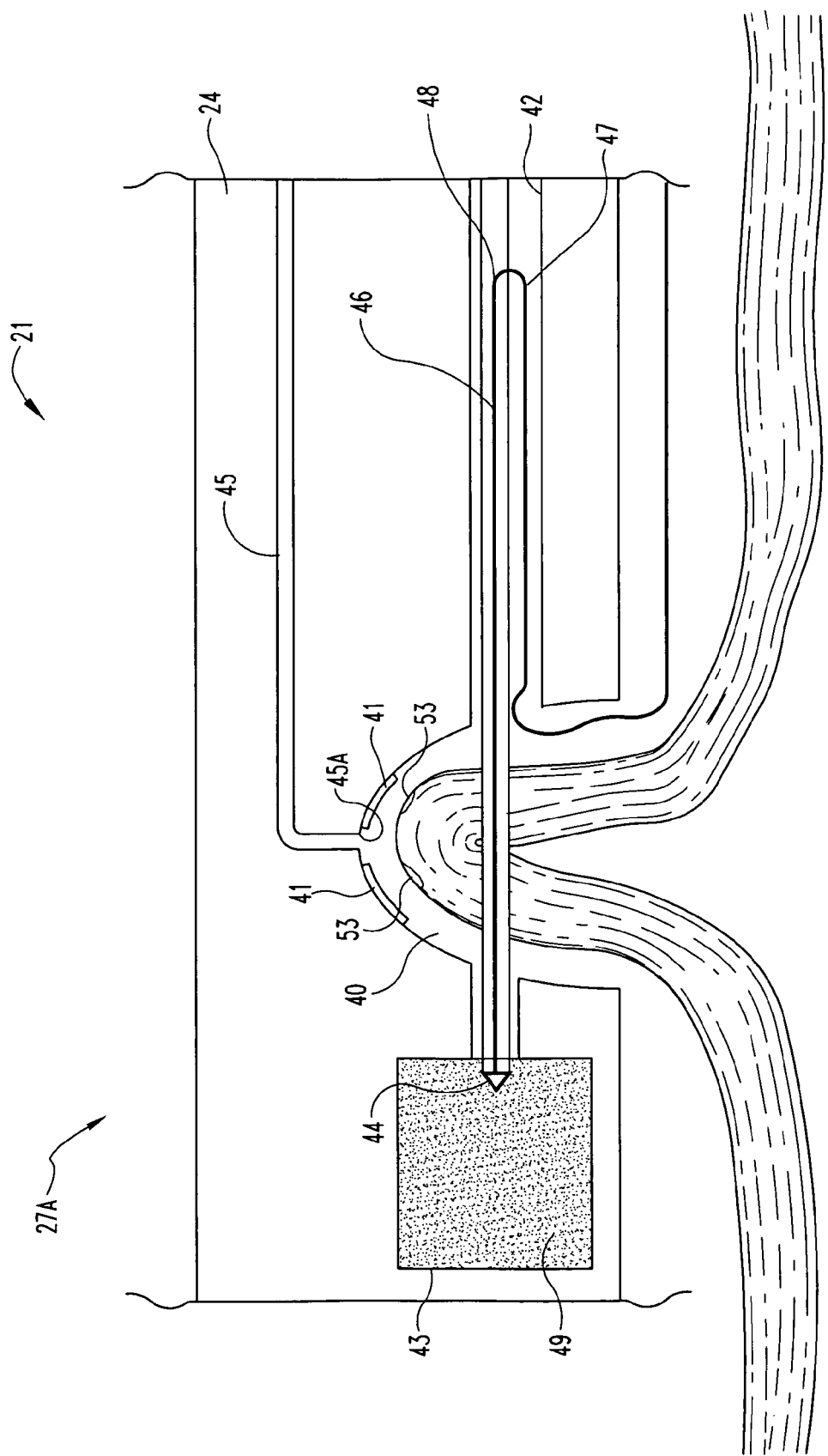

Referring to FIG. 3, suturing section 27A includes a side disposed suction chamber 40 for tissue acquisition. Vacuum line 45 is connected to an external vacuum source through port 29 and applies sufficient suction to draw a fold 52 of tissue 51 into suction chamber 40. Once the tissue fold is acquired, cautery surfaces 41 are activated to cauterize the tissue and create cauterized areas 53 of tissue on fold 52. These cauterized areas 53 are designed to promote subsequent tissue adhesion. This approach to promoting tissue adhesion is analogous to the techniques described in the context of a surgical treatment for GERD in U.S. application Ser. No. 10/275,521 (U.S. 2004/0034371) titled "Method of Promoting Tissue Adhesion" and naming the present inventor as a co-inventor, which is incorporated by reference to the extent not inconsistent with the present disclosure Referring to FIG. 4, with the fold 52 of tissue 51 still held in place within chamber 40 by the suction force, pusher rod 46 longitudinally projects needle 44 through suction chamber 40 and the contained tissue fold 52 and into entrapment chamber 43. Once there, the acquisition material 49 within entrapment chamber 43 holds needle head 44 as well as the attached suture 47 on the opposite side of the chamber 40.

Figure 5:
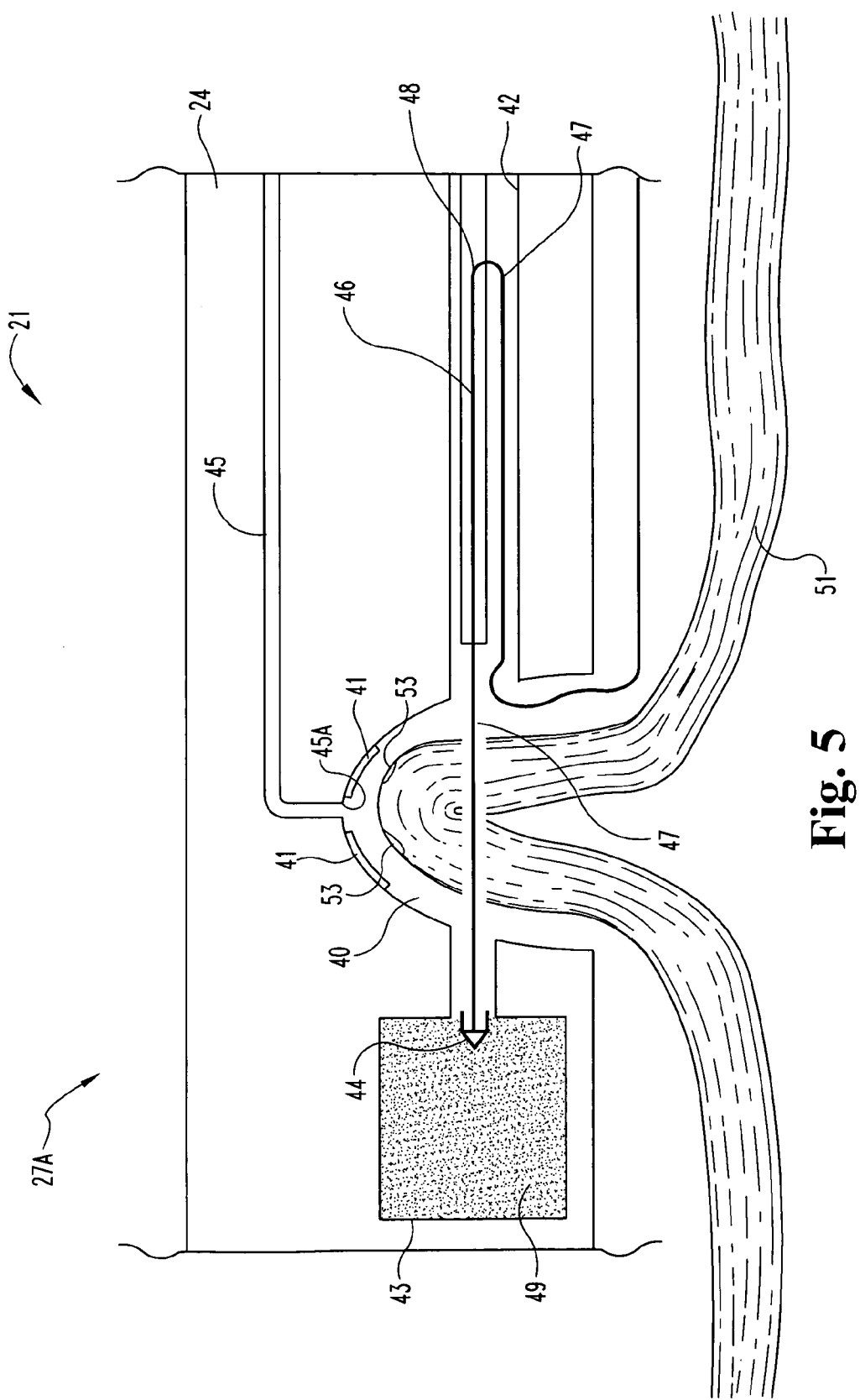

Referring now to FIG. 5, the pusher rod 46 is next extracted from the tissue fold 52 and drawn back into the needle chamber 42. The result is that suture 47 has been passed through tissue fold 52. The entire apparatus 21 may then be withdrawn from the patient and the surgeon may acquire the distal end of suture 47 by removing needle head 44 from entrapment material 49. Having maintained control over the proximal end of suture 47 throughout the procedure, the surgeon will now have both ends of a suture that has been attached to the interior stomach wall.

Figure 6:
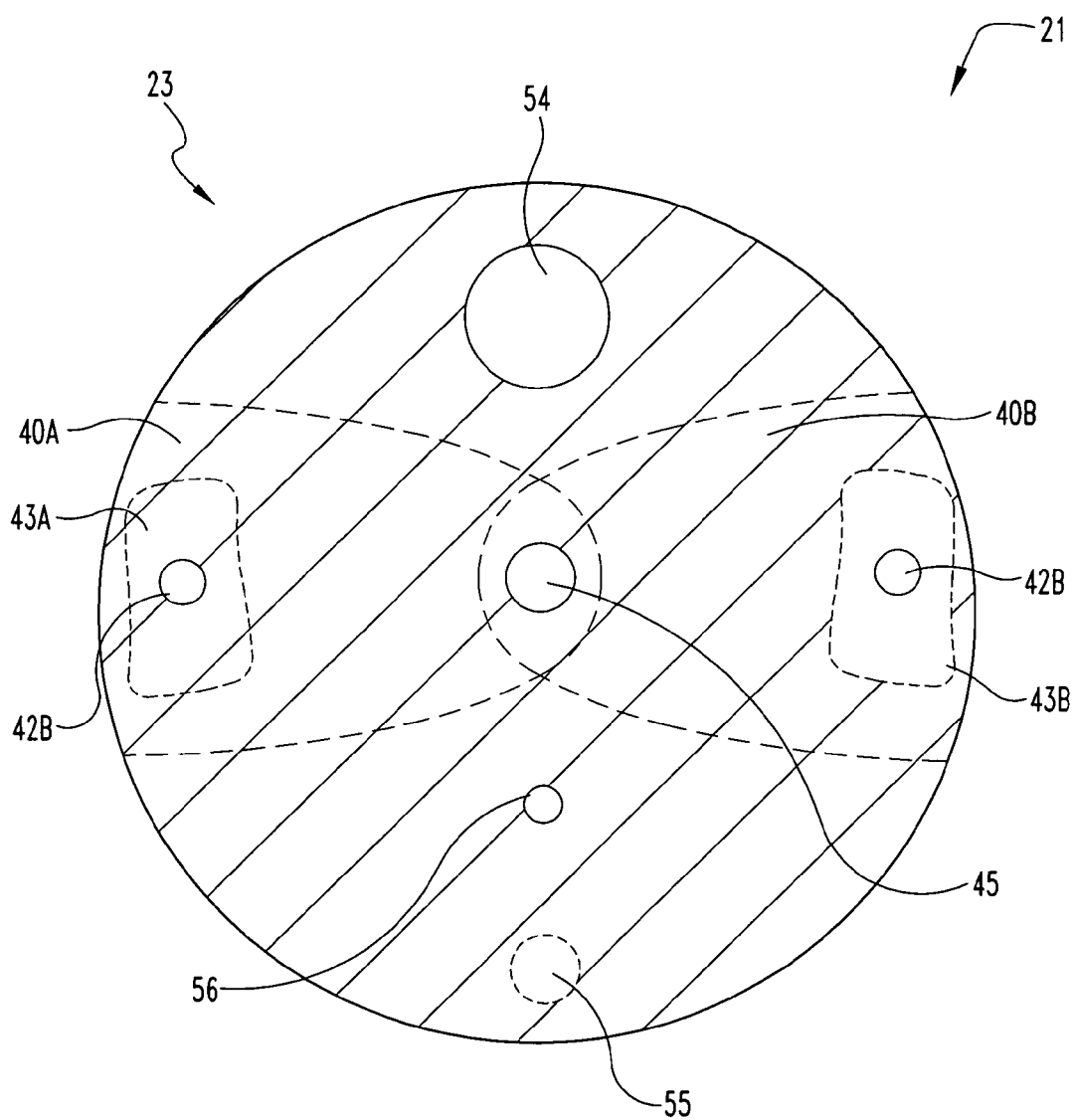
FIG. 6 is a cross section of the FIG. 1 device at the location indicated in FIG. 1

FIG. 6 shows a cross-section view of elongate member 23. Elongate member 23 includes vacuum line 45 which is in fluid connection with vacuum connection 29. Elongate member 23 also includes endoscopic channel 54, guidewire channel 55, and orientation wire lumen 56. Endoscopic channel 54 runs through elongate member 23 from endoscopic inlet port 28 to endoscopic outlet port 25. Guidewire channel 54 runs from guidewire inlet 30 to guidewire outlet 31 at the extreme distal end of elongate member 23. As also shown, suction chambers 40A and 40B are recessed into elongate member 23 and needle chambers 42 and entrapment chambers 43 are arranged in longitudinal alignment on opposing sides of chambers 40.

Figure 7:
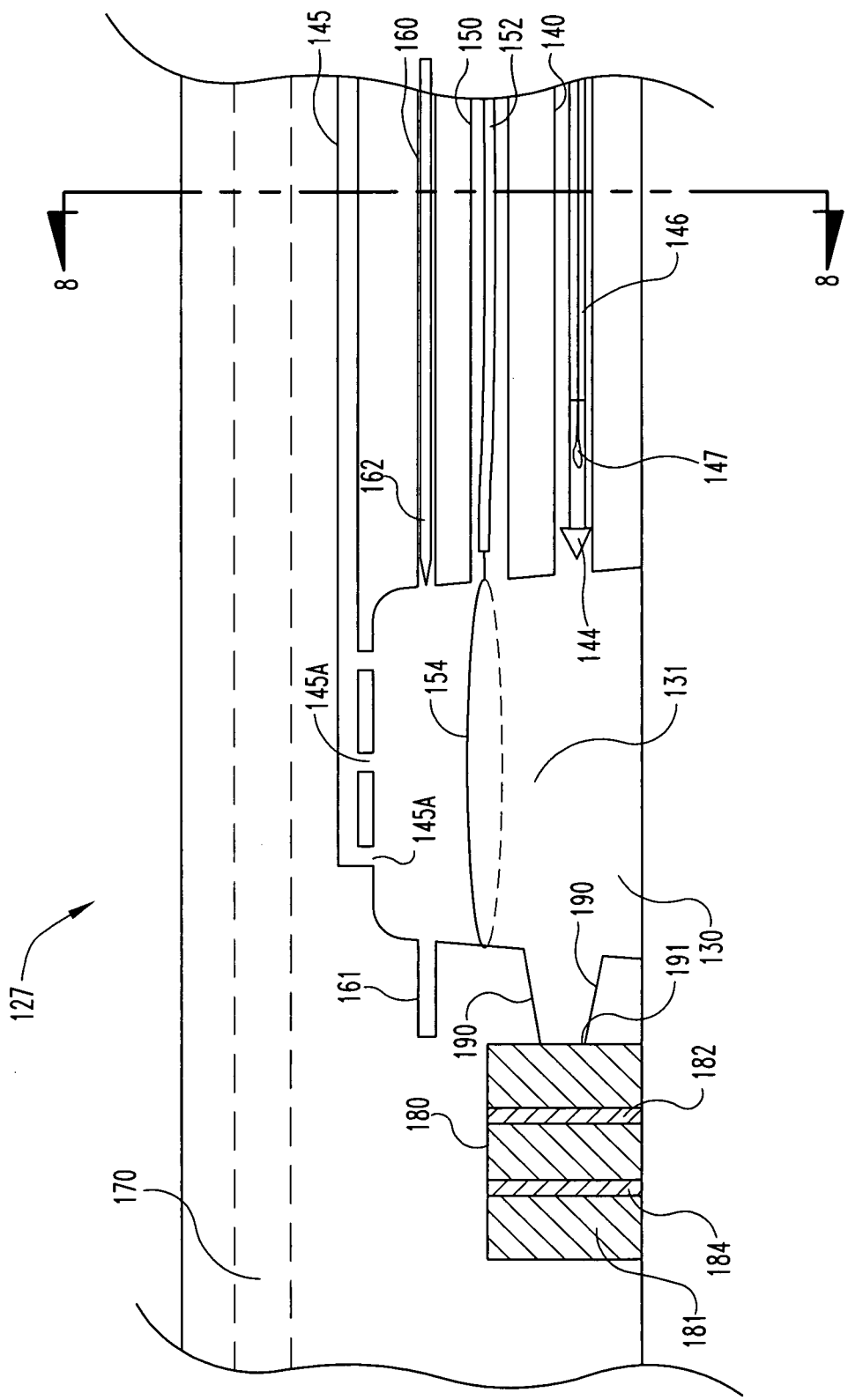
FIG. 7 is a partial sectional view of a variation of another embodiment of the suturing section.
Figure 8:
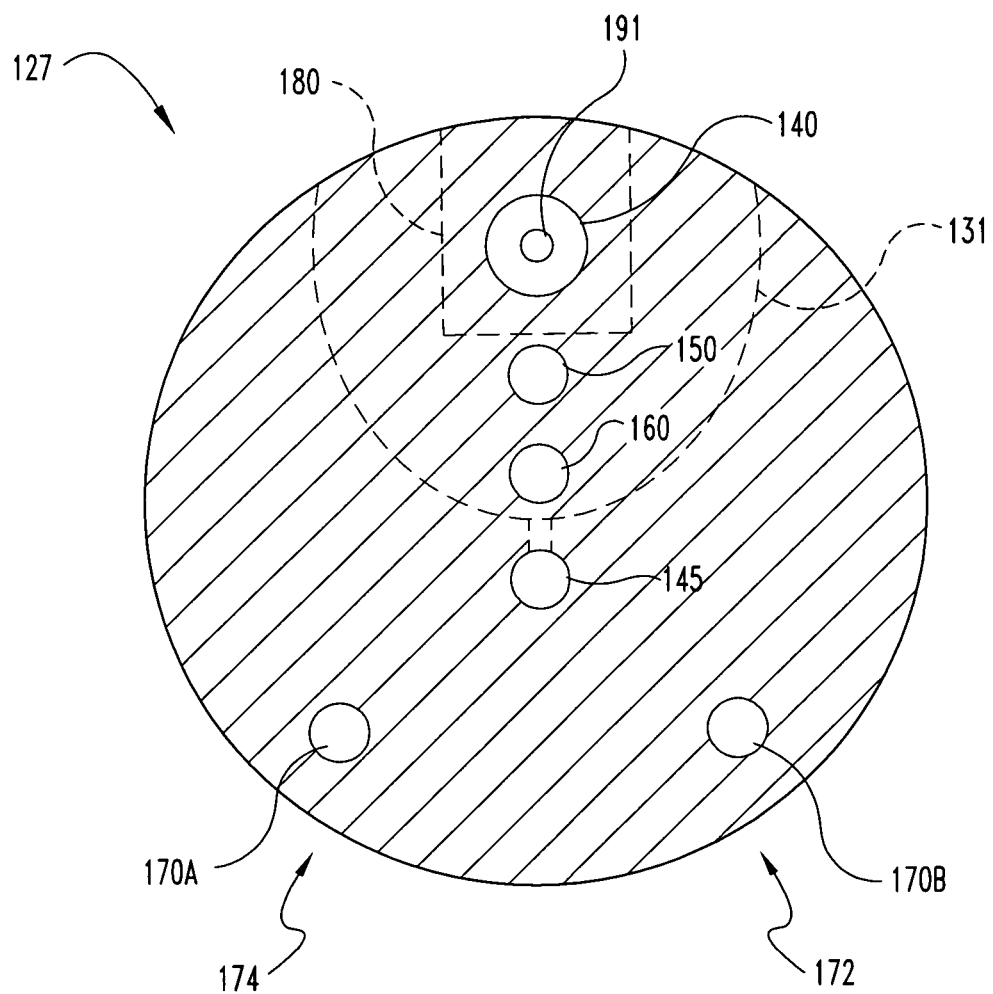
FIG. 8 is a cross section of the FIG. 7 suturing section at the location indicated in FIG. 7.

Referring now to FIG. 7, an alternative arrangement for suturing section is depicted. Suturing section 127 includes a side disposed suction cavity 130 having several suction ports 145 in its closed end such that a vacuum may be applied to cavity 130 via vacuum line 145 to capture a fold of tissue (not shown). Moving from the open to the closed end of the cavity, a suture needle lumen 140, a sectioning device lumen 150, and an injection needle lumen 160 each provide access to the cavity for their respective instruments, the operation of which is described below. It is to be understood that FIG. 8 is a sectional view of the suturing section indicated showing the relative orientation of the lumens but with their instruments removed.

The suture needle lumen 140 provides access for the puncturing device 144 that is pushed through captured tissue by a pusher rod 146. The puncturing device 144 carries a suture thread 147, and is received in the receiving chamber 180 on the distal side of the cavity 130. Ramped guide surfaces 190 are provided at the entrance to receiving chamber 180. These surfaces 190 are tapered to guide the puncturing device 144 into the chamber 180 once the puncturing device 144 has been passed through the captured tissue.

The receiving chamber 180 is configured to retain the puncturing device (and/or the suture thread 147) until released by the surgeon. As illustrated, the receiving chamber 180 is configured to have parallel pieces 182 and 184 of a relatively firm, puncturable material (such as leather) retained in a softer filler material 181 (such as a polymer, foam, or rubber). In operation, the tip of puncturing device 144 will penetrate one or both of pieces 182 and 184 and become captured in chamber 180. The receiving chamber 180 can be snap fit in place, and a release mechanism (not shown) may optionally be provided to assist in removing the chamber 180 with the captured puncturing device 144.

Other mechanisms for passing a suture through tissue captured in a suction cavity could also be employed. For example, U.S. application Ser. No. 10/275,521 (U.S. 2004/0034371), U.S. application Ser. No. 10/430,071 (U.S. 2003/0236535) titled "Apparatus for Ligating/Suturing Living Tissues and System for Resecting/Suturing Living Tissues", U.S. application Ser. No. 10/658,135 (US 2004/0158125), U.S. application Ser. No. 11/085,703 (U.S. $2005/0165419$), and U.S. Pat. No. 5,792,153 to Swain describe mechanisms that are operable to pass a thread longitudinally through captured tissue in an endoscopic arrangement, and these devices may be adapted for use in the procedures described herein. Alternatively, the suturing section may be adapted to apply the sutures radially or circumferentially relative to the axis of the device, for example as described in U.S. Pat. No. 5,947,983 to Solar et al.

The sectioning device lumen 150 provides access for a sectioning device 152 to slice a thin layer from the tissue (not shown) that has been captured in the suction cavity 130. As illustrated, the section device 152 includes a wire loop 154 that is disposed about the periphery of the cavity 130 such that, when a fold of tissue is captured in the suction cavity, it passes through the loop 154. Optionally, the loop 154 can be received in a retaining recess (not shown) in the wall 131 of the cavity 130. With the captured tissue inside the loop, the sectioning device 152 is used to pull the loop 154 proximally through the tissue, which has the effect of slicing or sectioning the tissue. The wire loop 154 can include utilize high frequency or electrical current to facilitate slicing through the tissue. Alternatively, the sectioning device could be configured as a straight wire, a blade or other cutting means suitable for slicing a tissue section captured in the chamber.

In one implementation, the purpose of the sectioning device is to remove the mucosa from the tissue portions to be joined so as to expose the underlying submucosa. Referring to FIG. 9, there is generally considered to be four different tissue layers in human stomach tissue. Beginning with the interior-facing layer, these layers are termed mucosa, submucosa, muscularis propria, and serosa. It is believed that removing the thin mucosal layer of stomach tissue to expose the underlying submucosa provides a tissue site that promotes adhesion with other stomach tissue, and particular other stomach tissue with exposed submucosa. Accordingly, the sectioning device may be arranged to take a thin slice of tissue that removes a portion of the mucosa to expose underlying submucosa, but otherwise leaves the tissue intact.

FIG. 10 illustrates an appropriate sectioning line 100 for resecting a fold of tissue captured in a suction cavity, and FIG. 11 illustrates the resulting sectioned area 153 having exposed submucosa that would result from resection along line 100 in FIG. 10 once the tissue has been released from the cavity. While the boundary between mucosa and submucoas is not uniform, and injecting the tissue will typically cause it to swell (i.e. edema), orienting the sectioning device relative to the depth of the cavity so as to section about 3 to 4 mm of captured/injected tissue, should be suitable for many patients. While it is believed that sectioning into the submucosa is particularly advantageous, it may not be necessary in all situations, and sectioning of less than the full thickness of the mucosa could be employed.

Turning back to FIG. 7, the injection needle lumen 160 provides access for an injection needle 162 to inject the tissue that has been captured in the cavity 130. One use for the injection needle 162 is to inject a material that will swell the captured tissue prior to it being sectioning with the sectioning device 152 described above. Adrenaline with saline or other therapeutic substances, such as materials designed to minimize bleeding or reduce chances of infection, may be injected.

An additional use for the injection needle 162 is to assist in fixating the captured tissue during sectioning. To assist in this fixating, a recess 161 may optionally be provided on the distal side of the cavity 130 opposite the needle channel 160 for receiving the injection needle 162. During use, the injection needle 162 can be pushed through the captured tissue and into the recess 162, and in this position can serve to assist in holding the captured tissue in place. Alternatively or in addition, the suturing needle 147 and/or the vacuum provided via line 145 can be used to provide fixation during the tissue sectioning.

Figure 12:
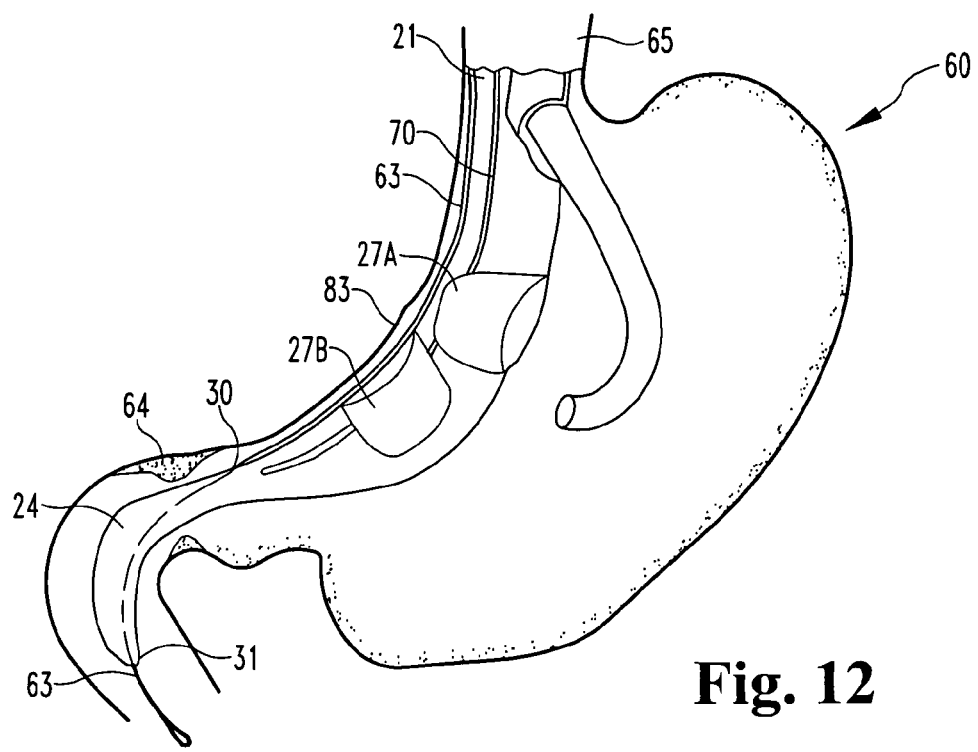
FIG. 12 is a perspective view of the FIG. 1 in a patient's stomach.
Figure 13:
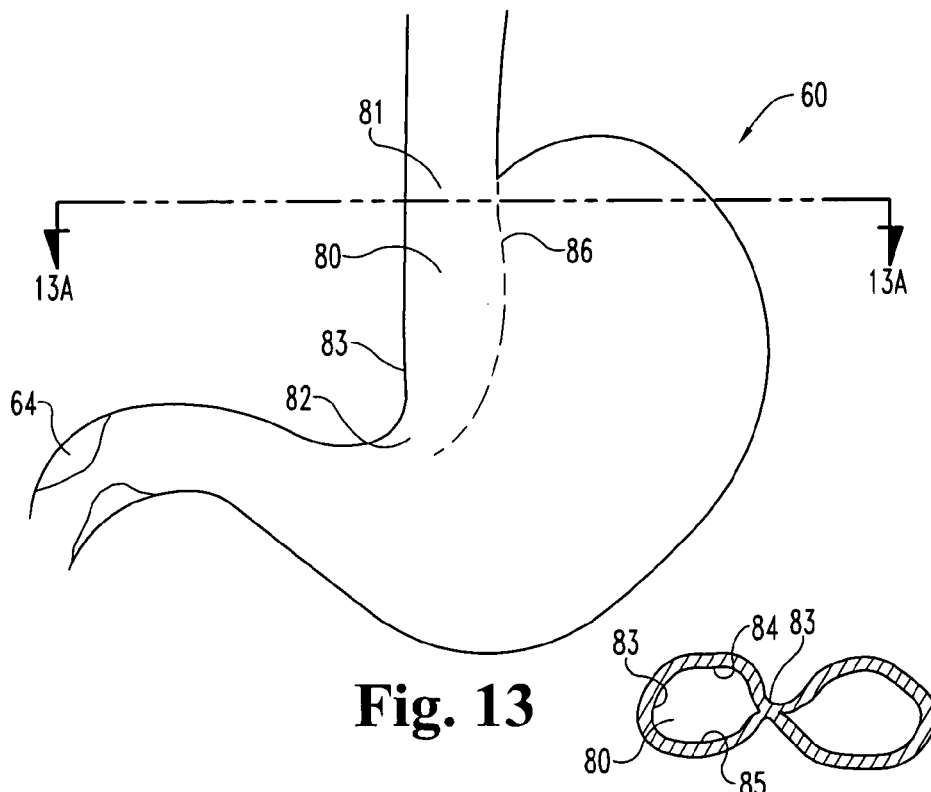
FIG. 13 is an anterior view of a stomach that has been partitioned by the techniques described herein.
Figure 13A:
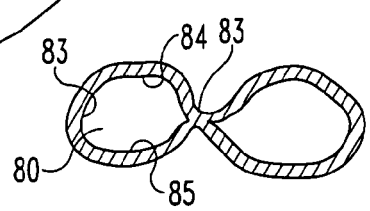
FIG. 13A is a cross section of the portioned stomach of FIG. 13.

Referring now to FIGS. 12 and 13, device 21 is preferably used to create a seam 86 which joins the anterior and posterior walls to form a partition 80 within the patient's stomach 60. The partition 80 is preferably sized to have a diameter of about 2.5 cm at the top segment 81 near the esophagus. The lower section 82 near the pylorus is preferably tapered to a diameter of around 1 cm in width. It is to be appreciated that the locations of the sutures along the anterior and posterior stomach walls (which are then drawn together) determine the ending diameter of the partition. As explained more fully below, with the elongated body positioned generally at the midline of the stomach (e.g. against the lesser curvature) the angular orientation of the suturing section may be set to establish the desired relative location of the sutures.

Referring to FIG. 12, the procedure to create partition 80 begins with a guidewire 63 inserted transorally through the patient's gastrointestinal tract so that is it below the pyloric sphincter 64. The guidewire 63 is then inserted into the guidewire inlet 31 in the rounded distal portion of member 23 of device 21. The guidewire 63 passes through the guidewire channel 55 and exits through the guidewire outlet 30. Alternatively, the guidewire outlet 30 may be on the proximal end 22 of device 21 so that guidewire channel 55 runs through a larger length of elongate member 23. The device 21 is then advanced through the patient's gastrointestinal tract until the distal end of elongate member 23 is forced through the pyloric sphincter 64. Once through, pyloric sphincter 64 serves as a frictional anchor for device 21. As explained more fully below, the distal section 23 may optionally be provided with means for assisting anchoring, such as retractable barbs, inflatable balloon(s), or a magnet that cooperates with an external magnet.

Once device 21 is located within the patient's stomach 60, the elongate member 23 is oriented against the lesser curvature 83 of the patient's stomach 60 by insertion of orientation wire 70 into orientation wire lumen 56. Orientation wire 70 is of sufficient rigidity (or controllable to have sufficient ridigidy) to cause the device to conform to the lesser curvature 83. Orientation wire 70 made be constructed of shape memory material or a flexion material or any other material sufficient to impart orientation to the elongated body. With the orientation wire 70 remaining in place to establish shape and orientation, device 21 can be longitudinally repositioned (i.e. moved axially up and down the orientation wire 70) while maintaining the shape of the lesser curvature 83 as indicated by the orientation wire 70.

Figure 14:
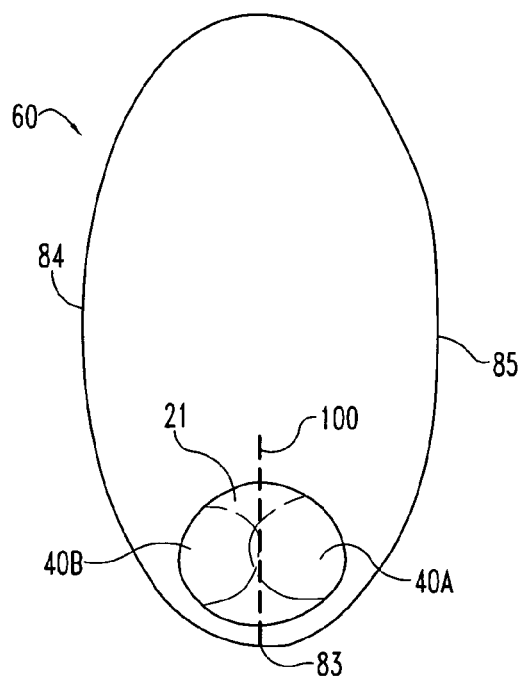
FIGS. 14-17 are cross sectional views looking down the device illustrating the attachment of sutures to the anterior and posterior stomach walls.
Figure 15:
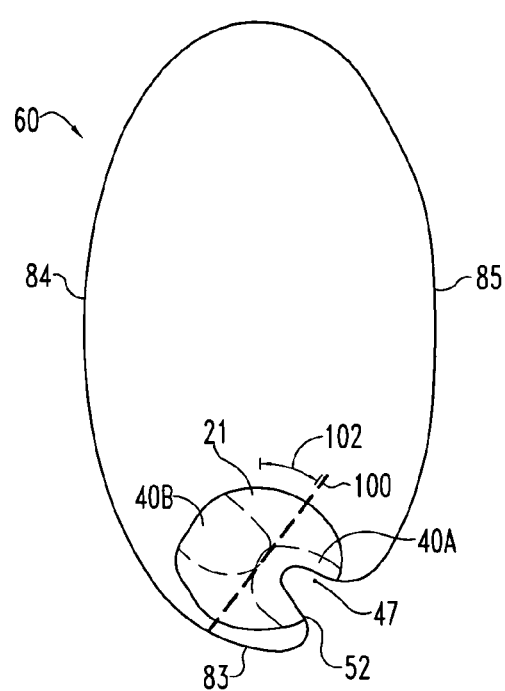

With the device 21 in place and aligned along the lesser curvature 83, the suturing sections 27A and 27B are used to attach two sutures, one in the anterior wall and another in the posterior wall of the stomach. Referring to FIG. 14 which shows overhead views of the stomach looking up from the pelvis, device 21 can be seen in its initial position with device centerline 100 corresponding to the centerline of the stomach, i.e. facing neither the posterior 84 nor anterior wall 85 of stomach 60. Because the suturing sections are disposed at different angular orientations relative to the centerline of the device (in other words, section 27A is disposed anteriorially and section 27B is disposed posteriorially), device 21 only uses a single orientation wire lumen. The device 21 is axially positioned so that the suturing sections 27A and 27B are located near the bottom of lesser curvature 83 to begin the creation of partition 80. The device 21 is rotated clockwise, as shown in FIG. 15, so that centerline 100 is offset by angle 102. Suturing section 27A is then used to draw in a fold 52 of tissue from the anterior wall 85, and the surgeon proceeds to prepare the captured tissue (e.g. by cauterizing it via cautery surfaces 41) and to place a suture.

Figure 16:
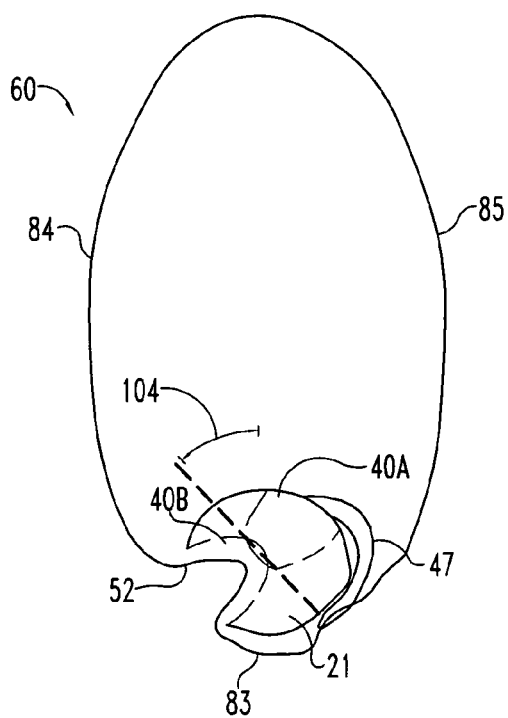
Figure 17:
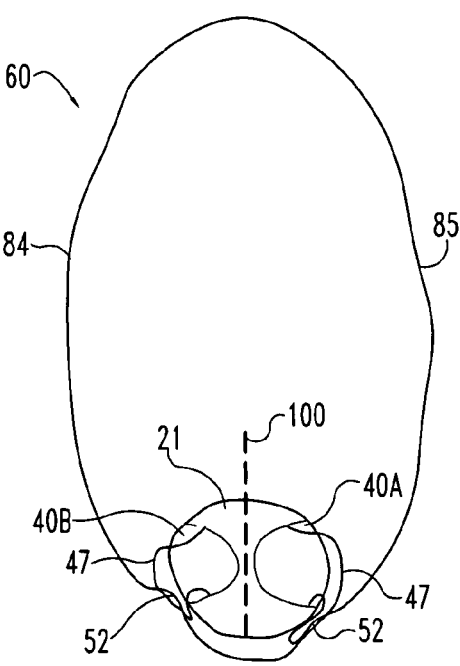
Figure 18:
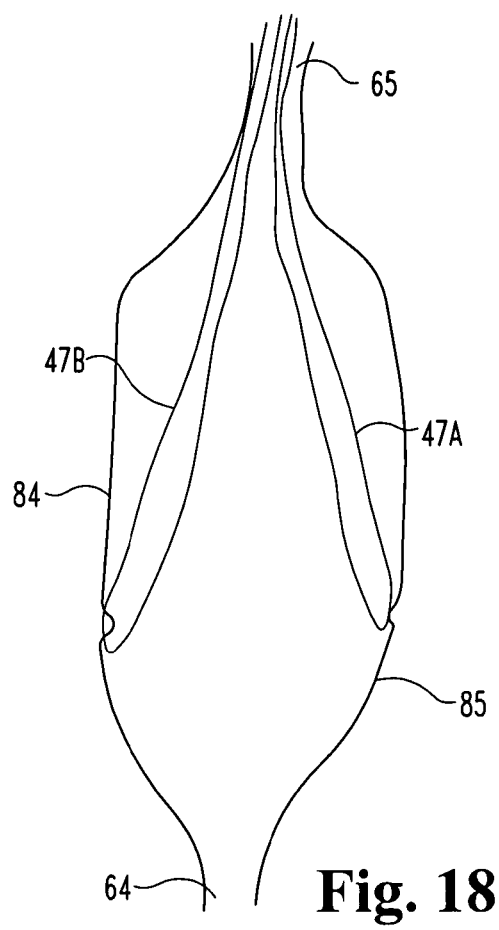
FIG. 18 is a side view of two sutures attached to the anterior and posterior stomach walls with the ends of the sutures extending up the esophagus.

The device 21 is then returned to its original position with the centerline 100 parallel to both the posterior 84 and anterior wall 85 of stomach 60, and then the device 21 is rotated counterclockwise by an amount corresponding to angle 104 (see FIG. 16). Once device 21 is in position, suturing section 27B draws in a section of tissue from the posterior wall 84, cauterizes the tissue surface, and attaches a suture.

As shown in FIG. 12, once the two sutures 47 have been passed through the portions of the anterior 85 and posterior wall 84, the device 21 is withdrawn over the guidewire 63 so that the surgeon may acquire the distal ends of the sutures, having retained their proximal ends throughout the process. Due to the longitudinal offset of suturing section 27B toward the distal end of member 23, the two sutures 47A and 47B created during the first iteration are offset as indicated in FIG. 13. Suture 47B on the posterior wall is located relatively closer to the pylorus 64 than suture 47A, which is located on the anterior wall and is relatively closer to the esophagus 65.

Figure 19:
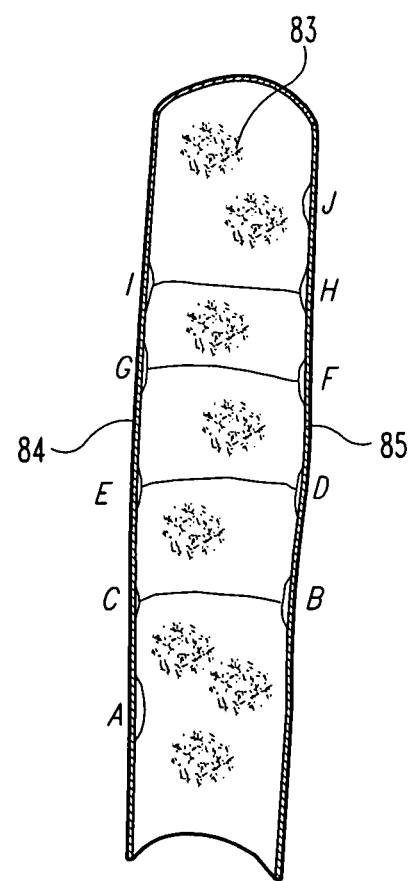
FIG. 19 is a cutaway view of the stomach looking at the lesser curvature and illustrating the positioning and attachment of opposing sutures on the anterior and posterior walls.

The creation of partition 80 within the patient's stomach 60 typically will require a series of sutures (e.g. 8-14) in a stitching pattern such as depicted in FIG. 19, with the pairing of sutures that are tied together and joined indicated by the connecting lines (i.e. C to B, E to D, etc.). This series of sutures can be created by repeating the procedure multiple times, with reloading of each suturing section (27A, 27B) and repositioning of the device 21 between iterations. For example, in the first iteration sutures A and B would be attached. Device 21 would be axially slid up orientation wire 70 and the procedure repeated to attach sutures C and D. To create a taper, the angles 102 and 104 can be adjusted such that sutures are placed successively further away from the lesser curvature.

Once the first four sutures are in place, the surgeon may then couple the two sutures B and C together by an attachment means. For example, a means of attachment includes a surgical knot, a clamp, or any other means that may occur to one skilled in the art. The means of attachment are then slid into place and the two sutures are drawn together, creating contact between the two folds of tissue which have been modified or removed (i.e. having been cauterized or abraded, or having a surface portion sectioned and removed). It is believed that the resulting areas of modified or removed tissue will then develop scar tissue to facilitate formation of a relatively permanent bond.

The procedure has been described so far in connection with a device 21 with two suturing sections that are radially offset (i.e. one faces anteriorially while the other faces posteriorally) and a single orientation wire lumen. Devices with only one suturing section or with suturing sections that are not radially offset may also be employed. For such devices, multiple orientation wire lumens can be used to provide the proper curvature to the device when it is rotated anteriorially or posteriorly.

Figures 20, 21:
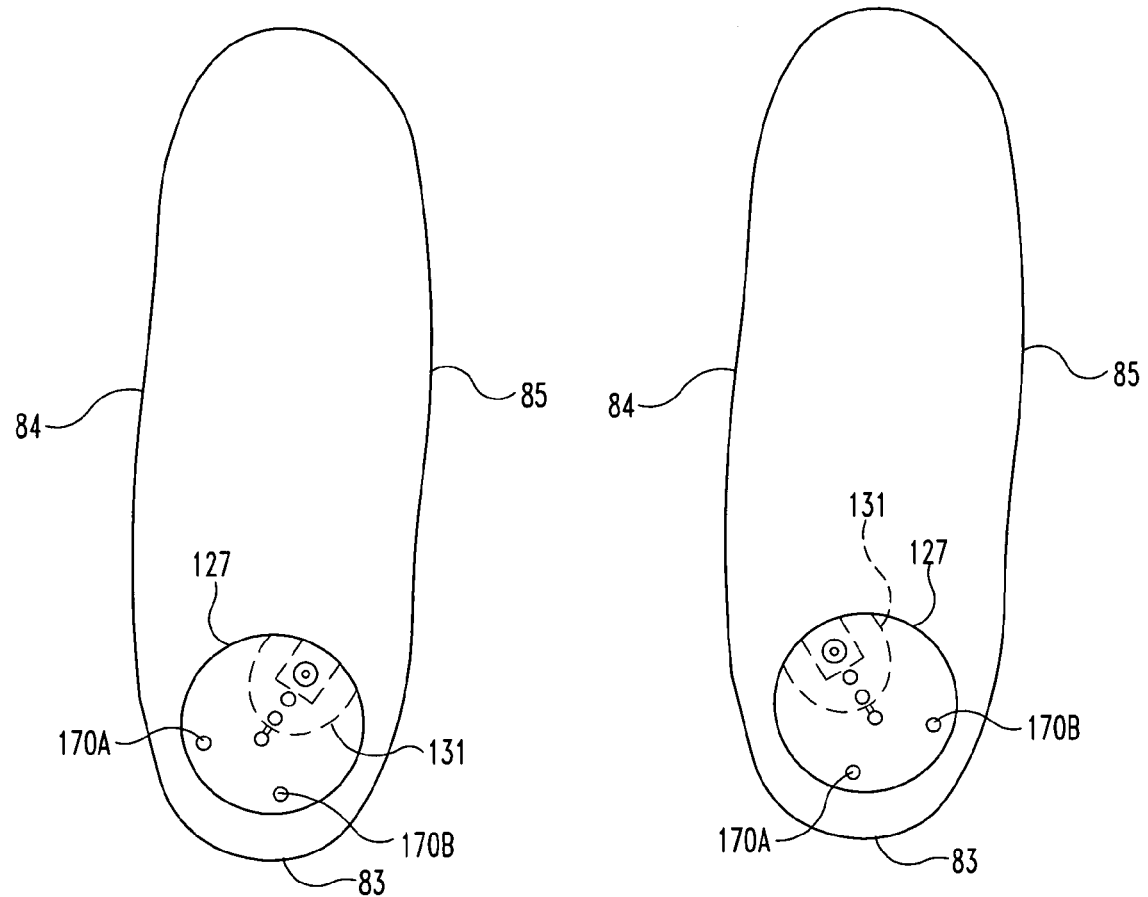
FIGS. 20 and 21 are sectional views corresponding to FIGS. 14-17 illustrating the use of two orientation wire lumens to rotate the device.

For example, as shown in FIG. 8, suturing section 127 has orientation wire lumens 170A and 170B that are each offset from the centerline of the elongated body. More specifically, lumen 170B is nearer surface portion 172 whereas lumen 170A is nearer surface portion 174. When the suturing section 127 is rotated anteriorially, as depicted in FIG. 20, an orientation wire located in lumen 170B is activated biased towards the lesser curvature 83 so as to have the surface portion 172 that is closest to lumen 170B in contact with the lesser curvature 83. Likewise, when the device is rotated posteriorially as shown in FIG. 21, an orientation wire in lumen 170A is activated to provide the desired curvature of the device.

Figure 40:
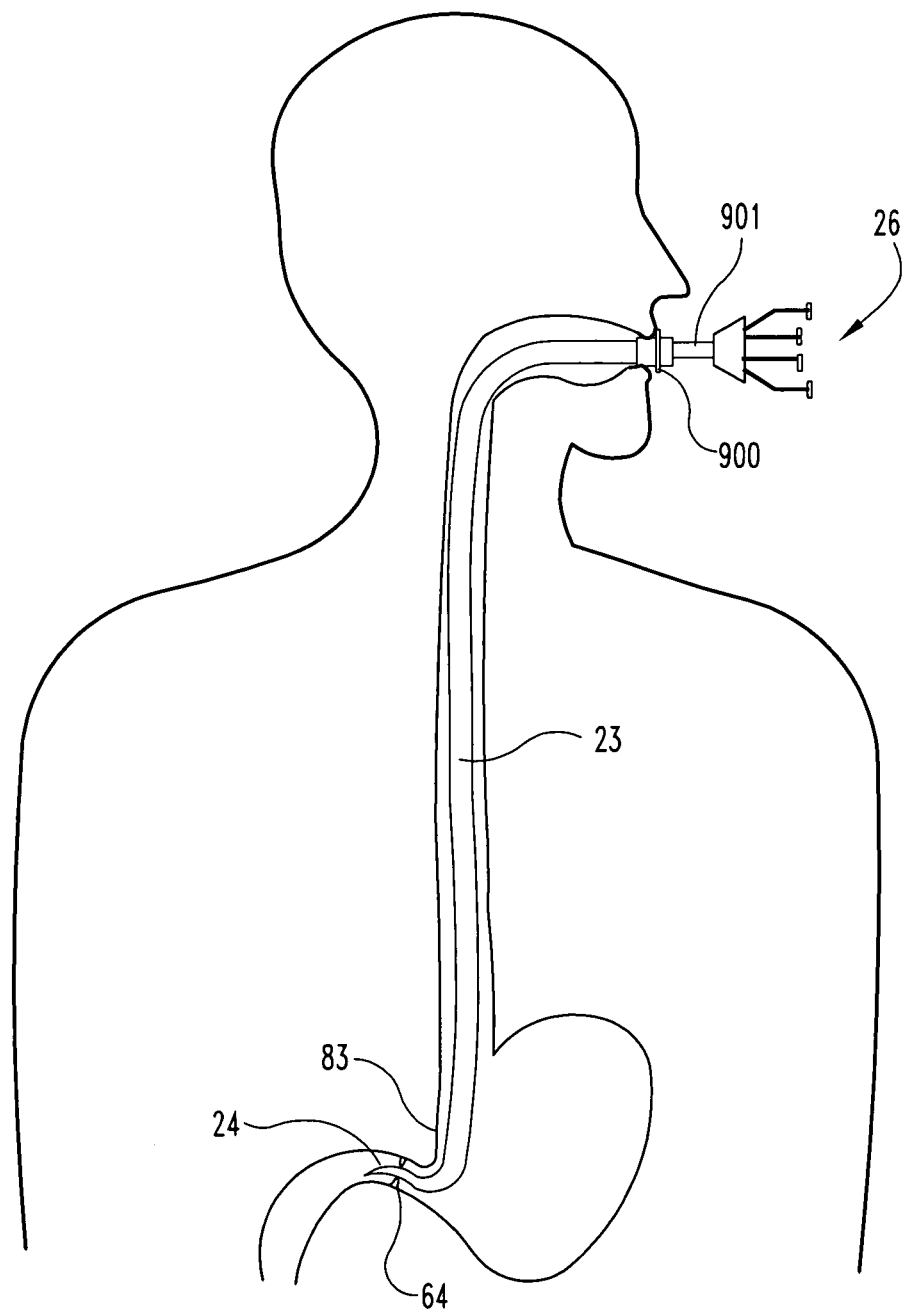
FIG. 40 is a side cutaway of a patient with a surgical system inserted into the stomach.
Figure 41A:
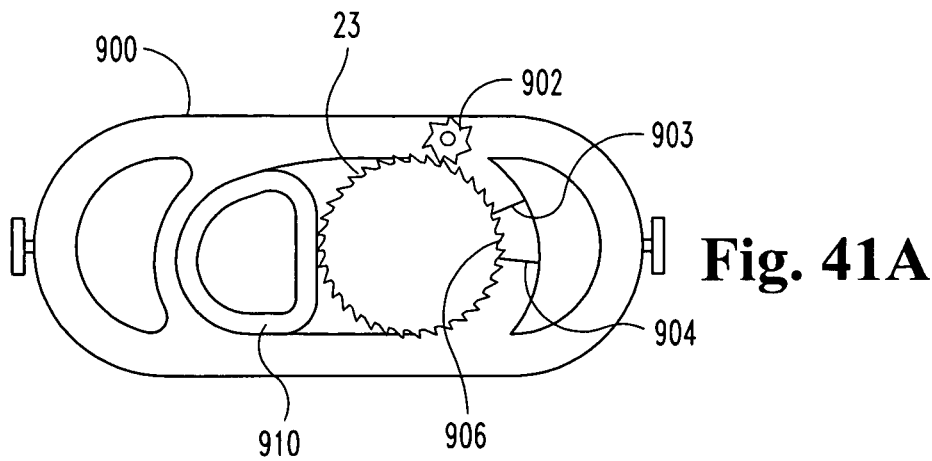
FIG. 41 shows a top and side view of the bite block used in FIG. 40 with the lower left corner illustrating a side view of the airway.
Figure 41B:
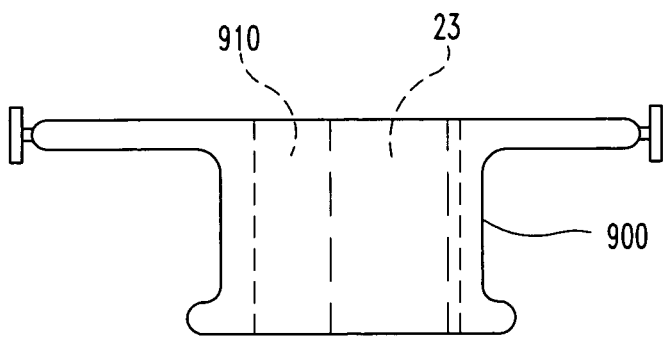
Figure 41C:
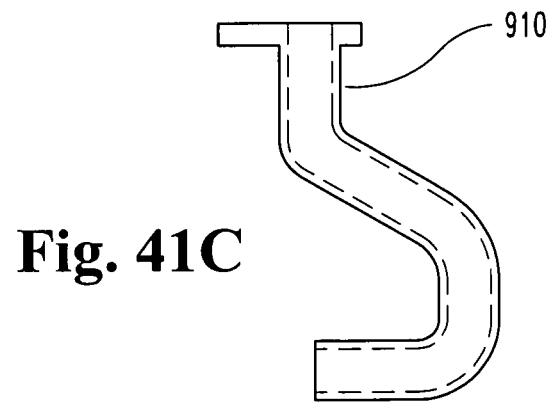

With reference to FIGS. 40 and 41, one mechanism for rotating the device is by manually grasping and rotating the proximal portion 901 that is extending from the patients mouth. The body 23 can be constructed of appropriately stiff material such that this turning is translated down its length to also turn the operating portions located inside the patient's stomach.

In typical operation, a bite block 900 will be positioned in the patient's mouth and a head strap (not shown) attached to either side of the bite block 900 will be wrapped around the patients head to further secure the bite block 900 in position. The bite block 900 may be used to accommodate both the elongated body 23 used to perform the surgical operation on the stomach as well as a conduit 910 for providing an airway. Once in position, the elongated body 23 may be clamped or otherwise secured to the bite block to keep the proximal portion in position. Alternatively or in addition, the bite block 900 can be configured to assist in rotating the device, for example by the provision of gears 902 or a ratcheting mechanism that engage corresponding surface portions of the body 23 to assist in its relative rotation. Gradations or markings 903, 904 on the bite block 900 can also be provided to match up with corresponding markings 906 on the proximal portion of body 23 to indicate the relative angular orientation of the device.

The orientation wires may remain in place and be activated and deactivated as needed. Alternatively, they can be withdrawn and inserted when needed. The orientation wires can be activated by manual pulling or cable gathering (similar to the operation of endoscope control) or, when constructed from shape memory material (e.g. nitinol) then can be activated by heating (e.g. application of electrical energy). In place of or in addition to the orientation wires, an alternative mechanism for aligning and orienting the elongated body 23 along the lesser curvature can be used. For example, a series of suction ports may be provided along that portion of the body which is to be in contact with the lesser curvature. A suction force may then be applied to these ports to draw the body against the lesser curvature of the stomach wall. It is to be understood that these suction ports are used for purposes of alignment and not tissue capture, and thus they would operate independently from the suction chamber used to capture the tissue for suturing. Where different angular orientations of the body are utilized (i.e. where the device is rotated in an anterior or posterior direction as described above) these suction ports can be arranged in two longitudinally extending lines wherein suction can be applied to each line individually.

Figure 22:
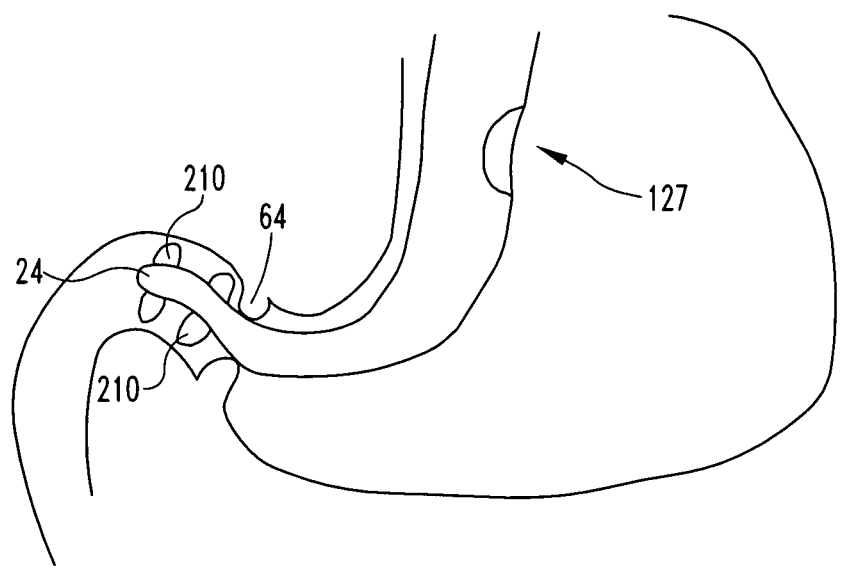
FIGS. 22 and 23 are anterior views of the stomach showing the distal anchoring portion of different embodiments anchored in the first portion of the duodenum.
Figure 23:
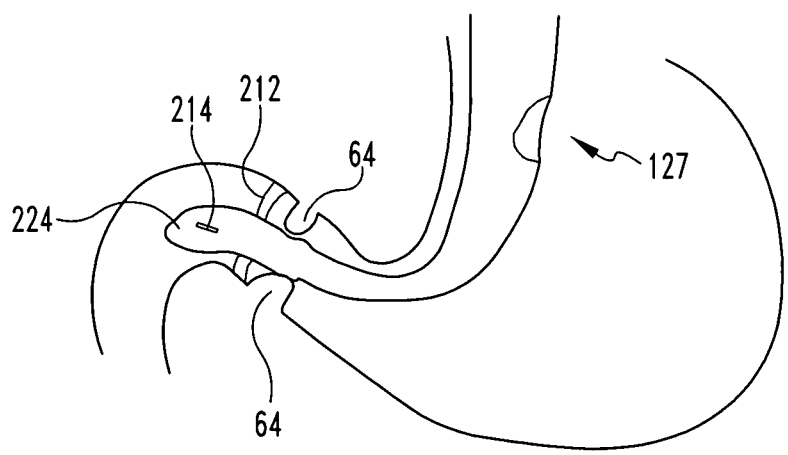

It is to be appreciated that one purpose of the distal anchoring section is to provide secure anchoring of the device against axial movement (e.g. being prematurely withdrawn from the pylorus) while the suturing section is attaching sutures to the stomach walls. Referring to FIGS. 22 and 23, the distal section 24 may be provided with means for enhancing anchoring, such as retractable wires 212, inflatable balloons 210, and/or a magnetic material 214 that cooperates with an external magnet (not shown). As illustrated, these anchoring structures can be provided on the portion of distal section 24 that extends past the pylorus 64. They serve to retain the distal section 24 in place while the suturing section 127 is operating on the stomach walls. Alternatively, anchor assisting means can be provided on either side of the pylorus 64 or only on the portion proximal from the pylorus 64.

Figure 24:
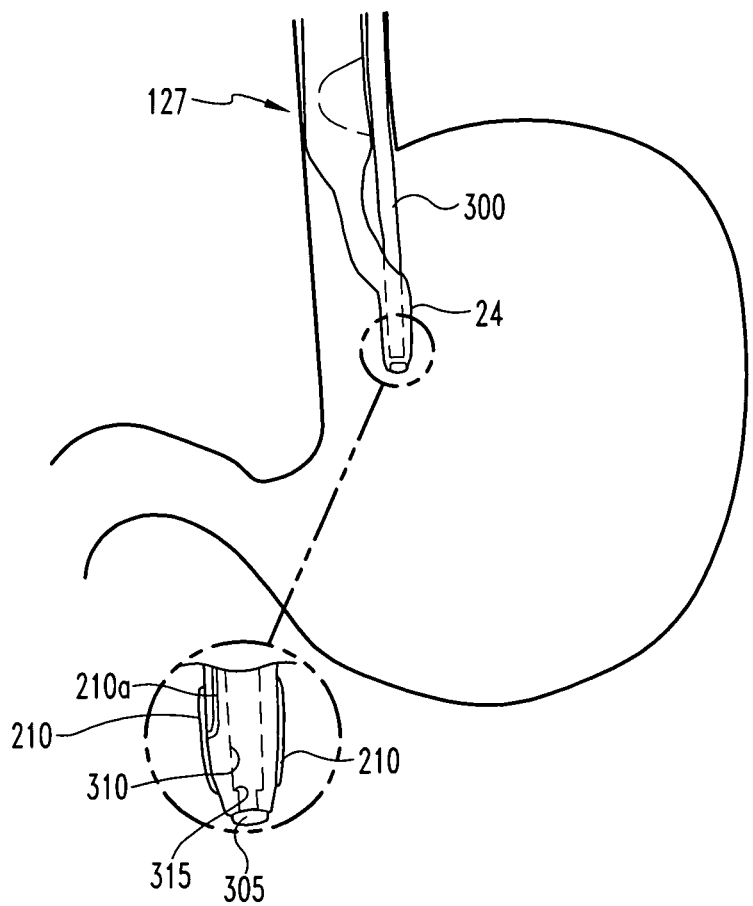
FIG. 24 is an anterior view of the stomach showing insertion of the distal anchoring section via an endoscope and including an enlargement showing details of the distal tip.

While the distal section 24 has been described as being placed into its initial position (e.g. being anchored in the pylorus) by being threaded over a guidewire, other means of positioning the device may be employed. For example, referring to FIG. 24, the distal section 24 may be configured to receive an endoscope 300, for example a 5 mm endoscope, and the endoscope 300 may be used to guide the distal portion 24 into position. In this arrangement, an endoscope lumen 310 is provided in portion 24 with a visualization port 305 (or a see-through closure) at its distal end. When inserted in the lumen 310, the endoscope contacts a stepoff 315 at the distal end and, while also using the endoscope for visualization, the operator uses the endoscope to push the distal portion 24 through the stomach and into the pylorus. The detail in FIG. 24 of the distal tip also illustrates balloon 210 in a deflated configuration. Once placed, the balloon 210 can be inflated via an inflation lumen 210a. Alternatively, the balloon can be inflated and deflated during insertion as a means of assisting to advance the distal portion into position.

A useful aspect of the devices described herein is their ability to be distally anchored while the suturing section operates on the stomach walls.

Figure 25:
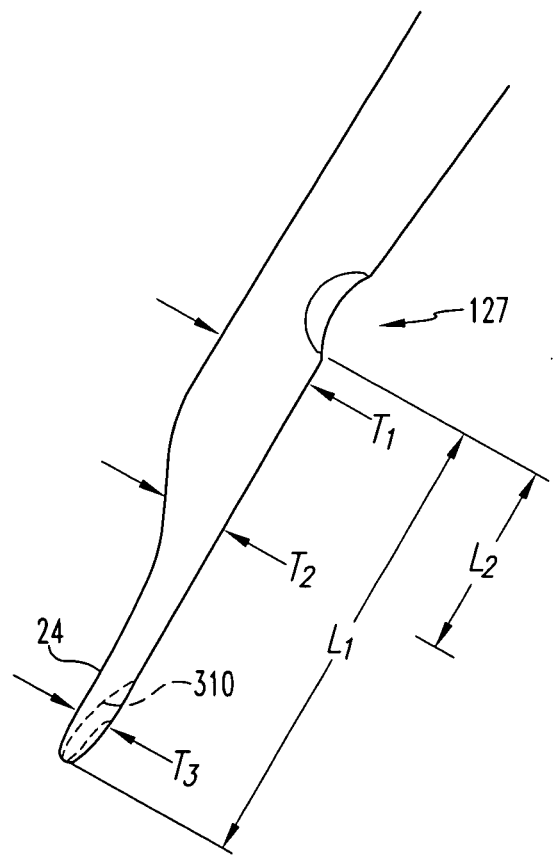
FIG. 25 is a side view of a device showing dimensional features.

FIG. 25 illustrates general dimensional aspects that assist in this implementation. The length L1 is the length corresponding to the distal anchoring section, measured from the distal-most portion of the suction chamber of suturing section 127 to the distal tip of the anchoring section. This length L1 will generally be in the range of 10-20 cm, for example about 15 cm. Thickness T1 refers to the diameter of the suturing section, and this will generally range from 15-20 mm. The distal anchoring section will typically include a taper down to a thickness T2 of about half the thickness T1. This taper may be used to occlude the pylorus. The distance L2 from the distal most portion of the suction chamber to this taper may be in the range of about 0.5 to 2 cm. The portion of the distal anchoring section that extends into the pylorus may have a thickness T3 of about 7 mm so as to be able to accommodate the 5 mm endoscope used for insertion.

Figure 26:
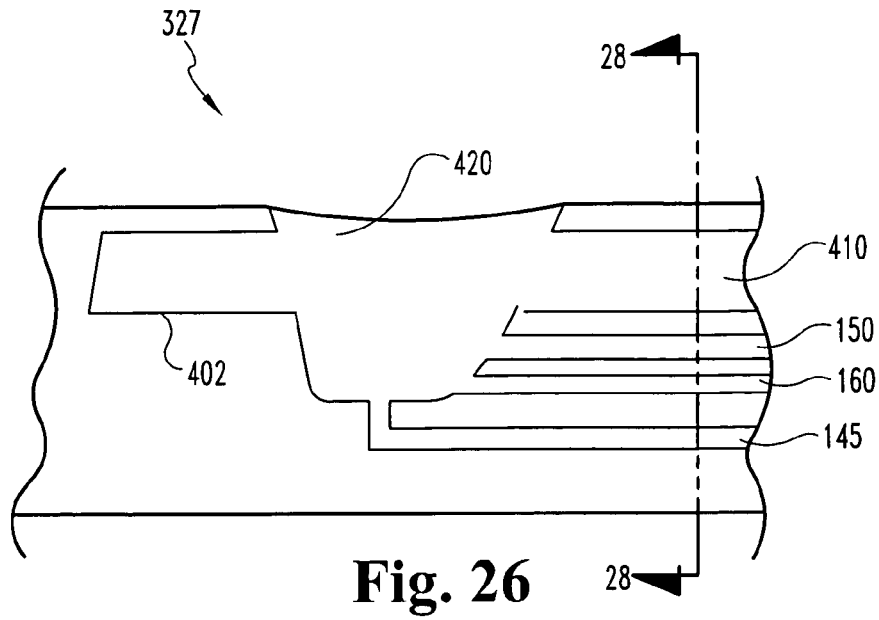
FIG. 26 is a side view of a suturing section that utilizes a removable shuttle.
Figure 27:
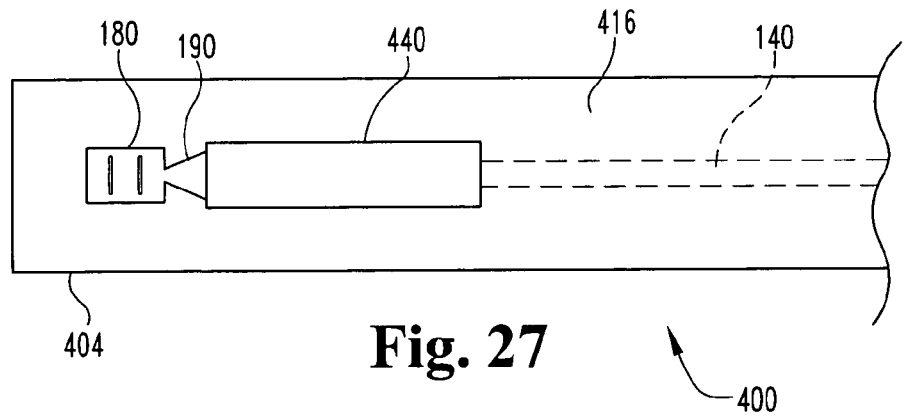
FIG. 27 is a top view of the removable shuttle used in the FIG. 26 suturing section.
Figure 28:
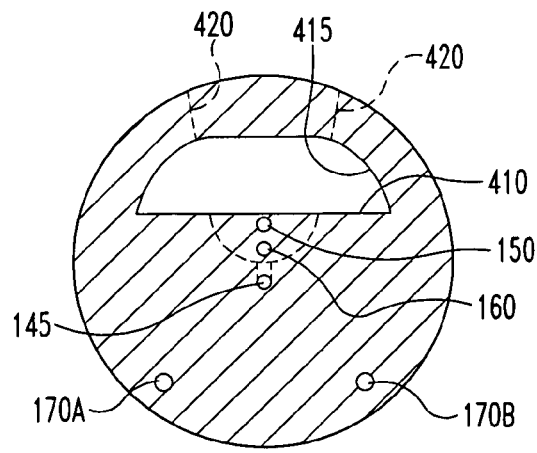
FIG. 28 is a sectional view of the suturing section at the location indicated in FIG. 26

Turning now to FIGS. 26-28, a variation on the suturing section 127 illustrated in FIG. 7 is depicted. Suturing section 327 is identical to suturing section 127 except that the needle lumen 140 and the receiving chamber 180 are provided in a removable shuttle 400 that is slideably received in a shuttle lumen 410 of the device. As shown in the top view of FIG. 27, the shuttle 400 has an opening 440 that aligns with vacuum cavity 420 when the distal portion of shuttle 404 is positioned in the distal portion of shuttle lumen 410. Rounded shoulders 416 extend along the length of the shuttle on either side of opening 440, and corresponding guide surfaces 415 extend along the length of lumen 410.

With shuttle 400 inserted in lumen 410 and the opening 440 aligned with cavity, the suturing section operates in the same manner as suturing section 127 of FIG. 7. A vacuum is drawn via line 145, the captured tissue is injected via lumen 160 and sectioned via lumen 150, and a suture is passed through the captured tissue via lumen 140 and captured in chamber 180. However, once the tissue has been released, the shuttle 400 can be withdrawn from its lumen 410. This allows the operator to remove the captured needle from the chamber 180 without removing the entire device.

While only the needle lumen 140 is shown on the removable shuttle 400 in FIGS. 26-28, it is to be appreciated that one or more of the sectioning lumen 150, the injection lumen 160 and even the vacuum lumen 145 can be integrated into the removable shuttle 400.

Figure 29:
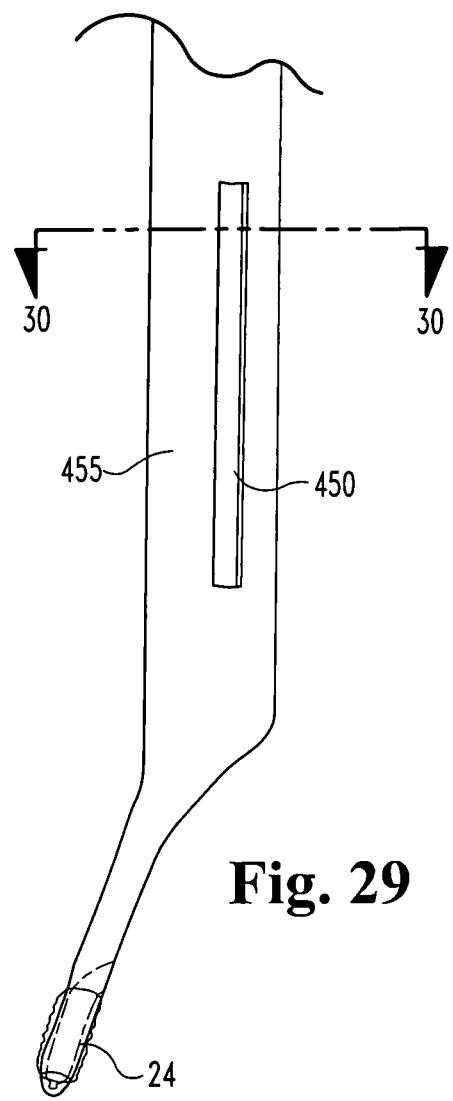
FIG. 29 is a side view of a device according to another embodiment.
Figure 30:
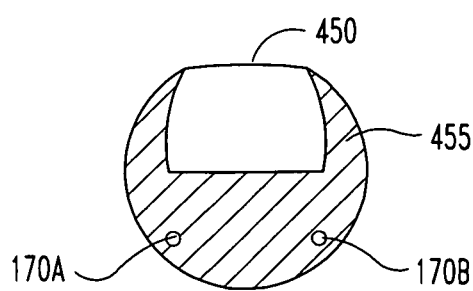
FIG. 30 is a sectional view of the FIG. 29 device.
Figure 31:
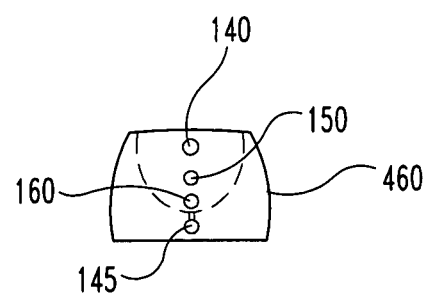
FIG. 31 is a sectional view of the shuttle used with the FIG. 29 device.

When the vacuum lumen is included in the removable shuttle, a positioning device 455 can be configured to have an elongated slot 450, as depicted in FIG. 29-30. In this variation, the removable shuttle 460 will contain all of the operative mechanisms for suturing, as depicted in the cross section of FIG. 31. In use, the shuttle 460 can be positioned anywhere along the longitudinal length of the slot 450 to position a suture. To assist in longitudinal positioning, the proximal portion of the shuttle 460 (not shown) can be marked (i.e. with gradations or markings) so as to measure how far into the lumen the shuttle has been extended. Knowing the relative dimensions of the device, the operator can then determine where along the slot 450 the shuttle is positioned. Alternatively or in addition, stops can be provided on the shuttle 460 or in the lumen of the device 455 to aid in positioning. For example, a series of extension members (not shown) can be attached to the distal end of the shuttle 460 to control how far into the lumen the shuttle can extend. In other words, a 1 cm extension member would make the shuttle stop 1 cm from the end, a 2 cm extension member would make the shuttle stop 2 cm from the end, etc.

It is to be appreciated that the instruments and techniques described here are suitable for providing a suture through stomach tissue that has been prepared for joining with other stomach tissue. For example, as shown in FIG. 32, two strands of suture thread may be attached to the anterior 85 and posterior 84 stomach walls such that their free ends A and B extend from opposite sides of prepared tissue areas 153. From outside the body, the operating physician can attach the A ends together and, by pulling on the B ends, bring the walls 85 and 84 together, as shown in FIG. 33. The B ends may then be joined and a knot or crimp 610 slid down to the tissue to complete the attachment as shown in (FIG. 34). The process may be repeated as often as necessary until enough tissue sections have been joined to form an adequate seam 86 (see FIG. 13).

To reduce the number of sutures that need to be tied together in this way by the surgeon, the device can be constructed such that a single suture thread is attached at multiple tissue sites. For example, U.S. Pat. No. 5,792,153 to Swain illustrates one such mechanism for attaching a single thread to multiple tissue sites. The general approach of the Swain device, and of other known devices of this type, is to configure the suturing section as a type of sewing machine, wherein the suture is carried by a thread carrier that is passed back and forth across the suction chamber by a hollow needle. Alternatively, instead of capturing the thread on the far side of the suction chamber via a thread carrier, the thread can be directly captured, for example by catching a loop of the thread with a spring loaded latch, as is also know in the art. Furthermore, while many of the longitudinally operable needles described so far generally begin operation on the proximal side of the suction cavity, it is to be understood that these suturing devices can be modified so as to begin operation on the distal side as convenient.

FIG. 34 illustrates a useful suturing pattern when a sewing machine type device is employed. For ease of illustration, four folds of tissue 710, 720, 730, 740, two each on the anterior 85 and posterior walls 84 are illustrated. However it is to be understood that the folds of tissue depicted in FIG. 34 are each created by the suction chamber at the time the suture is passed through the respective tissue fold. In illustrated step 1, the suture shuttle (which carries the suture thread) is passed through fold 710 on the anterior wall 85 from a proximal to distal direction by a hollow needle. In step 2, the suture shuttle is reinserted into the hollow needle, and in step 3 the suture shuttle is passed through fold 730 on the posterior wall 84 also from a proximal to distal direction. With the suture shuttle still on the distal side of the suction chamber (not shown) the suture is passed through fold 740 in a distal to proximal direction. The suture shuttle is then repositioned on the distal side of the chamber and in step 6 passed through fold 720 in a distal to proximal direction. The end result is to produce a suture pattern across the four folds that resemble a "FIG. 8", with the free ends (extending from bottom of page in step 6) being tied together to complete the lower loop of the "FIG. 8".

Figure 36:
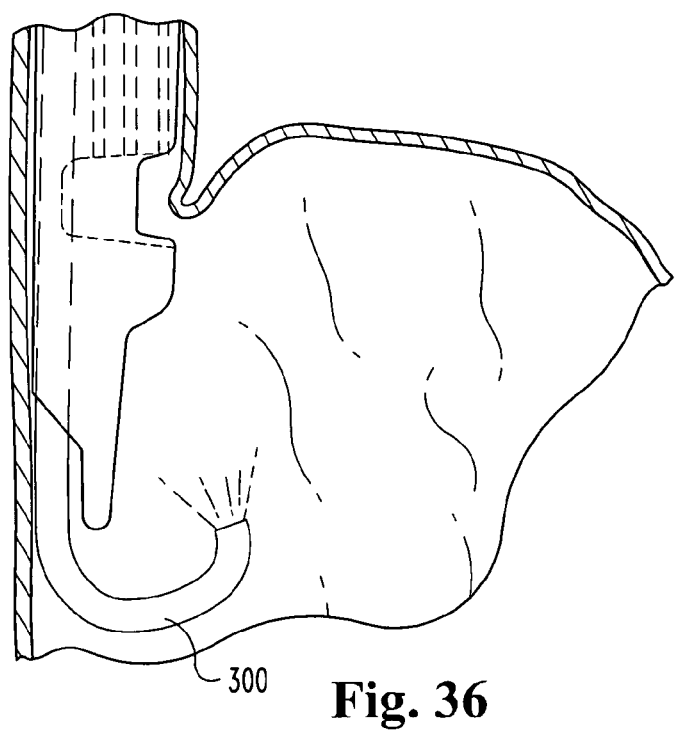
FIG. 36 is a sectional view of an embodiment used to form tissue plications at the esophageal junction.
Figure 37A:
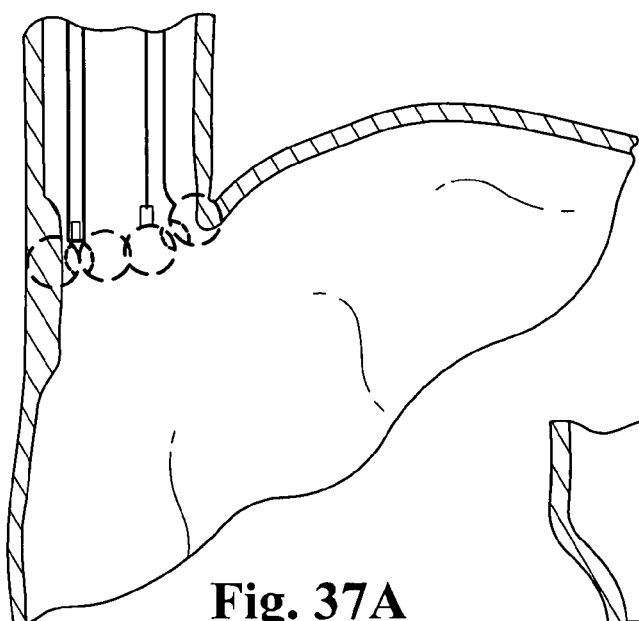
FIG. 37A schematically illustrates the sutures placed with the FIG. 36 device and FIG. 37B schematically illustrates the formation of plications with the sutures.
Figure 37B:
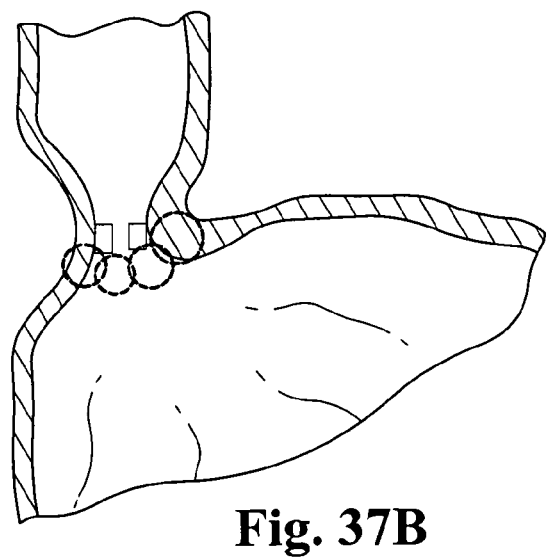
Figure 39:
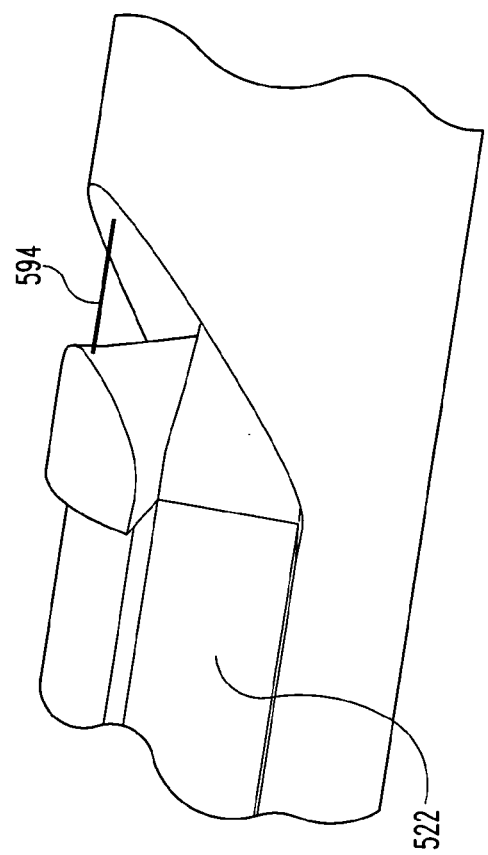
FIG. 39 is an enlarged view of the arch cutting section of the FIG. 38 device.
Figure 38:
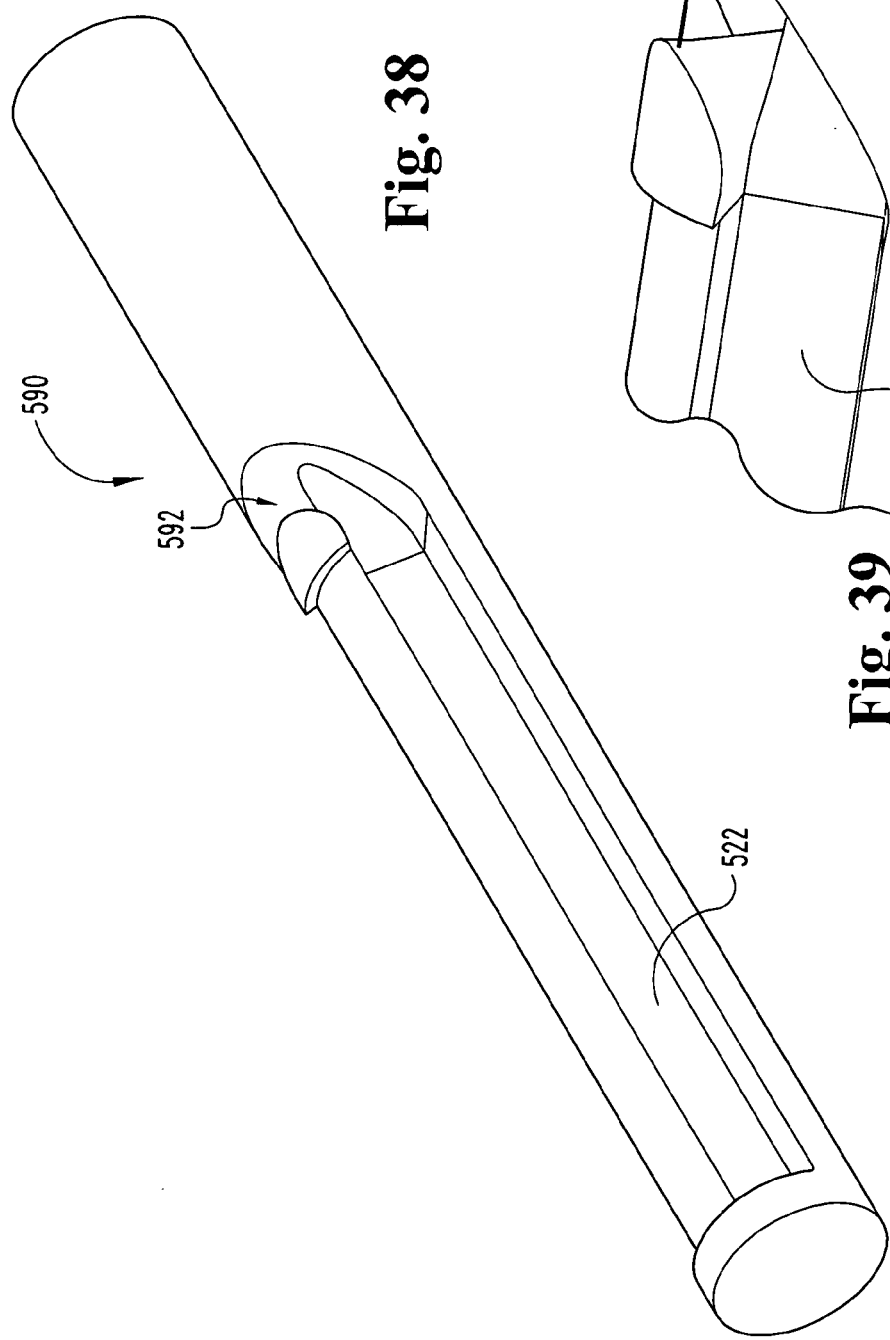
FIG. 38 is a perspective view of a suction cavity arrangement to cut an arch in the stomach near the esophagus.

FIG. 36 is another illustration of this "FIG. 8" suturing pattern, and FIG. 37 shown alternative suturing patterns and techniques that use plugs and anchors to either join suture threads or provide the initial suture location. It is to be understood that the shaded areas indicated areas of sectioned or cauterized tissue and that the left and right sides of the figures correspond to the anterior and posterior stomach walls (or vice versa). FIG. 38 shows a still further variation of useful suturing patterns. The FIG. 38 suturing pattern begins with a plug or pledget anchoring the first end of a suture thread attached to the posterior wall. The suture pattern of FIG. 38 may be used in connection with curvilinear needles, as depicted in FIG. 39, that serve to attach sutures radially or circumferentially relative to the axis of the device.

Figure 43:
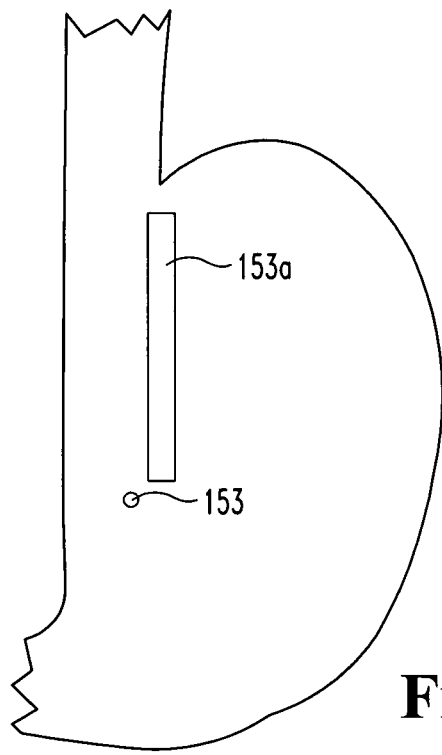
FIG. 43 is a cutaway of the stomach with a continuous slot of prepared tissue replacing some of the discretely prepared sites of FIG. 42.
Figure 42:
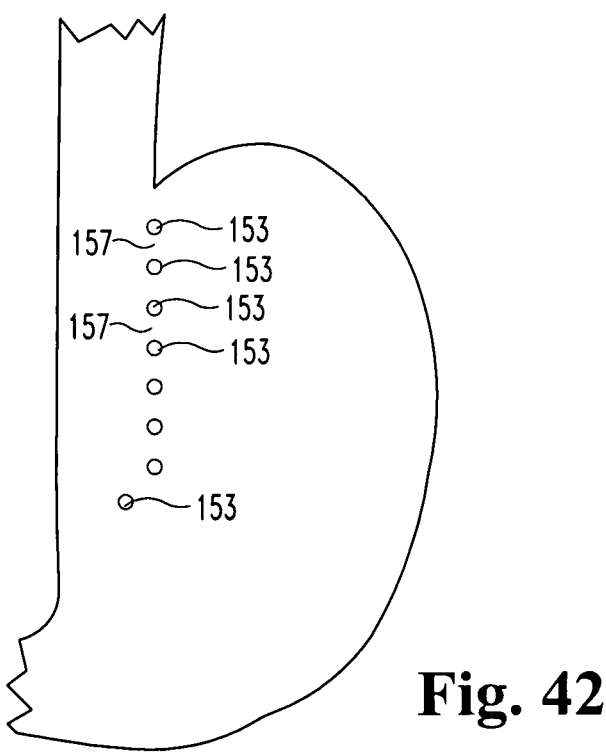
FIG. 42 shows a cutaway of the stomach with a useful pattern of discretely prepared tissue sites for partitioning the stomach.

It is to be understood that the procedure has so far been described in connection with interior stomach tissue that is operated on to promote joining (i.e. has been cauterized or abraded, or wherein a portion of the surface tissue has been sectioned or removed) in a spot type fashion. In other words, referring to FIG. 42 which shows the relative position of sites 153 of resected or removed tissue (which could alternatively be cauterized or abraded tissue) on the posterior wall 84 useful for joining to corresponding anterior wall portions so as to form seam 86 (see FIG. 13), there may be sections of unaltered tissue 157 between the sectioned sites 153. Referring to FIG. 43, in alternative implementations, the stomach walls may be prepared (i.e. cauterized or abraded, or alternatively sectioned or removed) in a pattern resembling a strip 153*a*. In the illustrated implementation, the strip 153*a* corresponds to the upper generally constant width portion of the partition, and an isolated spot portion 153 is formed to create the narrower distal portion of the partition. In further variations, the strip can be angled so as to form a taper.

Figure 44:
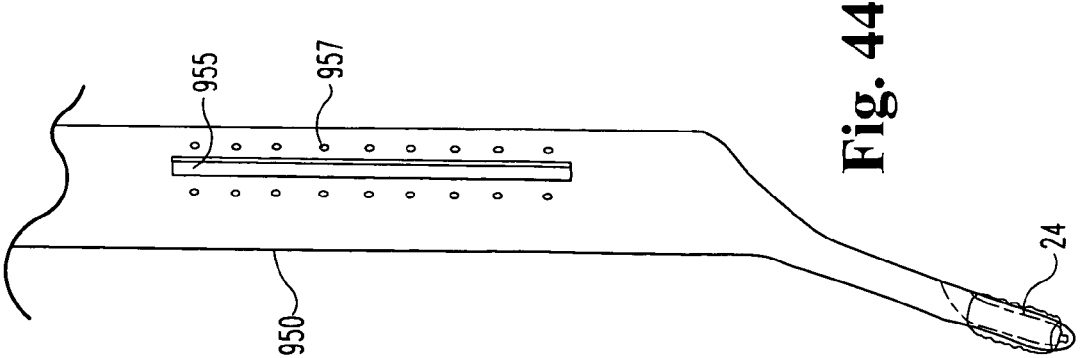
FIG. 44 is a device for forming the slot of prepared tissue of FIG. 43.

Referring to FIG. 44, one mechanism for creating the strip 153*a* of prepared tissue is with device, such as device 950, which has a cautery surface 955 in the shape of the desired strip 153. In use, suction is applied through vacuum holes 957 on either side of surface 955 to bring the stomach wall into contact with surface 955, and surface 955 is activated to cauterize the stomach wall.

Referring now to FIGS. 45-51, another variation on a surgical system for performing gastroplasty is disclosed. In this variation, the surgical system includes an applicator 960 that is inserted into the patient's stomach and aligned along the lesser curvature. The proximal portion (not shown) can be secured to a bite block at the patient's mouth, and the distal portion 24 can be anchored (e.g. in the pylorus) as described above. The applicator 960 has a main lumen (not shown) that extends at least from a proximal entrance to an elongated side working opening 965. With the applicator 960 in position a slicing device 970 and a suturing device 990 may be inserted into the main lumen so as to access the anterior and posterior stomach walls via working opening 965. During the initial insertion of applicator 960 into the patient, a filler block (not shown) may be inserted in the main lumen to fill the opening 965 and provide structure integrity to the applicator 960 and/or provide a smooth surface at opening 965.

Figure 46:
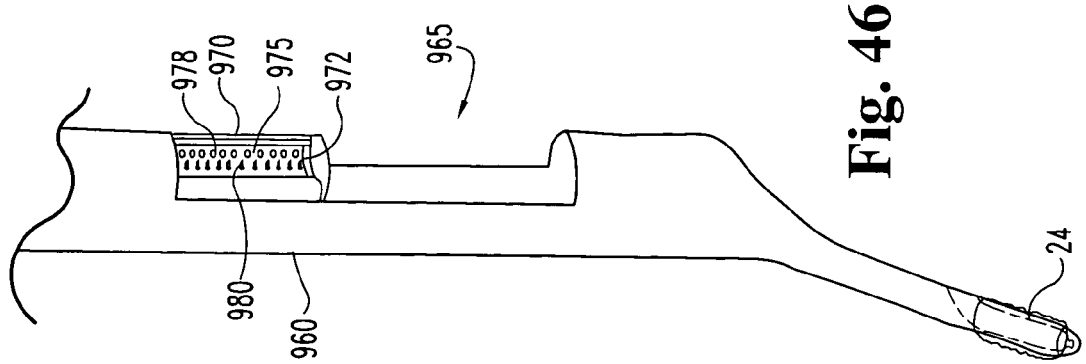
FIG. 46 is a side view of the FIG. 45 applicator with a slicing device partially inserted into its main lumen.
Figure 45:
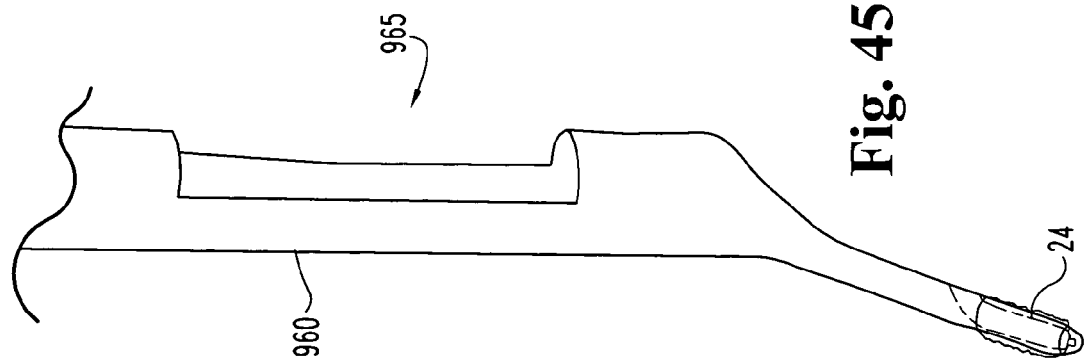
FIG. 45 is a side view of an applicator according to another embodiment.
Figure 47:
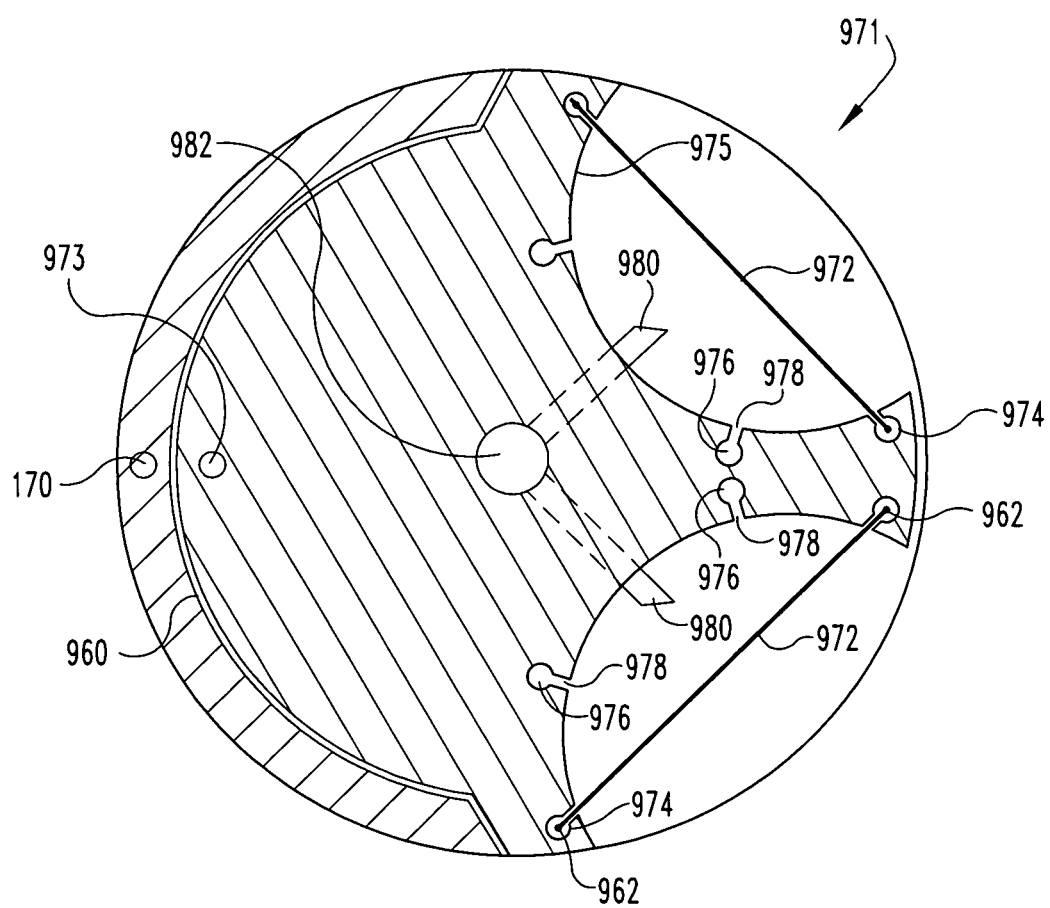
FIG. 47 is a cross section of a slicing device positioned in the working opening of the FIG. 45 applicator.

Referring in particular to FIGS. 46 and 47, a slicing device 970 may be inserted through the main lumen of applicator 960 and used to resect a portion of the anterior and posterior stomach walls to prepare them for being joined (e.g. so as to expose submucosa). The slicing device has two slicing portions 971 for forming strips of resected tissue on the anterior and posterior stomach walls. Each slicing portion 971 has a cavity 975 with a series of vacuum ports 978 and injection needles 980. The injection needles 980 are all coupled to a common injection lumen 982 and a common vacuum source feeds the vacuum ports 978 via a series of vacuum lumens 976. When suction is applied, tissue (not shown) is drawn into the cavities 975, and the force of the suction causes needles 980 to puncture the captured tissue. An adrenaline saline solution may then be injected into the captured tissue via lumen 982. The cross section of lumen 982 may be configured to promote the even distribution of fluid along the length of the slicing portions, for example with the cross section at the distal end being smaller that at the proximal end.

A wire 972 extends across each cavity 975 and has an enlarged head 962 slideably received in channels 974 at each side of the cavity 975. With the tissue captured in the slicing portions 971 (via the vacuum), the operating physician pulls proximally on lines (not shown) coupled to each head 962 to pull the wire 972 through the tissue.

To assure proper positioning during use, orientation wire(s) may be used in orientation wire lumen 973 of the tissue sectioning device 970 and/or in orientation wire lumen 170 of the applicator 960.

With the stomach walls sectioned, tissue sectioning device 970 may be withdrawn and a suturing device 990 inserted into the main lumen of applicator 960. As illustrated, the suturing device is of the type that employs a longitudinally operable needle, but a suturing device having a circumferentially operable needle could be used. Suturing device 990 includes a vacuum lumen 994 for drawing a vacuum in cavity 992 and a needle lumen 995 for driving a suture through the tissue captured in cavity 992. A removable needle capture chamber 996 is provided on the distal side of the cavity 992 to capture the needle and/or the suture once it has been passed through the tissue.

Figure 48:
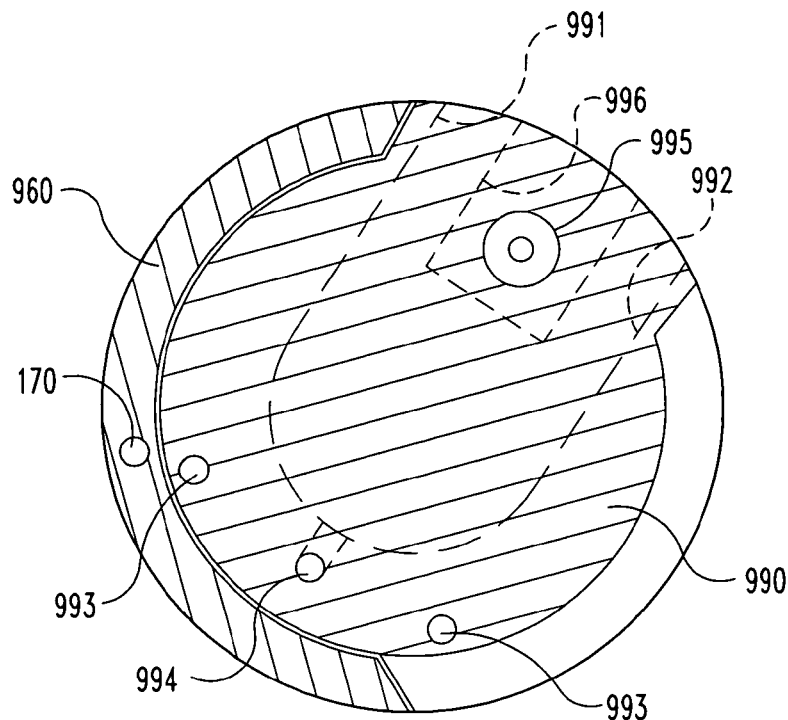
FIGS. 48 and 49 are cross sections of a suturing device positioned in the working opening of the FIG. 45 applicator.
Figure 49:
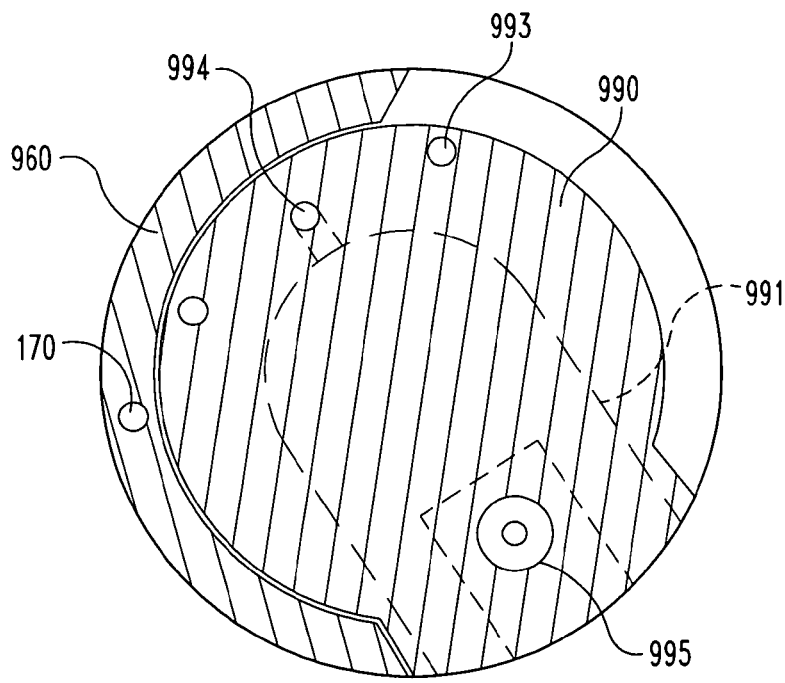

As illustrated, the suturing device 990 is configured to attach a single suture and to be axially rotated within the applicator 960 so as to be disposed towards the anterior or posterior walls, as illustrated in FIGS. 48 and 49. A pair of orientation wire lumens 993 are provided in the suturing device 990 and may be used to rotate the suturing device.

Figure 50:
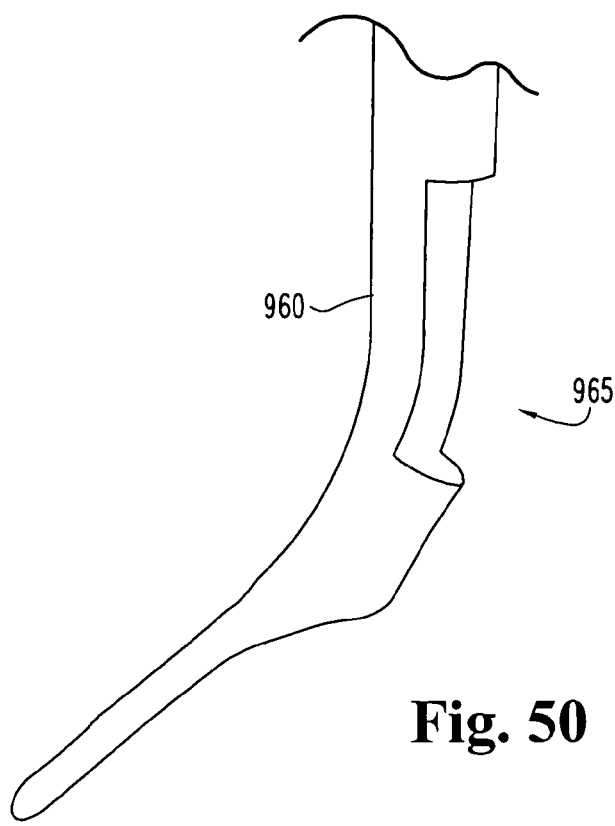
FIG. 50 is a side view of the FIG. 45 applicator positioned with a curve near the distal end of working opening.
Figure 51:
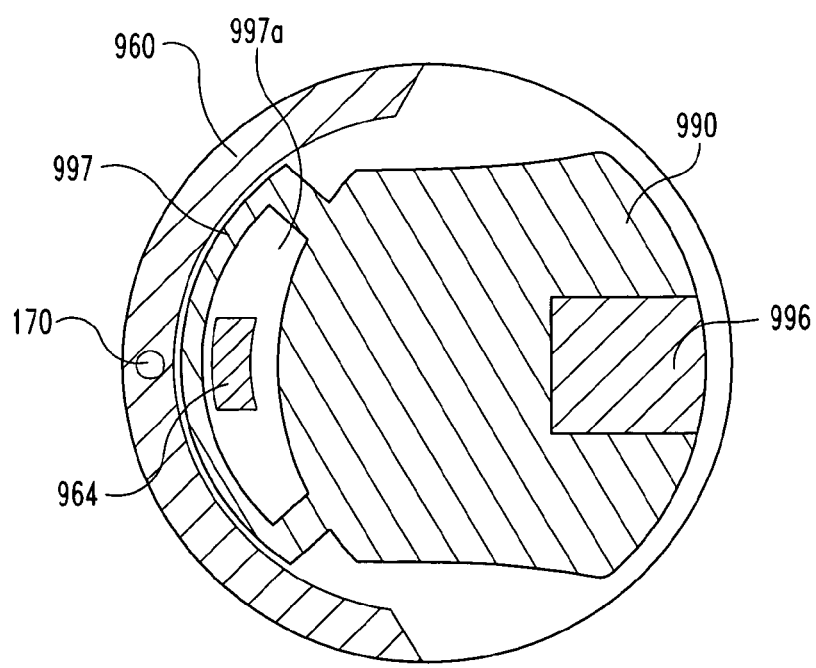
FIG. 51 is a cross section of the distal portion of the suturing device in the FIG. 45 applicator.

With the applicator 960 conforming to the lesser curvature of the stomach, the distal end of the working opening 965 in applicator 960 may be curved during use, as depicted in FIG. 50. To assure that the devices 970 and 990 stay oriented in the main lumen of the applicator 960 while they are being inserted, orientation wires may be used in the orientations wire lumens of the slicing device 970 and the suturing device 990. Alternatively or in addition, the distal portions of the devices 970, 990 may be adapted to engage with the applicator 960 near the distal portion of the opening 965. One such mechanism for accomplishing this engagement is illustrated in FIG. 51, which shows in cross section the distal portion of suturing device 990 engaged with the applicator 960 near the distal end of opening 965. More specifically, a retention member 997 extends from the side of device 990 opposite the suction cavity 991 and receiving chamber 996 and defines a receiving opening 997a. A catch 964 is secured at the distal end of extends on the interior surface of applicator 960 and extends proximally. As the suturing device 990 is advanced towards the distal end of opening 965, catch 964 slides into receiving opening 997a to assure that the suturing device 990 conforms to the curvature of the applicator 960.

As mentioned above, for example in connection with FIG. 35, a suture can be attached to multiple sites by passing a thread carrier back and forth across the suction chamber via a hollow needle. Turning now to FIGS. 52-54, a suitable mechanism for accomplishing this is shown. Suturing section 220 includes a tissue acquisition cavity 222 to which suction is applied by vacuum line 145, an injection needle lumen 160 and a resection device lumen 150 (or alternative the resection may be via 160 and the injection via 150). Referring to FIG. 52, a tread shuttle 254 having a suture thread 246 attached or embedded therein is contained in a hollow needle 240 in a needle lumen on the proximal side of the cavity 222. On the distal side of the cavity, an entrapment section 230 is provided for selectively capturing the thread shuttle 245 and retaining it on the distal side of the cavity 222. The entrapment section includes a member 231 having a ramped cam surface 232 and being biased leftward (per FIG. 52) by compression springs 236.

Before being passed to the distal side (i.e. FIG. 52), the shuttle 245 is retained in the hollow needle 240 via frictional engagement with inside surfaces 242 of the needle 240. The shuttle 245 may also include engagement members 247 (FIG. 53), such as a textured or rubberized surface, for engagement with corresponding features on inside surface 242. To pass the shuttle to the distal side, the distal tip of the hollow needle 240 is advanced across the cavity 222 and a pusher rod 248 slides the shuttle 245 distally against the ramped surface 232. This causes member 231 to move rightward and compress springs 236, and the restoring force of springs 236 frictionally holds the shuttle 245 in the entrapment section 230, as shown in FIG. 53. Engagement members 234 may be provided on member 231 to improve the frictional adhesion.

To bring the shuttle back to the proximal side of the cavity 222, the hollow needle is advanced into the entrapment section 230 over the shuttle 245 and the interior surfaces 242 of needle frictionally grab the shuttle 245. The distal portion of the shuttle 245 can be provided with a tapered surface 249 to facilitate the proper alignment of the needle 240 over the shuttle 245, and the needle 240 has a distal slot 243 for accommodating the free end of the thread 246. The entrance 238 to the entrapment section is also tapered to facilitate smooth insertion.

Other mechanisms for holding the thread shuttle in place (inside the hollow needle and/or in the entrapment portion) may be utilized in place of or in addition to the friction fitting described above. For example, magnets, shape memory materials or mechanical latches can be used to supplement or replace the friction pads on the thread shuttle and the inside of the hollow needle. In one particular example, the thread shuttle includes magnetic material and the entrapment section applies a magnetic force to selectively capture the thread shuttle. An electromagnet or a moveable permanent magnet may be employed in the entrapment section to selectively provide the magnetic force used to capture the thread shuttle. In another example, an entrapment mechanism may be constructed from a shape memory material that selectively engages the thread shuttle when heated, for example by an electrical current.

A variety of other suturing arrangements may be advantageously employed for joining the anterior and posterior walls, and reference is made to the alternative patterns depicted in U.S. Ser. No. 60/757,694 filed Jan. 10, 2006 and the use of one or more curved or transverse needles therein, for example for the joining of excised strips via a continuous thread in an ascending corkscrew pattern. For example, a device having multiple transverse curved needles along an elongated suction cavity (like cavity 975 in FIGS. 46 and 47) is envisioned. The series of needles may be constructed to be simultaneously or successively activated to pass sutures through tissue that has been captured in the elongated suction cavity. Such an arrangement would allow multiple sutures to be attached in a row with a predetermined spacing.

Figure 55:
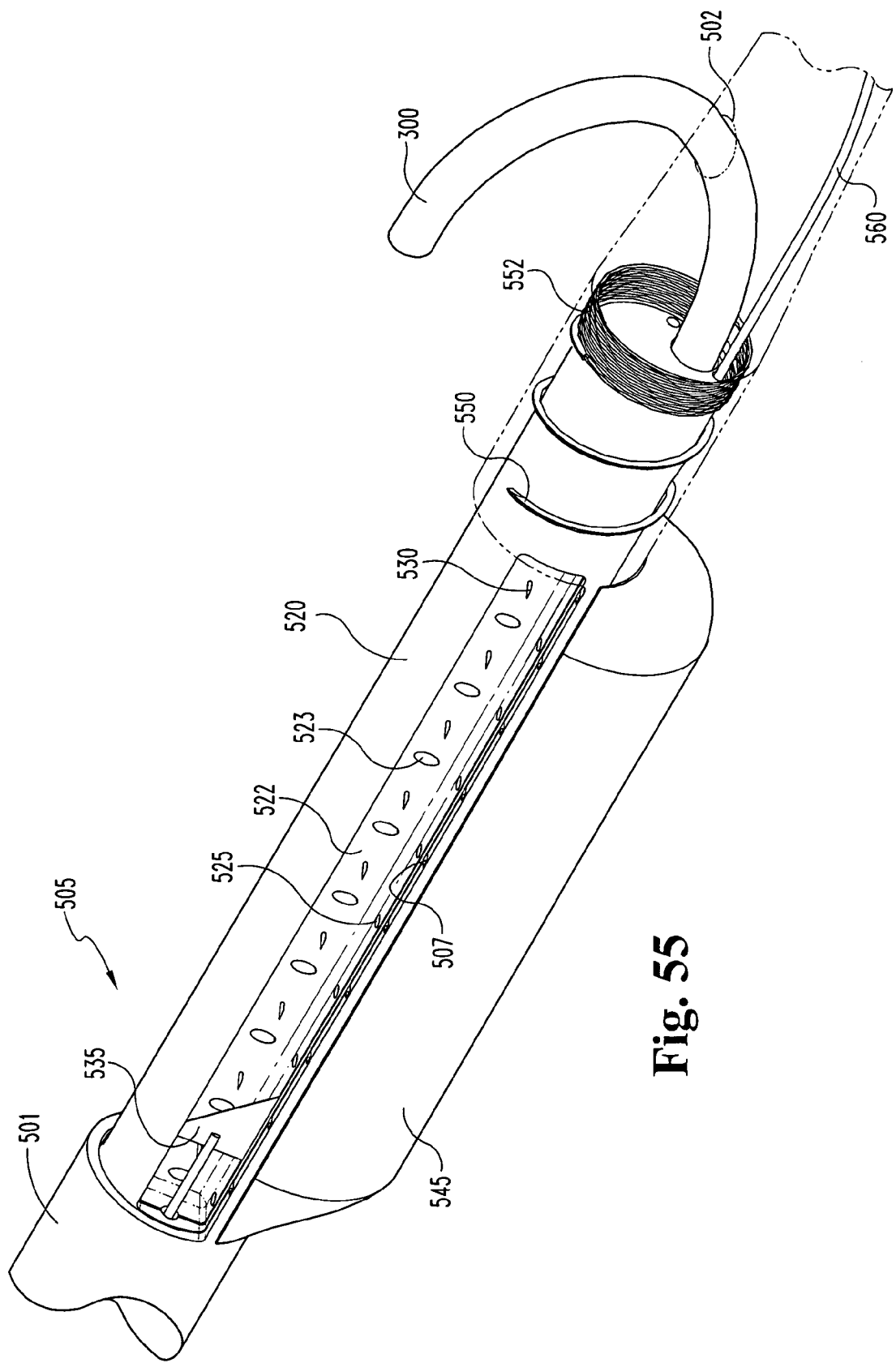
FIG. 55 is a perspective view of an alternative embodiment incorporating an expandable spacer and a short helical needle. The distal portion of the outer elongated body, or keeper, is shown in phantom lines to illustrate the detail within.
Figure 56:
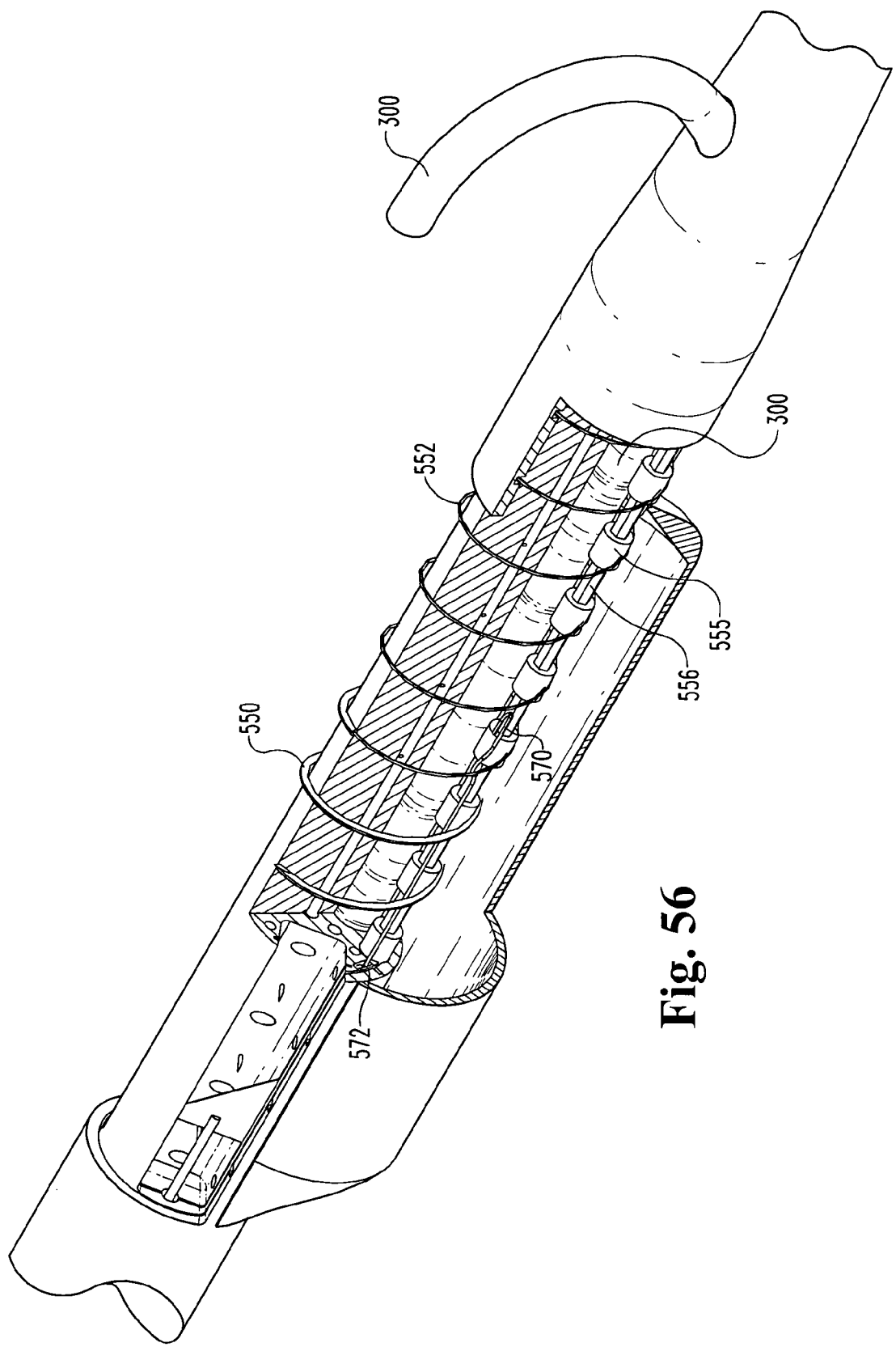
FIG. 56 is a cutaway in partial section corresponding the FIG. 55 embodiment and view.
Figure 57:
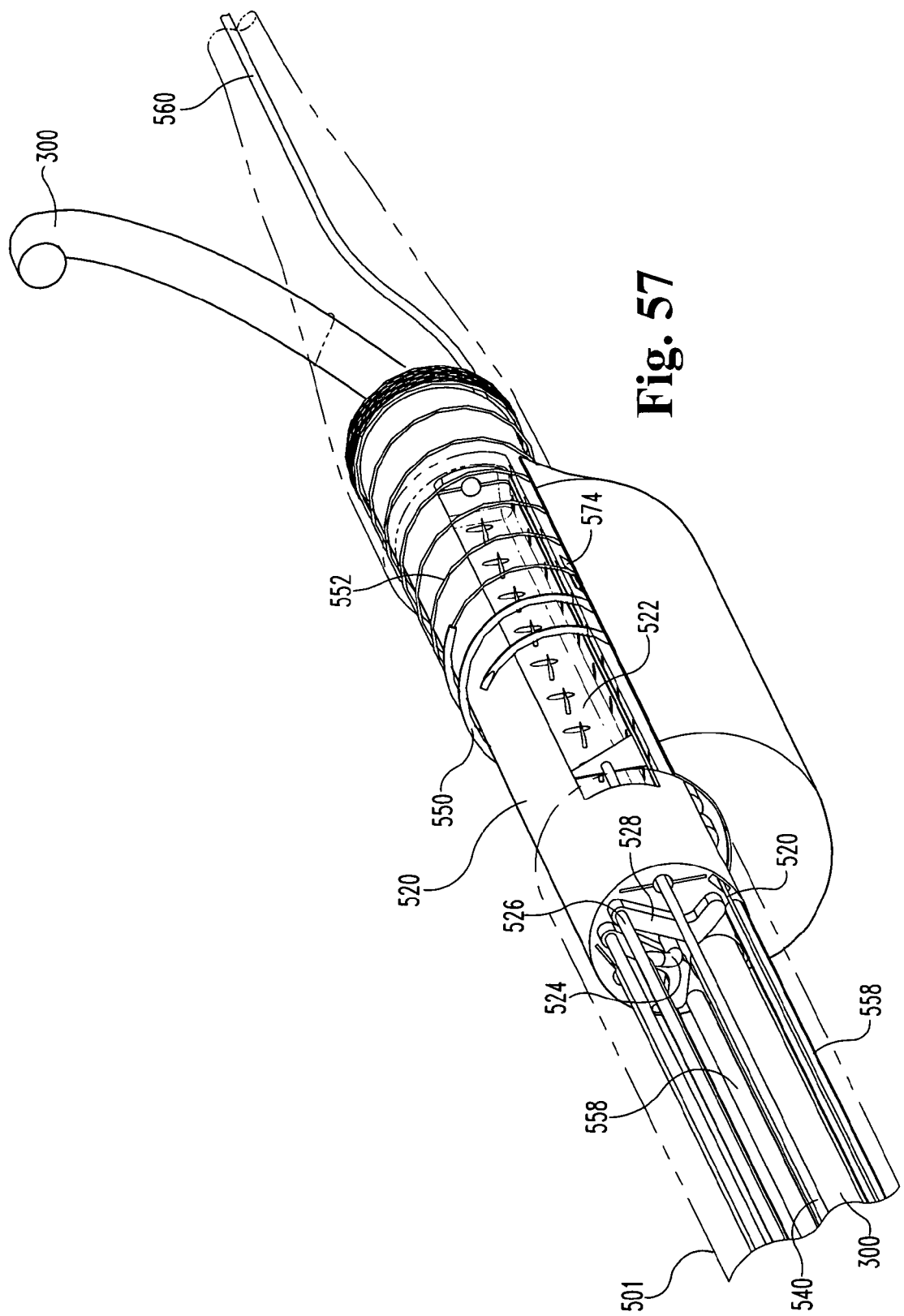
FIG. 57 is a perspective view looking towards the distal end of the FIG. 55 embodiment with the keeper shown in phantom lines.

Referring now to FIGS. 55-57 an alternative embodiment incorporating an expandable spacer and a short helical needle is depicted. An elongated body or keeper 501 has a window section 505 for allowing the working components, in this case device 520, access to the stomach walls. Device 520 includes a pair of elongated suction cavities 522 for capturing tissue via suction applied to ports 523, 525 along the bottom and sides of cavities 522. A suction lumen 526 delivers a vacuum and a manifold 528 serves to allocate the vacuum pressure to the ports 523, 525. Lumen 524 provides the infusate into injection needles 530 to inject the captured tissue, and once injected, an excision blade 535 is driveably distally via a driving rod 540 to excise the captured and infused tissue.

A helical needle 550 carrying a suture tread 552 is driven along its axis in a distal to proximal direction by two sets of rollers 555, which are driven by a pair of driving rods 558. Rollers 555 are evenly spaced based on the pitch of the helical pitch of the needle 550 and connected by narrower diameter connecting portions 556 which enhance the flexibility of the device. As illustrated, needle 550 includes two complete helical turns and thus would remain in contact with at least four rollers at all times as it is advanced proximally up its path, contributing to a stable and predictable path of the needle through the tissue. As an additional aid to the stability and guidance of needle 555, the inner surface of keeper 501 is provided with guiding grooves in the shape of the intended needle path. In addition to or in place of conventional needle materials, to enhanced workability, the helical needle 550 may be constructed of a superelastic material, such as Nitinol. The engaging surfaces of rollers 555 and/or needle 550 may be roughened and/or each may be provided with teeth to enhance the engagement between rollers 555 and needle 550.

An endoscope 300 extends though the keeper 501 and device 520 and exits through opening 502 distal to window 505 and may be used to visualize the procedure and spot issues that may develop. As illustrated, an emergency wire catch 570 extends through lumen 572 of device 520 and may exit at one or more openings 574 to address problems that might be so identified, for example to address snags or to pull any necessary slack in the suture thread. Alternatively or in addition, instruments (not shown) may be inserted through the working channel of the endoscope for this purpose.

A balloon catheter 560 extends through the keeper 501 and exits through the distal end of the keeper (not shown). A balloon on the distal end of the cathether (see FIG. 64) is anchored in the pylorus. An inflatable balloon 545 is provided along the length of the working section of the keeper 501 and may be inflated after insertion into the stomach to increase the effective diameter of the keeper. In use, the balloon 545 is positioned toward the lesser curvature and, with tension applied to the catheter 560, the keeper is biased into the desired position. Careful selection of the outer diameter of the keeper and/or control of the same via the balloon 545, together with anchoring and positioning as described herein, facilitates creation of a lumen of the desired size and shape.

In it to be appreciated that, as illustrated, the axis of the helix is generally coaxial with the axis of the keeper 501. Offset configurations and configurations wherein a portion of the helixal path extends outside the outer dimension of keeper 501 are also contemplated. Generally useful confugrations will typically involve the axis of the helical path residing within the local outer dimensions of the keeper 501.

Additionally, as illustrated, side suction ports 525 are located in cavity 522 on the same side of (i.e. below) the resecting plane defined by the excision blade 535 as are bottom ports 523. As a result, as the captured tissue is excised, ports 523, 525 may both be beneficially used to retaining the excised tissue, but their usefulness in retaining the unexcised tissue is substantially reduced. Placing the suture before or during the excision is one mechanism to address this issue. Alternatively, or in addition, side ports 525 may be located above the tissue excision plane.

In a still further variation, side ports are above the tissue excision plane and made controllable independent of the lower ports. Separate control of the suction cavities would allow, for example, the lower ports to hold onto the excised tissue while the side ports release the tissue.

In a still further variation, mechanical clamping members may be provided along the suction cavities 522. Such clamping members may be used to supplement or replace the acquisition and retaining function of the cavities 522.

Figures 58, 58A:
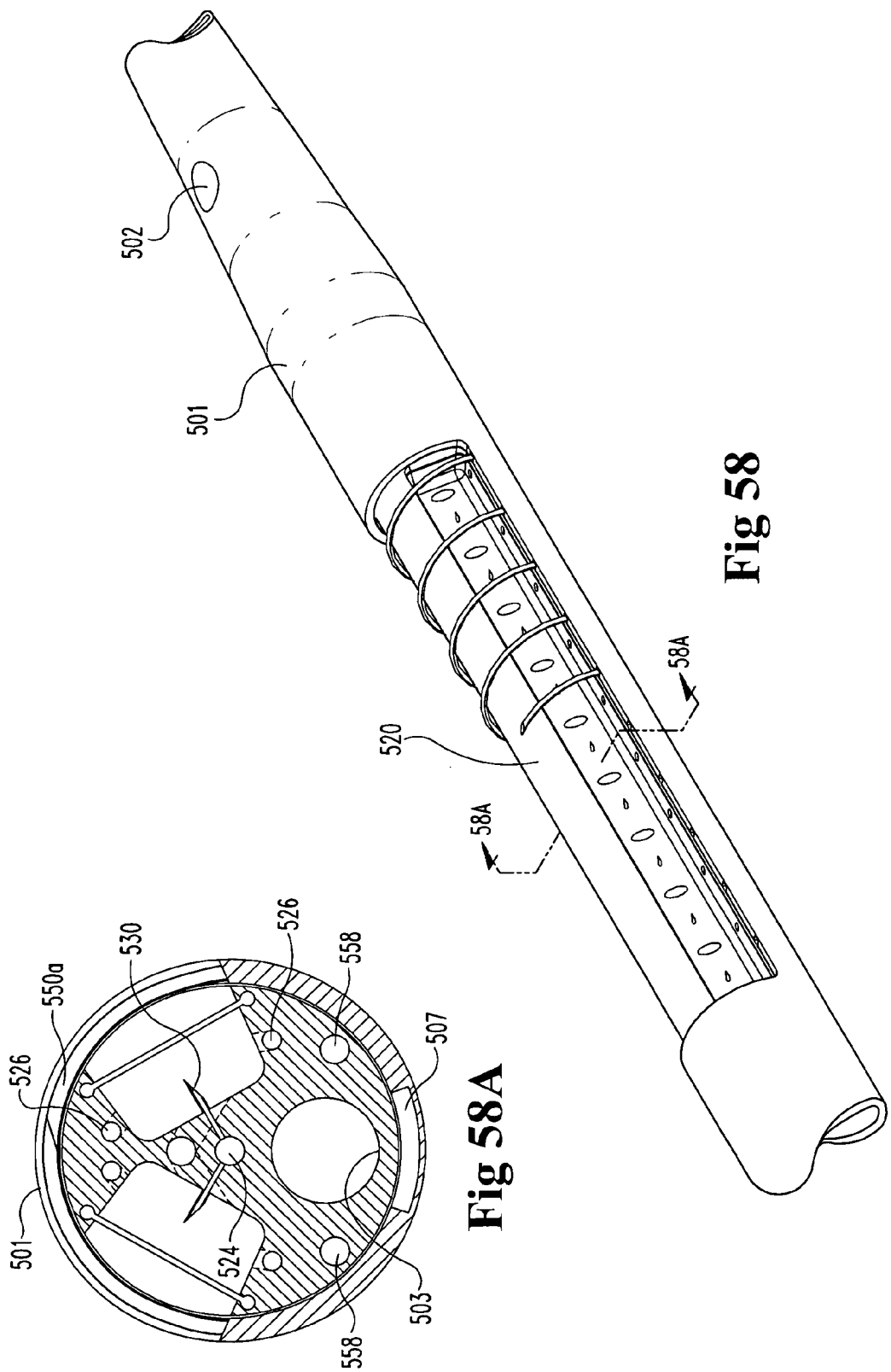
FIG. 58 is perspective view of an alternative embodiment using a longer helical needle.
FIG. 58A is an end sectional view along the line indicated in FIG. 58.

FIGS. 58-60 illustrate an embodiment similar to that depicted in FIGS. 55-57 save the use of a needle with more turns of the helix and the removal of the inflatable balloon 545. FIG. 59 corresponds to the keeper 501 as depicted in FIG. 58 with the internal helical needle and the internal tissue capture, excision, and needle activation components removed and shown in FIG. 60. FIG. 58A shows the relative size and orientation of the various lumens. By way of reference, in one embodiment, the endoscope lumen 503 may be sized to accommodate a 5 mm endoscope and the overall outer dimension of the keeper may be in the range of 15-25 mm, for example about 20 mm not including any expansion provided by the expandable balloon 545.

FIG. 61 is a perspective view of an alternative configuration for the internal tissue capture, excision and needle activation components for use with a keeper such as keeper 501, with additional details of the needle activation shown in FIG. 62. The tissue acquisition and sectioning components of device 350 operate identically to those of device 520 save that the excision blade 370 is operated by pulling a pair of cords 372 attached to the outer edges of blade 370 rather than pushing a centrally mounted actuating rod 540.

The suture activation of device 350 is provided by a shuttle 360 slidably disposed in device 350. The endoscope lumen 503 and a pair of needle actuation lumens 358 are provided in the shuttle 360. Referring to FIG. 62, rods 368 extend through lumens 358 and are coupled to rollers 364 which drive needles 368 and 369 back and forth across the suction cavities.

Figure 63:
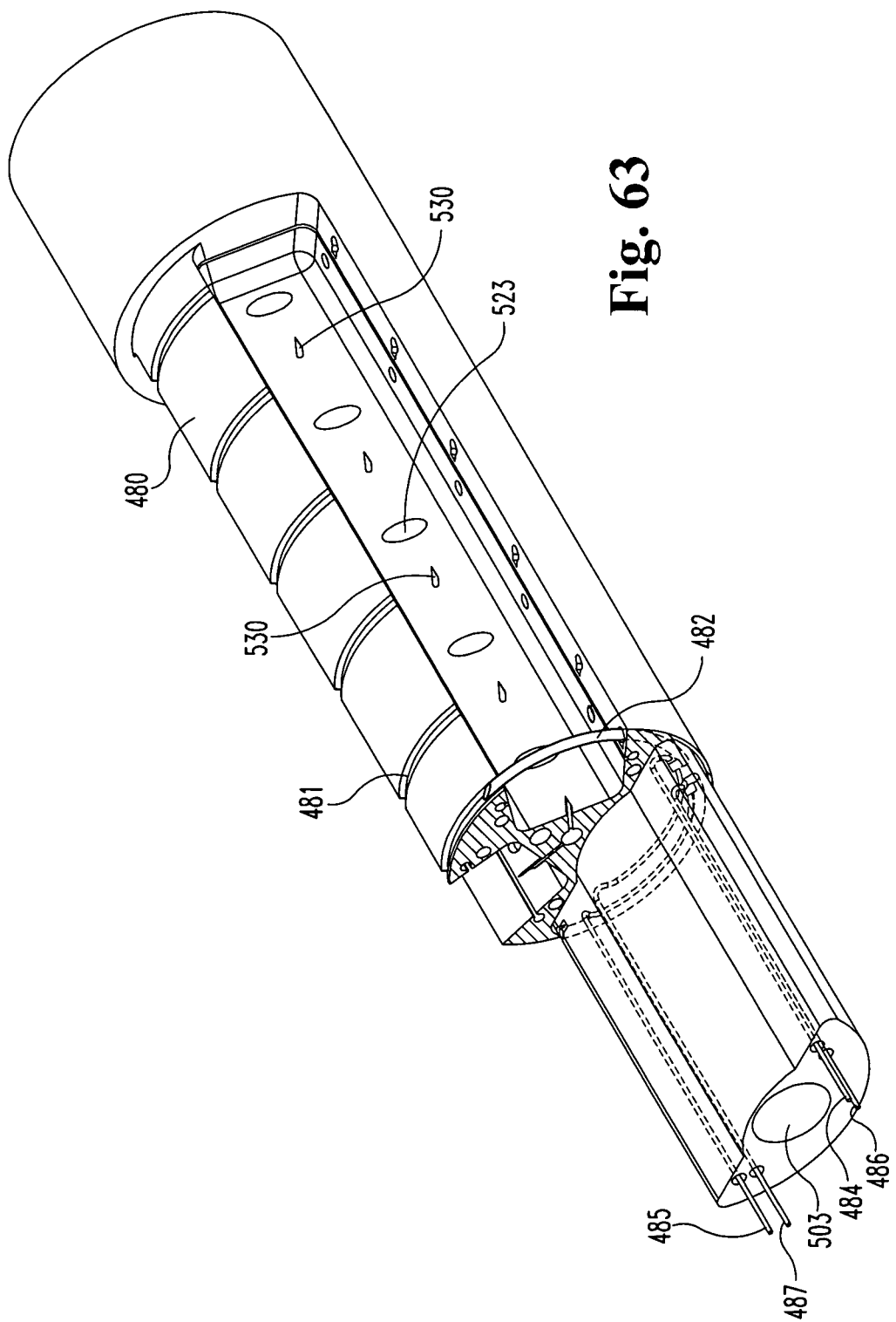
FIG. 63 is a cutaway view of an alternative shuttle configuration for needle activation via pull wires for a slideably disposed shuttle.

In place of rollers, needles may be advanced back and forth across the suction cavities via pull wires 484, 485, 486, 487 as depicted with respect to device 480 of FIG. 63, which may also be used with keeper 501. For example, as depicted, wires 484 is pulled proximally to advance needle 482 across the cavity, and wire 487 is pulled to bring needle 482 back into the shuttle. Device 480 includes a series of channels 481 in the bridging area dividing the suction cavities. The channels 481 may be used as places to exchange a thread carrier between the right side and left side needles, either directly or via a drop-off pick-up arrangement. Alternatively, applying sutures via a removable shuttle facilitates the reloading of needles for outside the body, as described above.

Figure 64:
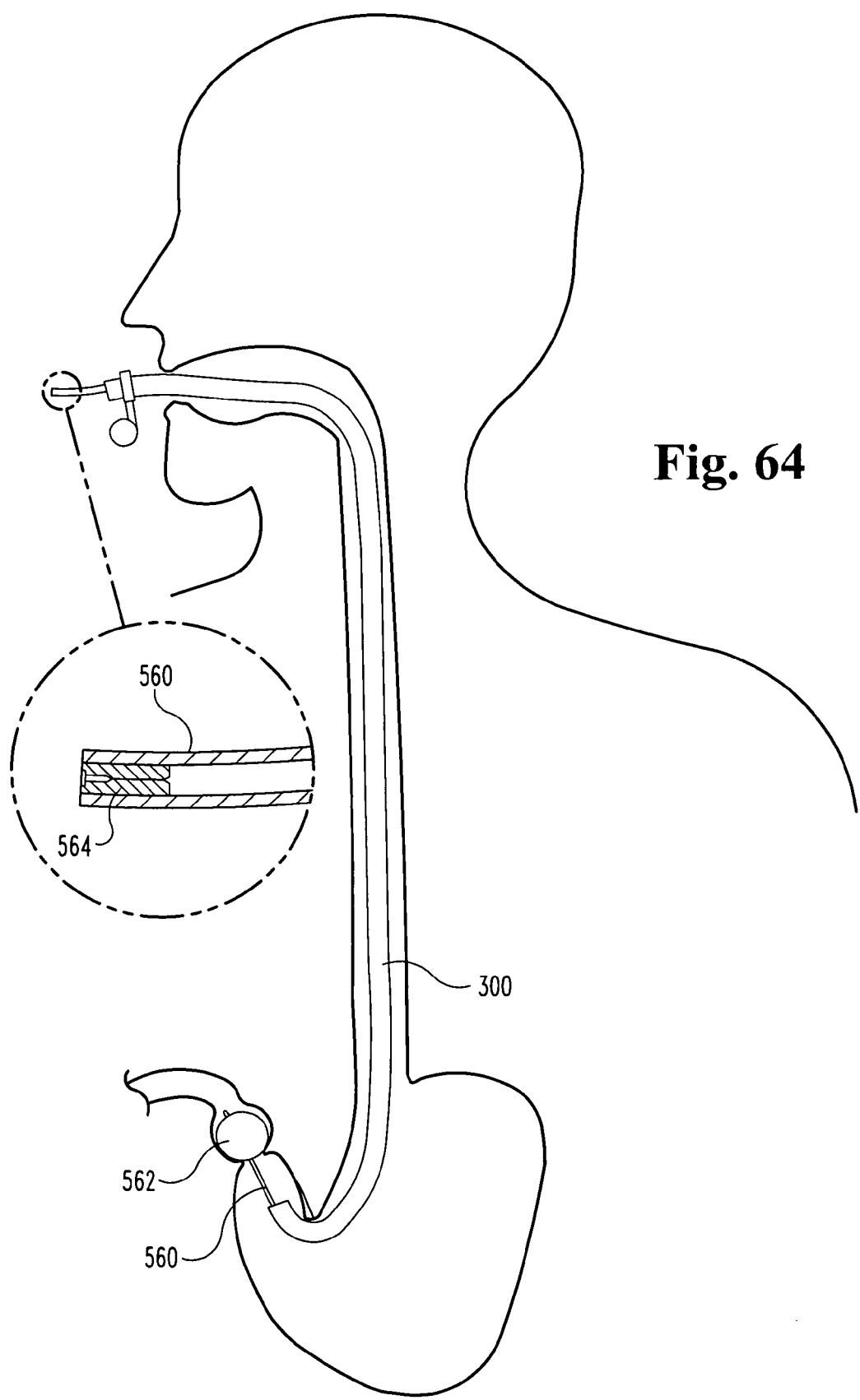
FIG. 64 is a schematic illustration of an anchoring balloon catheter extending through the working channel of an endoscope and with the anchoring balloon inflated in the duodenum and showing detail of the self closing valve at the proximal end of the catheter.

FIG. 64 is a schematic illustration of an anchoring balloon catheter extending through the working channel of an endoscope and with the anchoring balloon inflated in the duodenum and showing detail of the self closing valve at the proximal end of the catheter.

FIGS. 65A-E schematically illustrate the performance of a gastroplasty procedure. The procedure begins with the placement of the anchoring balloon 562 via the working channel of endoscope. The endoscope is withdrawn leaving the balloon in place and the keeper is backloaded over the proximal end of the catheter. The endoscope is then inserted through the keeper. Under visualization of the endoscope and with the assistance of the expandable positioning balloon and/or the anchoring catheter, the keeper is positioned against the lesser curvature and captures portions of the anterior and posterior walls in the suction cavities.

Figure 65A:
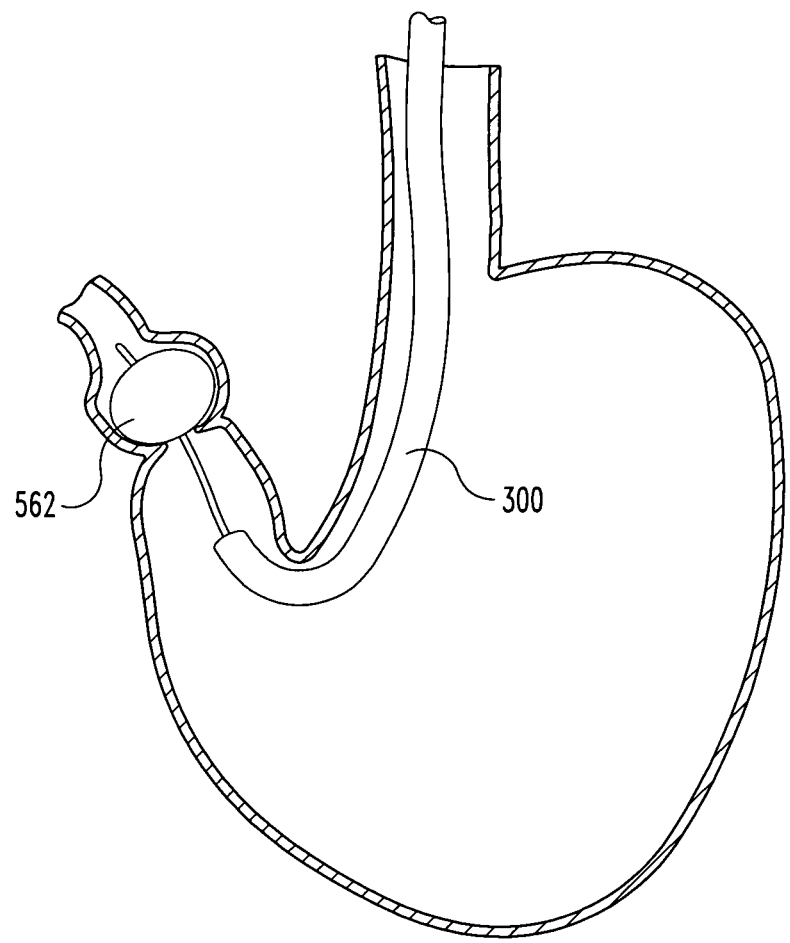
FIGS. 65A-E schematically illustrate exemplary stages of a gastroplasty procedure beginning from the placement of the anchoring balloon as shown in FIG. 64.
Figure 65B:
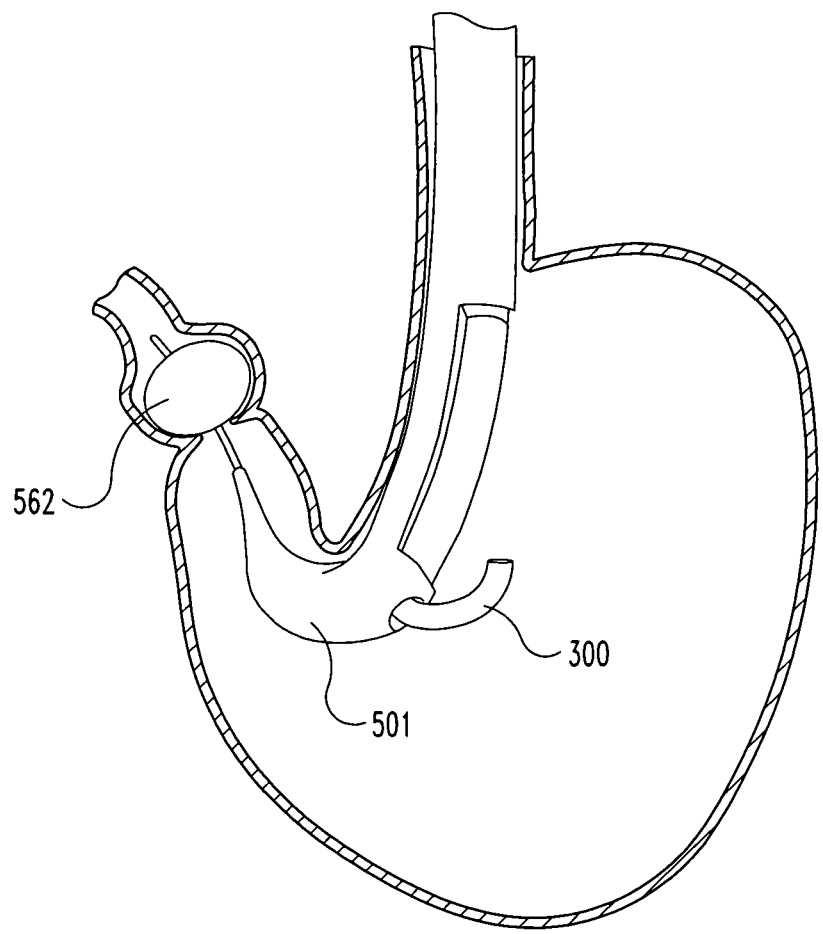
Figure 65C:
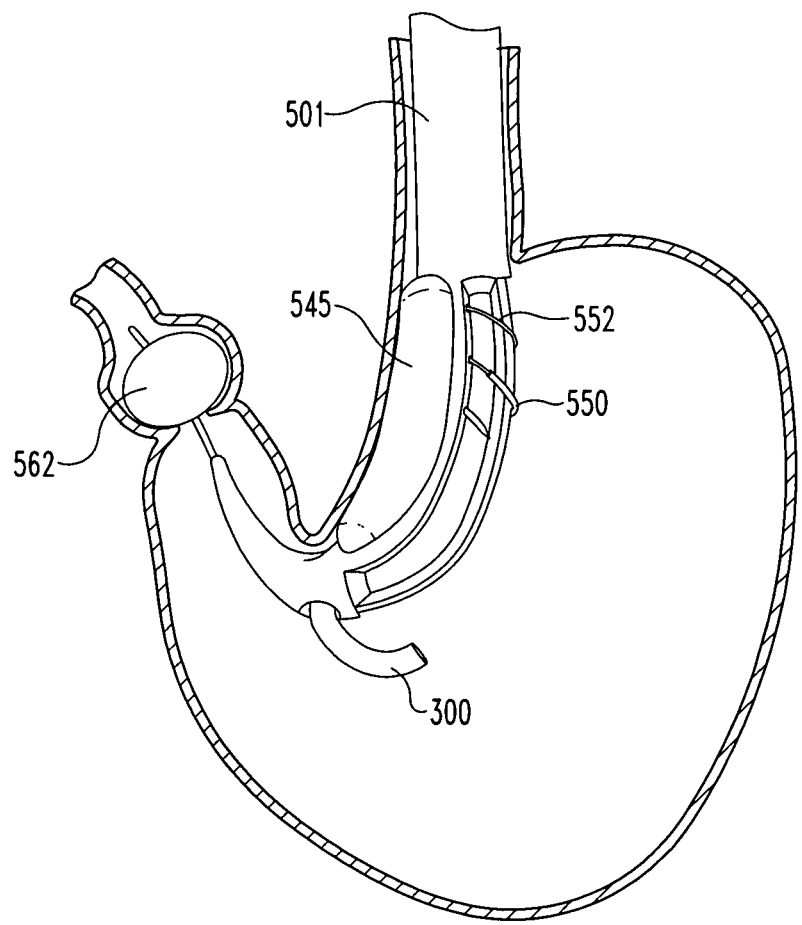
Figure 65D:
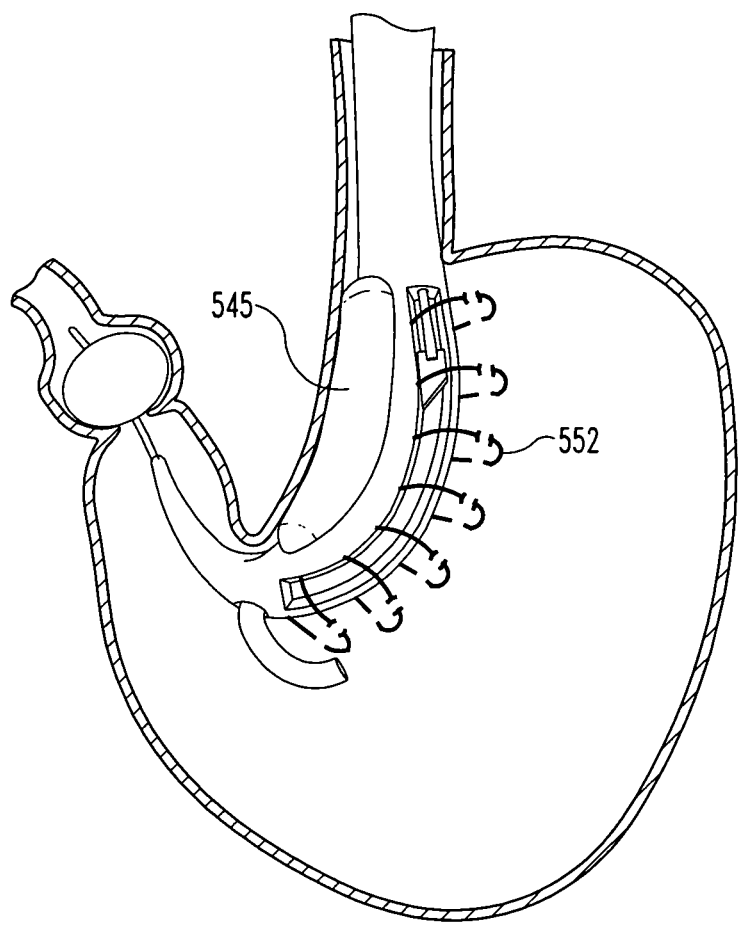
Figure 65E:
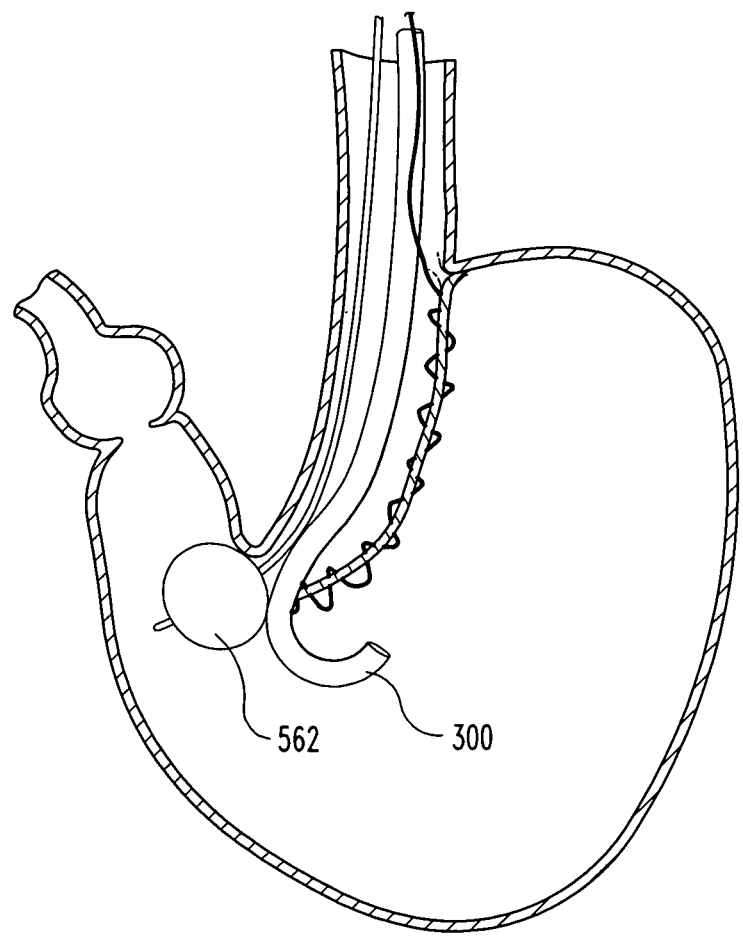
Figure 66:
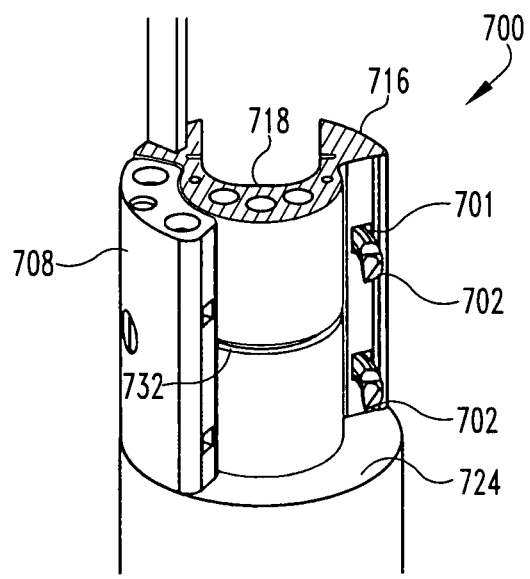
FIG. 66 is a perspective view of the working portion of a device incorporating a needle activation mechanism that includes a shuttle operated by pull wires (not shown).

The helical needle is then used to apply a suture to the tissue portions, which is shown in FIG. 65C in a proximal to distal direction. The tissue is excised after an epinephrine injection, and then it is released with the sutures attached. The position balloon 545 on the keeper 501 is deflated and the working components (e.g. the tissue acquisition and excision components) are slid proximally so as to be removed from the working window. The keeper may then been removed and the helical suture pulled tight, e.g. by using the working channel of the endoscope to grasp the distal end of the helical suture while pulling the proximal end proximally. The anchoring balloon 562 is then repositioned at the distal opening of the newly created lumen (or pouch) in the stomach. With the endoscope positioned on the outside as shown in FIG. 65E, the lumen is filled with liquid, such as methlyene blue, such the absence of any leaks may be visually determined.

One potential complication in creating a leakless seam is that, while in the middle of the stomach one is joining opposing walls together, near the esophageal junction (i.e. where the seam meets the esophagus) the "walls" start to resemble "ceilings." FIGS. 38 and 39 depict one approach to avoiding leaks where the seam meets the esophagus involving excising this "ceiling" tissue. The excision may be accomplished by adding an arch section 592 to effectively join the elongated suction cavities 522 on the left and right sides of the device. In use, this arch section would be positioned where the seam is to meet the esophagus. An arch cutter 594, such as a wire or rotating blade, may be configured to cut tissue acquired in this arch section. Alternatively the blades or excision wires used to excise along the length of the channels may begin or end its path by cutting the arch. For example, two blades can act together as one to cut the arch portion and then split and follow their separate paths in the elongated cavities.

Referring now to FIGS. 66, 67 and 68A-68C, the working portions of a device 700 illustrating an alternative suture activation mechanism is depicted. Device 700 includes curved needle 702 actuated by shuttle 708. (As illustrated there are two needles 702 but it is to be understood that a single needle or an array of needles may be utilized) Pull wires (not shown) are attached to rod 712 and used to move shuttle 708. The pull wires extend through lumens 728, 729, and each lumen opens into channel 732, which, in conjunction with the bounds of recess 724 generally define the direction of travel of shuttle 708. More specifically, as the operator pulls proximally on the pull wire in lumen 728, shuttle 708 receives a rotational force in the clockwise direction (as per FIG. 68). Conversely, tension applied to the wire in lumen 729 pulls shuttle 708 in a counterclockwise direction.

Shuttle 708 is constructed to be selectively engaged with either end of needle 702. Recesses 704, 706 on needle 102 receive a biased plunger (e.g. a ball detent) that is installed into shuttle 708 and held in place via set screws 714. Needle 702 is also sized to abut bar 712 when the plunger is engaged in recess 704 or 706. The abutment of needle 702 to bar 712 serves as a positive stop to needle 702 when it is being engaged with shuttle 708 and/or when shuttle is acting to push the needle (e.g. going from FIG. 68A to FIG. 68B).

Needle 702 also includes a slot 705 that selectively aligns with a longitudinally operated locking bar 734. Locking bar 734 is biased distally by spring 735 and engages with slot 705 to lock needle 702 into its relative position of FIGS. 68B and 68C. With locking bar 734 fixing needle 702 in position (FIG. 68B), the wire in lumen 729 may be pulled with sufficient force to overcome the retaining force of the ball detent and thereby disengage shuttle 708 from needle 702. Shuttle is then free to be engaged with the other end of needle 702 (e.g. moved from 68B to 68C).

In typical operation, device 700 is inserted through an applicator (e.g. applicator 960) and anchored in position via a anchoring device (e.g. balloon catheter) inserted through lumen 727. Once in the position of FIG. 68A, tissue from one stomach wall (e.g. anterior or posterior) is acquired in cavity 718 via suction applied through suction lumen 725. Infusate is injected into the acquired tissue (not shown) via lumen 726 and needles 722, and tissue is excised via an appropriate cutting device guided in excision slot 719. While tissue is acquired in cavity 718, shuttle 708 is operated to push needle 702 through the acquired tissue to the position of FIG. 68B. Locking bar 734 engages slot 705 to hold needle in position, and shuttle 708 is transferred to the other side of needle 702 (as per FIG. 68C). Shuttle 708 may then be used to pull needle 702 entirely though cavity 718 such that the back end of needle 702 is entirely through tissue and into channel 701. Throughout this process, a suture thread is secured to needle 702 via holes 703 and thus it has now been inserted completely through the captured tissue section. Suction is released and the capture tissue falls away from cavity 718 with the suture thread inserted.

Figures 68A, 68C:
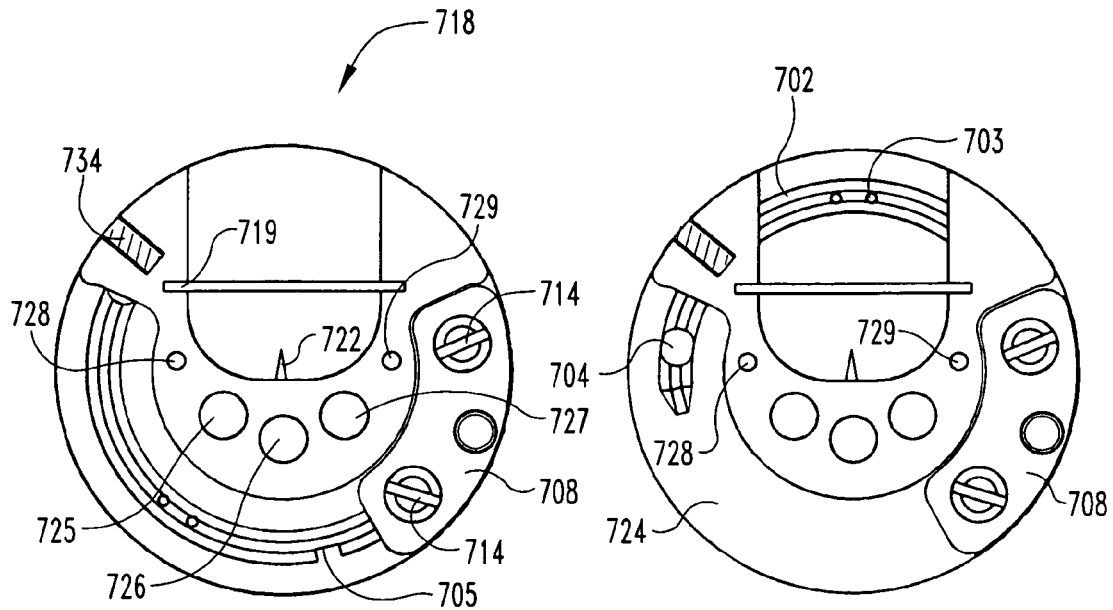
FIG. 68A-C are end views of the FIG. 66 device illustrating different positions of the needle activation shuttle to both push and pull the needles across the suction cavity with the section lines of FIG. 66 removed for clarity.
Figure 68B:
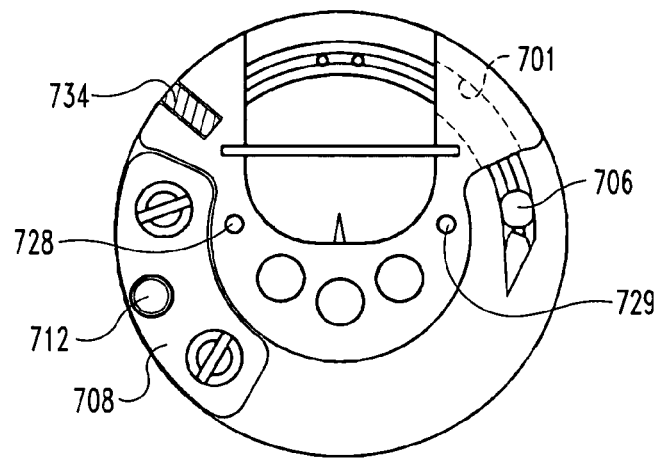

With no tissue in cavity 718, the process is reversed (i.e. 68C to 68B to 68A) to get needle 702 into the position of FIG. 68A. Keeping the device 700 in the same longitudinal position, device 700 is rotated to the opposing stomach wall and the process repeats to apply the suture to tissue on the opposing stomach wall.

As noted above, one end of the suture is attached to needle 702 via holes 703. The other end of the suture extends proximally outside device 700 (but inside applicator) to the operating surgeon. Particularly when an array of needles (e.g. 3-10 needles) are employed, the free ends of the sutures may be organized outside the patient, for example via mounting on a plastic plate (not shown) having appropriate coding (e.g. color, numbers, letters) to indicate the relative position of the respective sutures. Device 700 is then withdrawn and the operating surgeon can obtain the remaining ends of the sutures from the needles 702. Appropriate sutures are then tied together with a knot or knotting element (not shown) which is advanced down to the tissue level to bring the tissue sections together. Suitable knotting elements that can be used in this fashion are known and generally comprise a cylindrical element that is inserted over the sutures (e.g. plastic or metal cylinder) and slid down to the tissue level via a catheter or other suitable pusher. Then, once the tissue has been placed in sufficient approximation, the cylindrical element is crimped, plugged or otherwise secured in place on the sutures. The free ends of the sutures are then cut in any conventional fashion. Examples of suitable knotting elements and devices useful for installing the same are shown in U.S. Pat. No. 5,755,730 and U.S. Pat. No. 5,548,861.

As illustrated and described, the needle punctures tissue in the same direction each time (i.e. clockwise as per FIG. 68A) and thus is configured with only one sharp end. In the illustrated application, such one way application through a captured anterior and then posterior is believed to assist in aligning the excised portions in apposition once a pair of sutures are tied together and pulled tight. It may be desirable (in this or in other applications) to puncture tissue in both directions, in which case needle 702 can be made sharp at both ends.

In another variation, a whip stitch running distally to proximally can be created using device 700 configured with a single needle. After applying a suture to the anterior and posterior walls at one longitudinal position as described above, the single needle device would simple need to be repositioned proximally and the process repeated to apply another stitch.

Figure 67:
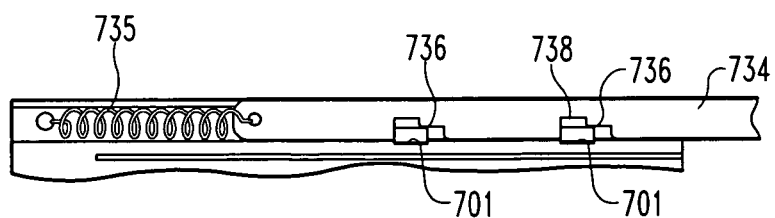
FIG. 67 is a close up cutaway view illustrating the locking bar in the FIG. 66 device.

As shown in FIG. 67, locking bar 734 includes a recess having two different stages or depths. The shallow recess 736 is sized to engage into the locking slot 705 of needle 702. As explained above, to unlock needle 702, bar 734 is pulled proximally, and deeper recess 738 is sized to accommodate the main body of needle 702 in its unlocked state. Because bar 734 is biased proximally, the transition region between recesses 736, 738 may be used to apply distal pressure to needle 702. This distal pressure may serve to assist in keeping needle 702 in alignment during its operation.

As illustrated, device 700 does not show a separate endoscope lumen, but it is to be understood that if it is desired to have an endoscope extend distally through the illustrated portion of device 700, a separate endoscope lumen may be provided. Alternatively, device 700 may be inserted thorough an applicator that accommodates both an endoscope and device 700. In addition, it may be desirable to provide a sheath (not shown) around device 700 to provide a smooth outer surface (e.g. to cover the edges due to the presence of shuttle 708) and facilitate insertion of device 700 (by itself or through applicator). Such a sheath can provide a location for accommodating such other devices.

As will be appreciated by those of skill in the art, what has been disclosed includes a novel method for joining stomach walls to reduce the interior volume of the stomach utilizes a surgical system comprising an elongated body or keeper and at least one working member operably associated with the elongated body, the working member including first and second suction cavities. The method may involve capturing an anterior portion of the stomach wall with the first suction cavity and applying a first suture thereto, capturing a posterior portion of the stomach wall with the second suction cavity and applying a second suture thereto, and then drawing the first and second sutures together to join the anterior and posterior wall portions. During some or all of the capturing, the elongated body may be aligned along the lesser curvature of the stomach by any of the anchoring and/or orientation techniques described herein. Preferably, though not essentially, the anchoring is via a balloon catheter with desired orientation imparted to the device via tension applied to the balloon catheter.

The working member may be slideably disposed within the elongated body capture the stomach wall portions through at least one opening along the length of the elongated body.

The elongated body may be used to occlude the proximal portion of the stomach and a balloon used to occludes the distal portion of the stomach. Then, gas may be fed into or removed from the stomach to expand or contract the stomach walls. Similarly, the balloon may be moved into position to plug the lumen once it is created to check for leaks in the seam.

Prior to drawing the sutures together the captured portions of the stomach walls may be partially excised, for example via a cutting device in the suction cavity. Prior to excision, an infusate may be injected, for example via injection needles in the suction cavities. Suction may be controllably applied to the upper and lower portions of the suction cavities independently, for example such to hold the unexcised tissue when the lower portion of the tissue is being cut away.

What has also been disclosed is a novel method for joining stomach walls to reduce the interior volume of the stomach using an elongated body having a proximal end extending from a body orifice, at least one working member operably associated with a working portion of the elongated body, and an anchoring device distal to the working portion for orienting the elongated body along the lesser curvature. The at least one working member may define at least one suction cavity and excision device for capturing and excising and the method may include capturing and excising an anterior portion of the stomach wall, capturing and excising a posterior portion of the stomach wall with the suction cavity and excision device, then joining the excised anterior and posterior wall portions. Infusate may be injected to prepare the tissue for excision swelling or promote healing and the suction may be controlled across portions of the cavities. During some or all of the procedure, the elongated body may be oriented along the lesser curvature.

The excised anterior and posterior wall portions may be joined with a plurality of sutures applied to the captured and excised anterior and posterior wall portions to create a modified lumen in the stomach. In one form, tissue is captured in two elongated suction cavities and a plurality of sutures are applied via a needle carrying a suture thread along a generally helical path. The generally helical path may have an axis inside the elongated body and/or helical grooves in an interior surface of the elongated body may define the path.

After excision and application of the sutures, the captured wall portions may be released and allowed to fall away from the device and then drawn together by drawing the suture tight. Depending on the device orientation, if the thread is wrapped around the device it may be necessary to slidingly withdraw the suturing device after applying the sutures.

If the cross sectional area of the device is not ideal for the particular application or merely as a mechanism for improving the orientation of the device, a spacing member along the length of the elongated body may be employed. The spacing member may be expandable to increase the effective cross sectional area of the elongated body at any point along its length but would typically be used against the lesser curvature. An expandable bladder or balloon may be used. As an additional mechanism for retaining the tissue captured in the suction cavities, one or more clamping members may be employed to grasp the tissue in the cavity.

What has also been described is a novel method for joining stomach walls to reduce the interior volume of the stomach utilizing a surgical system inserted inside the stomach via the esophagus. The system may include an elongated body having a proximal end extending from a body orifice and at least one working member operably associated with a working portion of the elongated body, the at least one working member comprising first and second elongated suction channels and a helical needle suturing device. The procedure may involve capturing an anterior portion of the stomach wall in the first suction channel, capturing a posterior portion of the stomach wall with the second suction channel, and then helically suturing the captured anterior portion to the captured posterior portion with the suturing device. During some or all of the procedure, the elongated body may be anchored in position as described above. The suturing may be along a generally helical path having an axis inside the working portion of the elongated body and it may be in a distal to proximal or proximal to distal direction. The suturing device may be integral with or slideably disposed within the working portion of the elongated body.

What has also been described is a novel surgical system comprising an elongated body adapted to be inserted into an esophagus with a proximal end extending from a body orifice, the elongated body including a tapered distal portion and a working portion having an outer surface defining at least one side opening therein, at least one working member disposed within the working portion of the elongated body, the at least one working member comprising at least two tissue acquisition and excision assemblies, the assemblies each comprising a suction cavity open to the at least one side opening and an excision device for excising at least the mucosal layer of tissue captured in the cavity.

What has also been described is a novel surgical system comprising
an elongated body constructed and arranged to be inserted into a patient with a proximal end extending from the patient while a working portion thereof is disposed in the patient, the working portion including at least one suction cavity for capturing tissue, at least one suction lumen for supplying suction to the cavity, a positioning lumen for receiving a balloon catheter positioning device, and at least one needle for placing suture through the tissue captured in the cavity. The proximal end of the balloon catheter may have a self closing valve and/or it may be constructed such that the working portion can be inserted over the balloon catheter when the balloon is inflated in the patient. The working portion may also include at least one cutting device for sectioning a portion of the tissue captured in the cavity and/or an infusate lumen for delivering infusate to tissue captured in the suction cavity. The needle may be a curved (or an array thereof), and the working portion may include a needle actuator such as a roller or pull wire (or pair thereof). The elongated body may include an endoscope lumen, and the endoscope lumen may be separate from the working portion or it may extend partially into or wholly through the working portion. Some or all of the components of the working portion may be slideably disposed in the elongated body either individually or as an integrated whole.

What has also been disclosed is a novel surgical system comprising an elongated body constructed and arranged to be inserted into a patient with a proximal end extending from the patient while a working portion thereof is disposed in the patient, wherein the working portion comprises at least one side disposed suction cavity for capturing tissue; at least one suction lumen for supplying suction to the cavity; at least one curved needle for placing suture through the tissue captured in the cavity; and at least two lumens receiving means for actuating the needle. The means for actuating the needle may be a roller(s) or pull wire(s). The working portion may further include a positioning lumen for receiving a removable positioning device (e.g. balloon catheter or orientation wire), an infusate lumen for delivering infusate to tissue captured in the suction cavity, and/or a cutting device for sectioning a portion of the tissue captured in the cavity. The elongated body may include an endoscope lumen, and the endoscope lumen may be separate from the working portion or it may extend partially into or wholly through the working portion. Some or all of the components of the working portion may be slideably disposed in the elongated body either individually or as an integrated whole.

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding. Thus, the specifics of this description and the attached drawings should not be interpreted to limit the scope of this invention to the specifics thereof. It is to be understood that when words such as "a", "an", and "at least one" are used, there is no intention to limit to only one item unless specifically stated to the contrary. Furthermore, when the language "at least a portion" and/or "a portion" is used, a portion and/or the entire item may be present. Finally, all publications, patents, and patent applications cited in this specification are herein incorporated by reference to the extent not inconsistent with the present disclosure as if each were specifically and individually indicated to be incorporated by reference and set forth in its entirety herein.

What is claimed is:

1. A system for performing a gastrointestinal procedure comprising:
   an elongated body having a longitudinal axis, the elongated body defining an endoscope lumen and constructed and arranged to be inserted into the esophagus with a proximal end extending from a body orifice, wherein the body defines a distal end and a working portion proximal to the distal end;
   at least one elongated side disposed suction cavity in the working portion for capturing tissue;
   at least one cutting device positioned in opposing slots in side walls of the suction cavity for resecting an elongated surface layer from the captured tissue portion so as to produce an elongated section of exposed tissue;
   at least one needle adapted to be passed into the captured tissue portion, the needle having a sharp end portion opposite a back end portion and a main body that spans between the sharp and the back end portions, the needle defining a slot;
   a shuttle having a first position wherein the shuttle contacts the needle at the back end portion and the shuttle having a second position wherein the shuttle contacts the needle at the sharp end portion, the shuttle releasing the needle when moving from the first position to the second position to advance the needle into the captured tissue portion; and a longitudinally operable locking bar having a first recess adjacent a second recess, the first recess is sized to engage the slot on the needle to lock the needle in a desired position, and the second recess is sized to accommodate the main body of the needle to unlock the needle to enable movement of the needle.

2. The system of claim 1 wherein the endoscope lumen terminates distally in an endoscope exit hole in the body that is proximal to the distal end of the body.

3. The system of claim 2 wherein the endoscope exit hole is proximal to the at least one elongated side disposed suction cavity.

4. The system of claim 1 wherein the at least one needle includes a suturing needle that is adapted to apply suture to the captured tissue portion so as to allow the elongated section of exposed tissue to be placed in apposition with another elongated section of exposed tissue to which it is to be joined.

5. The system of claim 4 wherein the suturing needle is a curved needle that operates in a direction transverse to a longitudinal axis defined by the working portion so as to apply transverse sutures along the length of the elongated section of exposed tissue.

6. The system of claim 4 wherein the system is configured to operate at the gastroesophageal junction to form a plication upon securing at least two captured and resected tissue portions together with the suture.

7. The system of claim 4 wherein the system is configured to reduce the size of the stomach upon securing captured and resected tissue portions together with the applied suture.

8. The system of claim 4 further comprising a device for installing a knotting element to the free ends of sutures so as to join two elongated sections of exposed tissue together.

9. The system of claim 1 wherein the shuttle is operated by first and second pull wires, the first and the second pull wires each positioned in a lumen, each of the lumens span perpendicular to the needle.

10. The system of claim 1 wherein the at least one needle comprises a longitudinally operable injection needle operable to deliver injectate into the captured tissue portion.

11. The system of claim 10 wherein a distal wall of the suction cavity defines an opening for receiving the distal tip of the injection needle.

12. The system of claim 10 wherein the injection needle is positioned to inject the captured tissue between a resection plane defined by the cutting device and the floor of the suction cavity.

13. The system of claim 1 wherein the cutting device is a blade.

14. The system of claim 13 further comprising a plurality of needles extending from the floor of the suction cavity.

15. The system of claim 1 wherein at least a portion of the elongated body defines an effective outer diameter in the range of 15-20 mm.

16. The system of claim 1 wherein the locking bar includes a transition region that spans between the first and the second recesses, the transition region configured to engage the needle to maintain the needle in alignment while the needle advances into the captured tissue portion.

17. An endoscopic suturing device comprising:
an elongated body having a longitudinal axis, the elongated body defining an endoscope lumen and having a distal portion adapted to be inserted into a body while a proximal portion is extending from a body orifice;

wherein the distal portion comprises an elongated side disposed suction cavity and an array of transverse curved suturing needles for applying multiple sutures to the tissue that has been captured in the suction cavity, each of these needles having a sharp end opposite a back end and a main body that spans between the sharp and the back ends, each of the needles defining a slot;

a needle actuator having a first position wherein the needle actuator contacts the needles at the back end portions, the needle actuator having a second position wherein the needle actuator contacts the needles at the sharp end portions, wherein the needle actuator releases the needles when moving from the first position to the second position to advance the suturing needles; and a longitudinally operable locking bar having a plurality of first recesses adjacent a plurality of second recesses, each of the first recesses is sized to engage the slot on one of the needles to lock each of the needles in a desired position, and each of the second recesses is sized to accommodate the main body of one of the needles to unlock each of the needles to enable movement of each of the needles.

18. The suturing device of claim 17 wherein the elongated body further defines at least one suction lumen for supplying suction to the cavity and at least two lumens receiving means for actuating the needles.

19. The suturing device of claim 18 wherein the means for actuating the needles comprise first and second pull wires, the first and the second pull wires each positioned in a lumen, each of the lumens span perpendicular to the needles.

20. The suturing device of claim 17 wherein the suturing needles are advanced by the needle actuator that is made to rotate in a clockwise direction when a first wire is pulled and in a counterclockwise direction when a second wire is pulled.

21. The suturing device of claim 17 wherein the suturing needles are advanced by the needle actuator that engages with each needle at at least two different locations on the needle during the course of passing the needle through the tissue.

22. The suturing device of claim 17 wherein the endoscope lumen terminates in an endoscope exit hole in an outer surface of the elongated body that is proximal to the suction cavity.

23. The suturing device of claim 17 wherein the device is adapted to be introduced into the stomach transorally.

24. The system of claim 17 wherein the locking bar includes a transition region that spans between the first and the second recesses, the transition region configured to engage the needle to maintain the needle in alignment while the needle advances into the captured tissue portion.

* * * * *